US007838274B2

(12) United States Patent
Albermann et al.

(10) Patent No.: US 7,838,274 B2
(45) Date of Patent: Nov. 23, 2010

(54) PHOSPHOLIPASES AND USES THEREOF

(75) Inventors: Kaj Albermann, Martinsried (DE);
Wolfram Kemmner, Munich (DE);
Dieter Maier, Martinsried (DE); Fabio Spreafico, Lecco (IT); Alexander Stock, Martinsried (DE); Christian Wagner, Martinsried (DE); Lex De Boer, Wateringen (NL); Roelf Bernhard Meima, Kamerik (NL)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 12/461,287

(22) Filed: Aug. 6, 2009
(Under 37 CFR 1.47)

(65) Prior Publication Data

US 2010/0047877 A1 Feb. 25, 2010

Related U.S. Application Data

(60) Division of application No. 11/544,679, filed on Oct. 10, 2006, now Pat. No. 7,588,925, which is a continuation of application No. 10/514,998, filed as application No. PCT/EP03/05450 on May 21, 2003, now abandoned.

(30) Foreign Application Priority Data

| May 21, 2002 | (EP) | ................................. | 02100521 |
| May 21, 2002 | (EP) | ................................. | 02100524 |
| May 21, 2002 | (EP) | ................................. | 02100528 |
| May 21, 2002 | (EP) | ................................. | 02100538 |

(51) Int. Cl.
*C12N 9/16* (2006.01)
*C12N 1/20* (2006.01)
*C12N 15/00* (2006.01)
*C12N 9/18* (2006.01)
*C07H 21/04* (2006.01)
*C12P 21/06* (2006.01)

(52) U.S. Cl. ...................... 435/196; 435/325; 435/197; 435/320.1; 435/440; 435/69.1; 536/23.2

(58) Field of Classification Search ...................... None
See application file for complete search history.

(56) References Cited

U.S. PATENT DOCUMENTS

| 4,433,092 | A | 2/1984 | Nemeth |
| 4,567,046 | A | 1/1986 | Inoue et al. |
| 4,631,211 | A | 12/1986 | Houghten |
| 4,704,692 | A | 11/1987 | Ladner |
| 4,708,781 | A | 11/1987 | Poorten |
| 4,946,778 | A | 8/1990 | Ladner et al. |
| 5,194,392 | A | 3/1993 | Geysen |
| 5,223,409 | A | 6/1993 | Ladner et al. |
| 5,264,367 | A | 11/1993 | Aalrust et al. |
| 5,480,971 | A | 1/1996 | Houghten et al. |
| 6,146,869 | A | 11/2000 | Harris et al. |
| 2007/0207521 | A1 | 9/2007 | Albermann et al. |

FOREIGN PATENT DOCUMENTS

| CZ | 190264 | 10/1981 |
| EP | 0219269 | 9/1981 |
| EP | 0109244 | 4/1987 |
| EP | 0075463 | 5/1987 |
| EP | 0426211 | 11/1993 |
| EP | 0619947 | 4/1997 |
| EP | 0808903 | 11/1997 |
| EP | 0654527 | 1/1998 |
| EP | 0659344 | 7/2001 |
| JP | 60-078529 | 5/1985 |
| JP | 62-111629 | 5/1987 |
| JP | 63-258528 | 10/1988 |
| JP | 02-153997 | 6/1990 |
| JP | 10-155493 | 6/1998 |
| WO | 90/02809 | 3/1990 |
| WO | 91/17271 | 11/1991 |
| WO | 92/01047 | 1/1992 |
| WO | 92/09690 | 6/1992 |
| WO | 92/15679 | 9/1992 |
| WO | 92/18619 | 10/1992 |

(Continued)

OTHER PUBLICATIONS

Berka et al. "*Aspergillus orizae* EST SEQ ID No. 4754" EMBL Database accession No. AAF12231 (Sep. 2000).
Chakravarti et al. "Studies on phospholipase activities in *Neurospora crassa* conidia" Arch. Biochem. Biophys. 206:393-402 (1981).
Chen et al. "Identification of extracellular phospholipase B, lysophospholipase, and acyltransferase produced by *Cryptococcus neoformans*" Infec. Immun. 65:405-411 (1997).
Chica et al. "Semi-rational approaches to engineering enzyme activity: Combining the benefits of directed evolution and rational design" Curr. Opn. Biotechnol. 16:378-384 (2005).

(Continued)

*Primary Examiner*—Delia M Ramirez
*Assistant Examiner*—M D. Younus Meah
(74) *Attorney, Agent, or Firm*—Nixon & Vanderhye P.C.

(57) ABSTRACT

The invention relates to a newly identified polynucleotide sequence comprising a gene that encodes a novel phospholipase isolated from *Aspergillus niger*. The invention features the full length nucleotide sequence of the novel gene, the cDNA sequence comprising the full length coding sequence of the novel phospholipase as well as the amino acid sequence of the full-length functional protein and functional equivalents thereof. The invention also relates to methods of using these enzymes in industrial processes and methods of diagnosing fungal infections. Also included in the invention are cells transformed with a polynucleotide according to the invention and cells wherein a phospholipase according to the invention is genetically modified to enhance or reduce its activity and/or level of expression.

20 Claims, No Drawings

FOREIGN PATENT DOCUMENTS

| | | |
|---|---|---|
| WO | 92/20791 | 11/1992 |
| WO | 93/01288 | 1/1993 |
| WO | 95/00636 | 1/1995 |
| WO | 98/26057 | 6/1998 |
| WO | 98/45453 | 10/1998 |
| WO | 00/32758 | 6/2000 |
| WO | 01/11974 | 2/2001 |
| WO | 02/26044 | 4/2002 |
| WO | 02/49441 | 6/2002 |

OTHER PUBLICATIONS

Fifis et al. "Evidence for phospholipase B activity in *Fusobacterium necrophorum* cultures and its association with hemolysin/leucocidin activities" Vet. Microbiol. 49:219-233 (1996).

Ichimasa et al. Purification and some properties of soluble phospholipase B from baker's yeast (*Saccharomyces cerevisiae*) Agric. Biol. Chem. 49:1083-1089 (1985).

Kawasaki et al. "Studies on a phospholipase B from *Penicillium notatum*. Purification, properties, and mode of action" J. Biochem. 77:1233-1244 (1975).

Kuwabara et al. "Purification and some properties of water-soluble phospholipase B from *Torulaspora delbrueckir*" Agric. Biol. Chem. 52:2451-2458 (1988).

Lee et al. "The *Saccharomyces cerevisiae* PLB1 gene encodes a protein required for lysophospholipase and phospholipase B activity" J. Biol. Chem. 269:19725-19730 (1994).

Machida et al. "*Aspergillus oryzae* polynucleotide SEQ ID No. 5401" EMBL Database accession No. ABZ56288 (Oct. 2002).

Masuda et al. "Primary structure of protein moiety of *Penicillium notatum* phospholipase B deduced from the cDNA" Eur. J. Biochem. 202:783-787 (1991).

Mustranta et al. "Comparison of lipases and phospholipases in the hydrolysis of phospholipids" Process Biochem. 30:393-401 (1995).

Saito et al. "Phospholipase B from *Penicillium notatum*" Meth. Enzymol. 197:446-456 (1991).

Seffernick et al. "Melamine deaminase and atrazine chlorohydrolase: 98 percent identical but functionality different" J. Bacteriol. 183:2405-2410 (2001).

Tseung et al. "Production of phosphatidases by phytopathogens" Phytopathol. Notes 58:1437-1438 (1968).

Uehara et al. "Purification and properties of phospholipase $A_1$ produced by *Corticium centrifugum*" Agric. Biol. Chem. 43:517-525 (1979).

Watanabe et al. "Cloning and sequencing of phospholipase B gene from the yeast *Torulaspora delbrueckir*"FEMS Microbiol. Lett. 124:29-34 (1994).

Witkowski et al. "Conversion of a β-ketoacyl synthase to a malonyl decarboxylase by replacement of the active-site cysteine with glutamine" Biochem. 38:11643-11650 (1999).

International Search Report for PCT/EP2003/05450 completed Aug. 13, 2003.

International Preliminary Examination Report for PCT/EP2003/05450 completed Oct. 28, 2004.

SEQUENCE LISTING

```
<160> NUMBER OF SEQ ID NOS: 15

<210> SEQ ID NO 1
<211> LENGTH: 3763
<212> TYPE: DNA
<213> ORGANISM: Aspergillus niger

<400> SEQUENCE: 1
ggtggatgat agcacacggg cgacgcaaga tcgagaaata acttggtcat cattatttct      60
tgtgggtaag caagagtctt ataggggtc ctgctgtggt ctgcgacatc tggtggatgt     120
ggatggacga tgatgaagat gggggaacta ttcccaatgc ggtgcgcggg tgcgatggaa     180
tggacaggaa gagaattttt catctcagga ttggggaaat ggttgaactc gaccggtgtg     240
tgtgtgccgt tgaagcagct ggagtgttat ctgtagtatc tacggtctat gcgcatcatc     300
ttcaacagat ccgaccagag tgtgaaagat gccatcgaag aaagaaaaat aactaaaccc     360
ggtcgggact gctatcgaca gcctgaggca gtaaggcagt gaggcagtga ggcagtgagg     420
cagtgaggca gtcaggtgat gatcaggcat ccaatcatct ctgcctcgcc gccttgccgc     480
ctggggtgtc aaggcgaagg accagctcgt catccgatcg agatccatcc cgaataatgt     540
ccaggctgtt cgcagtgcct ggtgctagtt gtagatatat gggttatgat atctcactgt     600
tctctaccat ccttcctgtt cctggctctc tgctgtggtg tgtatccgag cgggccggaa     660
gctaccgatc gccggattgt tccggccctt ttcttattcc atgggctgtg cccttactct     720
gcctctcttt ctatctttct ctctctctct ctctctctga ttcgttccca atggagaatt     780
caggtacaaa gtaattccct ctggcatgac tgcttgacat gtcgccattc aacatcatga     840
agtactaagt agtagtagac caactactct ggacggctga tagcagccaa tcacgggaaa     900
gtggccacgc acggggggctg tcgatccccg atgatcgtgc attggcagag ccatgaagaa     960
agacggtagg acaagcctcg accagtctct gctacagtgt atccctccc agatatgggg    1020 taaaccctca aataccgtcc gacccggtcc ctcgtgcccc tgcagatcga tgccattgga    1080
gttgcatccg gccttcgcgt ctccaccgat ggagaaggga gggtgaataa tggcgtccat    1140
gcaaatggct cgcttgactc acaagatgta gtacttgttt aatgaaaata gatggtgtct    1200
cgaccacttg acaccaccac gtgcagaccc tgcaagggga gagatgagga gaaaagctgt    1260
ccgagtgaca gctccaactc caccctgacc atggtataag aaggctcccc ctcgaccatc    1320
ttgtcaatgg ctattctcac cagggtatcg cattctgcct cctccatctg tactacaaat    1380
tacaacagag ctcaccatgc atcccagtgc gctggtcggt ctgctggcct tgctgccgc    1440
```

```
tgcctcggcc atccccgcca accccagcca taaggctcac tccgactcgg ccgtccagaa  1500
tctcaagtcg aagatcaaga atgtcgtcgt cctggtcatg gagaatcgtt ccgtggacaa  1560
cctgttggga ggtcagacga tcaagggctt ggagaacccc atcaacaacg cccctactg   1620
caaccectac aacatcaccg acctctccca gggcaccgtc tgcagtgcgg ccagagacta  1680
cgactcggtc accgatgatc ccgatcacgc cgtctatggc aataacatcg agttctacgg  1740
caccttcacc cccgacaatg cggccatcgc ccagggcaag ctgaccccct cccagcaggg  1800
gttcgtcacg gaacagctgc gcctgtacag cgccgatgcc aaccgcaccg agctgtccgt  1860
gcaggtcatg aactattaca ccgagcagca ggtgcccgtg ctcacctcgc tcgtccaaaa  1920
ctatgtcgtt ttcaaccatt ggcactcgga tgtgcctggt gtacgaaccc ccccttctt   1980
cccctteece acctttcagc tggcaacttg ctaactcaga ttcagcccac caaccccaac  2040
cgggctgccc tcacctctgg cacttcgtat ggtcacggaa ccaacgatga ggcctttgac  2100
aaccacgcct tcccccagcg ttccatcttc cagcagctga ccgagaccgg ccactcctgg  2160
atcaactact gggacacggc tggtggcact ggccccgatg ccgagttcta caactggact  2220
tacacctcca acaacaccga caaggtcaag gccctggaac agttctacac ggatgccgca  2280
gccggtgccc tgcctgaatt cagctacgtc aaccectcgt gctgcggtgt cggcaccaac  2340
tcgatgcacc ccagtggtct gatctccgac ggcgagaagc tgatcaagaa cgtctacgac  2400
gctctgcgcg ccgggcccca gtggaacgag accctcttca tcctgagctt cgacgagacc  2460
ggtggcttcc acgaccatgt gccccgccc ctcgctcccc ggccggacaa cctcacttac  2520
acggccacca ccccaagcgg cgaggactac accttcaact ttaaccgtct gggtggtcgt  2580
atccccactc tgctgatctc ccctgggtc ggcaagggat atgtcgagca aaagggcacc  2640
agcgtcaccg gcgaaaccgt gtcttactcc gcctcctcga tcctgcgcac cctgggctac  2700
ctctgggact ttgacccttt caccccgcgg gtcgagtatg cgccatcctt tgagcatctg  2760
gtgcagacgc gggcccgcga taacacccg actgccttgc cgagtccggt gccctttcgg  2820
aagtaaatgg cagatattga atgcggtagt ggaaacgtct aatgcataat gaacggaggg  2880
aaagtagatc tgaaaagctg agccgcgtcc gagatacaca tgtttggtca gatatttcct  2940
gggcttagca cggtacagag gatgataggt catgtattat tcatgataaa gccaaaataa  3000
atagtatttg taatacattg atggccatcg ctggctgttg ttggacattc cttatgatct  3060
cttccacgac tattactgat tggggcccaa taacaagctg cggaagaata ttccaatcac  3120
aattgacatg tcttgcggca gtttatagaa attccgtaga tttcaggctt tgcactccac  3180
cctgtataca catgactttt ataacgttct tcacgcaatc tatatactgg tctacatcaa  3240
cccatcctgg ctctctgaaa catggttgag caggagcagc ttgcactctg agtcctactt  3300
tattttcaat ccattcctaa ataccgtgag aaaggcaggg aacctaccat ggccttgcc   3360
caccaccttg tcgaagaagg tctggctcgg tcgcttcctc aacccaccga cgcctcctcc  3420
cggtacctcc agggtcgact ggcccgacct tctgcacaat agattgaatg cgtgtcaaga  3480
agccctccgt ctcgagctgt tccggtggcg tatttcgcag cacctgcaga gtgacccag   3540
cgagcagcac tccctcgcga ctccgttcgt aatgttcaag cgacgcgagc gccatcccga  3600
caggtctata catccaagct ctgaagccgc ggattacgag ctttcccgag atgcttaagg  3660
tgctacaaga tgcatagtta cggtggataa ttataggggt cctagagagc agcattcgca  3720
gaagagcaac actatagggc cccttgggcc atctttgaga cta                    3763
```

<210> SEQ ID NO 2
<211> LENGTH: 1365
<212> TYPE: DNA
<213> ORGANISM: Aspergillus niger
<220> FEATURE:
<221> NAME/KEY: CDS
<222> LOCATION: (1)..(1365)

<400> SEQUENCE: 2

```
atg cat ccc agt gcg ctg gtc ggt ctg ctg gcc ttt gct gcc gct gcc      48
Met His Pro Ser Ala Leu Val Gly Leu Leu Ala Phe Ala Ala Ala Ala
1               5                  10                  15 tcg gcc atc ccc gcc aac ccc agc cat aag gct cac tcc gac tcg gcc      96
Ser Ala Ile Pro Ala Asn Pro Ser His Lys Ala His Ser Asp Ser Ala
                20                  25                  30 gtc cag aat ctc aag tcg aag atc aag aat gtc gtc gtc ctg gtc atg     144
Val Gln Asn Leu Lys Ser Lys Ile Lys Asn Val Val Val Leu Val Met
            35                  40                  45 gag aat cgt tcc gtg gac aac ctg ttg gga ggt cag acg atc aag ggc     192
Glu Asn Arg Ser Val Asp Asn Leu Leu Gly Gly Gln Thr Ile Lys Gly
50                  55                  60 ttg gag aac ccc atc aac aac ggc ccc tac tgc aac ccc tac aac atc     240
Leu Glu Asn Pro Ile Asn Asn Gly Pro Tyr Cys Asn Pro Tyr Asn Ile
65                  70                  75                  80 acc gac ctc tcc cag ggc acc gtc tgc agt gcg gcc aga gac tac gac     288
Thr Asp Leu Ser Gln Gly Thr Val Cys Ser Ala Ala Arg Asp Tyr Asp
                85                  90                  95 tcg gtc acc gat gat ccc gat cac gcc gtc tat ggc aat aac atc gag     336
Ser Val Thr Asp Asp Pro Asp His Ala Val Tyr Gly Asn Asn Ile Glu
            100                 105                 110 ttc tac ggc acc ttc acc ccc gac aat gcg gcc atc gcc cag ggc aag     384
Phe Tyr Gly Thr Phe Thr Pro Asp Asn Ala Ala Ile Ala Gln Gly Lys
        115                 120                 125 ctg acc ccc tcc cag cag ggg ttc gtc acg gaa cag ctg cgc ctg tac     432
Leu Thr Pro Ser Gln Gln Gly Phe Val Thr Glu Gln Leu Arg Leu Tyr
    130                 135                 140 agc gcc gat gcc aac cgc acc gag ctg tcc gtg cag gtc atg aac tat     480
Ser Ala Asp Ala Asn Arg Thr Glu Leu Ser Val Gln Val Met Asn Tyr
145                 150                 155                 160 tac acc gag cag cag gtg ccc gtg ctc acc tcg ctc gtc caa aac tat     528
Tyr Thr Glu Gln Gln Val Pro Val Leu Thr Ser Leu Val Gln Asn Tyr
                165                 170                 175 gtc gtt ttc aac cat tgg cac tcg gat gtg cct ggt ccc acc aac ccc     576
Val Val Phe Asn His Trp His Ser Asp Val Pro Gly Pro Thr Asn Pro
            180                 185                 190 aac cgg gct gcc ctc acc tct ggc act tcg tat ggt cac gga acc aac     624
Asn Arg Ala Ala Leu Thr Ser Gly Thr Ser Tyr Gly His Gly Thr Asn
        195                 200                 205 gat gag gcc ttt gac aac cac gcc ttc ccc cag cgt tcc atc ttc cag     672
Asp Glu Ala Phe Asp Asn His Ala Phe Pro Gln Arg Ser Ile Phe Gln
    210                 215                 220 cag ctg acc gag acc ggc cac tcc tgg atc aac tac tgg gac acg gct     720
Gln Leu Thr Glu Thr Gly His Ser Trp Ile Asn Tyr Trp Asp Thr Ala
225                 230                 235                 240 ggt ggc act ggc ccc gat gcc gag ttc tac aac tgg act tac acc tcc     768
Gly Gly Thr Gly Pro Asp Ala Glu Phe Tyr Asn Trp Thr Tyr Thr Ser
                245                 250                 255 aac aac acc gac aag gtc aag gcc ctg gaa cag ttc tac acg gat gcc     816
Asn Asn Thr Asp Lys Val Lys Ala Leu Glu Gln Phe Tyr Thr Asp Ala
            260                 265                 270
```

```
gca gcc ggt gcc ctg cct gaa ttc agc tac gtc aac ccc tcg tgc tgc         864
Ala Ala Gly Ala Leu Pro Glu Phe Ser Tyr Val Asn Pro Ser Cys Cys
            275                 280                 285 ggt gtc ggc acc aac tcg atg cac ccc agt ggt ctg atc tcc gac ggc         912
Gly Val Gly Thr Asn Ser Met His Pro Ser Gly Leu Ile Ser Asp Gly
    290                 295                 300 gag aag ctg atc aag aac gtc tac gac gct ctg cgc gcc ggg ccc cag         960
Glu Lys Leu Ile Lys Asn Val Tyr Asp Ala Leu Arg Ala Gly Pro Gln
305                 310                 315                 320 tgg aac gag acc ctc ttc atc ctg agc ttc gac gag acc ggt ggc ttc        1008
Trp Asn Glu Thr Leu Phe Ile Leu Ser Phe Asp Glu Thr Gly Gly Phe
                325                 330                 335 cac gac cat gtg ccc ccg ccc ctc gct ccc cgg ccg gac aac ctc act        1056
His Asp His Val Pro Pro Pro Leu Ala Pro Arg Pro Asp Asn Leu Thr
            340                 345                 350 tac acg gcc acc acc cca agc ggc gag gac tac acc ttc aac ttt aac        1104
Tyr Thr Ala Thr Thr Pro Ser Gly Glu Asp Tyr Thr Phe Asn Phe Asn
    355                 360                 365 cgt ctg ggt ggt cgt atc ccc act ctg ctg atc tcc ccc tgg gtc ggc        1152
Arg Leu Gly Gly Arg Ile Pro Thr Leu Leu Ile Ser Pro Trp Val Gly
370                 375                 380 aag gga tat gtc gag caa aag ggc acc agc gtc acc ggc gaa acc gtg        1200
Lys Gly Tyr Val Glu Gln Lys Gly Thr Ser Val Thr Gly Glu Thr Val
385                 390                 395                 400 tct tac tcc gcc tcc tcg atc ctg cgc acc ctg ggc tac ctc tgg gac        1248
Ser Tyr Ser Ala Ser Ser Ile Leu Arg Thr Leu Gly Tyr Leu Trp Asp
                405                 410                 415 ttt gac cct ttc acc ccg cgg gtc gag tat gcg cca tcc ttt gag cat        1296
Phe Asp Pro Phe Thr Pro Arg Val Glu Tyr Ala Pro Ser Phe Glu His
            420                 425                 430 ctg gtg cag acg cgg gcc cgc gat aac acc ccg act gcc ttg ccg agt        1344
Leu Val Gln Thr Arg Ala Arg Asp Asn Thr Pro Thr Ala Leu Pro Ser
    435                 440                 445 ccg gtg ccc ttt cgg aag taa                                            1365
Pro Val Pro Phe Arg Lys
450
```

<210> SEQ ID NO 3
<211> LENGTH: 454
<212> TYPE: PRT
<213> ORGANISM: Aspergillus niger

<400> SEQUENCE: 3

```
Met His Pro Ser Ala Leu Val Gly Leu Leu Ala Phe Ala Ala Ala
1               5                   10                  15

Ser Ala Ile Pro Ala Asn Pro Ser His Lys Ala His Ser Asp Ser Ala
                20                  25                  30

Val Gln Asn Leu Lys Ser Lys Ile Lys Asn Val Val Leu Val Met
            35                  40                  45

Glu Asn Arg Ser Val Asp Asn Leu Leu Gly Gly Gln Thr Ile Lys Gly
        50                  55                  60

Leu Glu Asn Pro Ile Asn Asn Gly Pro Tyr Cys Asn Pro Tyr Asn Ile
65                  70                  75                  80

Thr Asp Leu Ser Gln Gly Thr Val Cys Ser Ala Ala Arg Asp Tyr Asp
                85                  90                  95

Ser Val Thr Asp Asp Pro Asp His Ala Val Tyr Gly Asn Asn Ile Glu
            100                 105                 110

Phe Tyr Gly Thr Phe Thr Pro Asp Asn Ala Ala Ile Ala Gln Gly Lys
        115                 120                 125
```

```
Leu Thr Pro Ser Gln Gln Gly Phe Val Thr Glu Gln Leu Arg Leu Tyr
    130                 135                 140

Ser Ala Asp Ala Asn Arg Thr Glu Leu Ser Val Gln Val Met Asn Tyr
145                 150                 155                 160

Tyr Thr Glu Gln Gln Val Pro Val Leu Thr Ser Leu Val Gln Asn Tyr
                165                 170                 175

Val Val Phe Asn His Trp His Ser Asp Val Pro Gly Pro Thr Asn Pro
            180                 185                 190

Asn Arg Ala Ala Leu Thr Ser Gly Thr Ser Tyr Gly His Gly Thr Asn
        195                 200                 205

Asp Glu Ala Phe Asp Asn His Ala Phe Pro Gln Arg Ser Ile Phe Gln
    210                 215                 220

Gln Leu Thr Glu Thr Gly His Ser Trp Ile Asn Tyr Trp Asp Thr Ala
225                 230                 235                 240

Gly Gly Thr Gly Pro Asp Ala Glu Phe Tyr Asn Trp Thr Tyr Thr Ser
                245                 250                 255

Asn Asn Thr Asp Lys Val Lys Ala Leu Glu Gln Phe Tyr Thr Asp Ala
            260                 265                 270

Ala Ala Gly Ala Leu Pro Glu Phe Ser Tyr Val Asn Pro Ser Cys Cys
        275                 280                 285

Gly Val Gly Thr Asn Ser Met His Pro Ser Gly Leu Ile Ser Asp Gly
    290                 295                 300

Glu Lys Leu Ile Lys Asn Val Tyr Asp Ala Leu Arg Ala Gly Pro Gln
305                 310                 315                 320

Trp Asn Glu Thr Leu Phe Ile Leu Ser Phe Asp Glu Thr Gly Gly Phe
                325                 330                 335

His Asp His Val Pro Pro Leu Ala Pro Arg Pro Asp Asn Leu Thr
            340                 345                 350

Tyr Thr Ala Thr Thr Pro Ser Gly Glu Asp Tyr Thr Phe Asn Phe Asn
        355                 360                 365

Arg Leu Gly Gly Arg Ile Pro Thr Leu Leu Ile Ser Pro Trp Val Gly
    370                 375                 380

Lys Gly Tyr Val Glu Gln Lys Gly Thr Ser Val Thr Gly Glu Thr Val
385                 390                 395                 400

Ser Tyr Ser Ala Ser Ser Ile Leu Arg Thr Leu Gly Tyr Leu Trp Asp
                405                 410                 415

Phe Asp Pro Phe Thr Pro Arg Val Glu Tyr Ala Pro Ser Phe Glu His
            420                 425                 430

Leu Val Gln Thr Arg Ala Arg Asp Asn Thr Pro Thr Ala Leu Pro Ser
        435                 440                 445

Pro Val Pro Phe Arg Lys
    450

<210> SEQ ID NO 4
<211> LENGTH: 3692
<212> TYPE: DNA
<213> ORGANISM: Aspergillus niger

<400> SEQUENCE: 4 tttgggggttg gtcgtgtgcg tcctgtgctg tcctgtcttg aaccgaacca gactggcagg      60
gactattatt ccgagtattc cccggcgaag gatggcagtg atgagacatt cggctggatt     120
ggatcggacc cctgctgatc agctcgggga attctcctat tccgtgggat tgattctttt     180 cttttttcttt tctattctat gctatgcaaa agacgtgatg tgtgtctggt tggcgttcca    240
```

```
ggagcgaaga ttgcttttct tactatatta ttccttcttc tatgttcttg aattagctat      300
gcaggtagcg gtcaatatat cctttaagca gatacctttα ctcttgctat ggatatcata      360
atcctagaag gtacatccac catagactac ctagtccccg gccacatcat gaaatatcac      420
tggtacatta ttctccgaga accacagaac cactccatag cacaggcaca taatggcacc      480
tgcccacacc cacactcacg gctcctagta ctaacccctc gtagtcccca gtactccaca      540
ggtacctaat acacttgtcc cacaccctca ccaagaccaa ctaaccacca aagctactcg      600
cagatagcaa gatagtcacc tgccacaccg caactcacta caaaacgcag atcacaagcc      660
taaatattcg aaccaaacct gaagaatcct ttccaaccaa cacacacacg gtatgggttg      720
gaaggaaggg aaagaaagtg gggttaagca aactaactaa caaactctgc aaggtagcaa      780
acgctacact aaccaaccaa actagttaaa ctaatattaa taataataat aagaagaaga      840
agatgatgat gaaggagtca tcgttctccc gtccccggct tatagtacgg gatgctaagg      900
ctgcaccccg cagcacggga agcccggacg ttggtggttt gcgggtgggt gactggatta      960
gactagggga ctcgtaaggc agcggactag ttaaattaat tgactagtag tctgtgctgg     1020
gctgggctta tctagtactg tgaagtgccg ggatgtgccg ggtgagtgaa gagttcatta     1080
atgaatgatt gattgatttg cggggtggt aggtgtagcg ttaggtaatg gaaccacttc      1140
ttataattgt attactctac taactgtaaa tgtgtgtgtt ttatggggac aggagaagtt     1200
aaggtagtat tgggggcggg aaaagggat ggttgtctaa ttcagtttgt ttcaatagtt      1260
tgttgaggta ttttcttgtc aaagttactt gttcagatta tgggcacgtg tacgtgctta     1320
gttttcatag attgtgtgta tgtgtgtgtg tgcgcgtgcg tgctgaccca tctatagcat     1380
gtatcgcggt ctgaatgtgt ataagcgctg caagtgatcg gcaaagtgac aagaagtctt     1440
tctacgaccc actagttatt tgcatgtcac gaaccacaac accgccagtc acagcgacag     1500
catgtgaaga agtctcagat ttcgtaacac tctcccgtct actgctctcc tacttgatag     1560
actgacttac ctcggcctgt gcacatgcca tgtccctatc ccaatctact ggtccatgtg     1620
cagaccacgc ctccacgttt ctccgccagt agatccttca acaccgctca tcctcagaca     1680
acatctactt tatttgactt ttcggagaag accatgcttg tctacggcca gctatagcat     1740
gctatagcag tccgttaatc tccaccgggc tcccgctccg aacggagatg gggccaaact     1800
gccactccag ttgcgcaacg gacaggcacc gaaccggaac aaaggatgcg gaagaggaga     1860
catggtgcct gattgcatgt gctggcttca tctgctatcg tgagggtgct gtgctggaga     1920
aatttgttgt ctgacttacc ccgcttcttg cttttttttcc ccctgatgcc cctgatgggg     1980
aattggggtg ggtaatatga tacaggtata aaagggggct cggaggtgca gttggataga     2040
agcattgtgt gtgcattgca gcagtccgtt ggtctcacgt ctctggttgc ctcgattgta     2100
tatatactgc aggatgttct ctggacggtt tggagtgctt ttgacggcgc tcgctgcgct     2160
gagtgctgcg gcaccgacac cacttgatgt gcggagtagg tgtgcctgat ttgaagtggc     2220
tggatagcac tgatgaaggt tttgaatagg tgtctcgact tccacgttgg atgagctgca     2280
attgttctcg caatggtctg ccgcagctta ttgctcgaac aatatcgact cggacgactc     2340
taacgtgaca tgcacggccg acgcctgtcc atcagtcgag gaggcgagca ccaagatgct     2400
gctggagttt gacctgtatg ttgctccagt gaaatggata gaacacagct gattgaatag     2460
gacaaataac tttggaggca cagccggttt cctggccgcg gacaacacca acaagcggct     2520
cgtggtcgcc ttccgaggca gtagcaccat caagaactgg attgctgatc tcgacttcat     2580
```

-continued

```
cctgcaagat aacgatgacc tctgtactgg ctgcaaggtt cacactggat tctggaaggc    2640
atgggaagcc gctgcagaca atctgacgag caagatcaag tccgcgatga gcacgtattc    2700
gggctatacc ctctacttca ccgggcacag cttgggcggc gcattggcta cactgggagc    2760
aacggtcttg cgaaatgacg gttatagcgt tgaactggtg agtgcttcag agggtgatca    2820
ttaaacagcc ggttctgaca gtcaatagta cacctatgga tgtcctcgag tcggaaacta    2880
tgcgctggcc gagcacatca ccagccaggg atctggagcg aacttccgcg ttacacactt    2940
gaacgacatc gtcccccggt tgccacccat ggactttgga ttcagccagc caagtccaga    3000
atactggatc accagtggca ccggagccag tgtcacggcg tcggatattg aactcatcga    3060
gggaatcaat tcgacggcgg ggaatgcagg cgaagcaacg gtggacgttt ggctcacttt    3120
gtggtacttt ttcgcaattt cagagtgtct gctatagctg acagtccga tgaaataagt     3180
gcggagagaa agtgtaaata gtaattagta tataatcagg cagagaagca gtggtggtca    3240
gagaagaaag agtgagatcc cattacgtag cagataaacc acgtgtggag gcgctgttcc    3300
tccacttgca gttgcggcca tcaatcatct tcttctcctt actttcgtcc accataactc    3360
tcatcctgcc agctgtcgca tccccgggtt caacaacag tcgcctccgg ccctccgtg     3420
gttctccttt attattccat ccgccggccg acgtttcacc ctcatcctgc gccgccgcaa    3480
ttctctccgg atcggtcaag tcactcgaac cgccgcccgc atcgacctca ccgacccgac    3540
cgtctgcgat cgcccatccg tgcagccatg ttccctgccc cgtcactctg atttgacgct    3600
caattgactt ccgtggcata catacatcca gcagcatatg atcacagctc ccccgcctcg    3660
tgccagtctc gccgccgccg ccgttgccag cc                                  3692
```

<210> SEQ ID NO 5
<211> LENGTH: 894
<212> TYPE: DNA
<213> ORGANISM: Aspergillus niger
<220> FEATURE:
<221> NAME/KEY: CDS
<222> LOCATION: (1)..(894)

<400> SEQUENCE: 5

```
atg ttc tct gga cgg ttt gga gtg ctt ttg acg gcg ctc gct gcg ctg     48
Met Phe Ser Gly Arg Phe Gly Val Leu Leu Thr Ala Leu Ala Ala Leu
1               5                   10                  15 agt gct gcg gca ccg aca cca ctt gat gtg cgg agt gtc tcg act tcc     96
Ser Ala Ala Ala Pro Thr Pro Leu Asp Val Arg Ser Val Ser Thr Ser
            20                  25                  30 acg ttg gat gag ctg caa ttg ttc tcg caa tgg tct gcc gca gct tat    144
Thr Leu Asp Glu Leu Gln Leu Phe Ser Gln Trp Ser Ala Ala Ala Tyr
        35                  40                  45 tgc tcg aac aat atc gac tcg gac gac tct aac gtg aca tgc acg gcc    192
Cys Ser Asn Asn Ile Asp Ser Asp Asp Ser Asn Val Thr Cys Thr Ala
    50                  55                  60 gac gcc tgt cca tca gtc gag gag gcg agc acc aag atg ctg ctg gag    240
Asp Ala Cys Pro Ser Val Glu Glu Ala Ser Thr Lys Met Leu Leu Glu
65                  70                  75                  80 ttt gac ctg aca aat aac ttt gga ggc aca gcc ggt ttc ctg gcc gcg    288
Phe Asp Leu Thr Asn Asn Phe Gly Gly Thr Ala Gly Phe Leu Ala Ala
                85                  90                  95 gac aac acc aac aag cgg ctc gtg gtc gcc ttc cga ggc agt agc acc    336
Asp Asn Thr Asn Lys Arg Leu Val Val Ala Phe Arg Gly Ser Ser Thr
            100                 105                 110 atc aag aac tgg att gct gat ctc gac ttc atc ctg caa gat aac gat    384
Ile Lys Asn Trp Ile Ala Asp Leu Asp Phe Ile Leu Gln Asp Asn Asp
```

-continued

```
            115                 120                 125
gac ctc tgt act ggc tgc aag gtt cac act gga ttc tgg aag gca tgg    432
Asp Leu Cys Thr Gly Cys Lys Val His Thr Gly Phe Trp Lys Ala Trp
130                 135                 140 gaa gcc gct gca gac aat ctg acg agc aag atc aag tcc gcg atg agc    480
Glu Ala Ala Ala Asp Asn Leu Thr Ser Lys Ile Lys Ser Ala Met Ser
145                 150                 155                 160 acg tat tcg ggc tat acc ctc tac ttc acc ggg cac agc ttg ggc ggc    528
Thr Tyr Ser Gly Tyr Thr Leu Tyr Phe Thr Gly His Ser Leu Gly Gly
                165                 170                 175 gca ttg gct aca ctg gga gca acg gtc ttg cga aat gac ggt tat agc    576
Ala Leu Ala Thr Leu Gly Ala Thr Val Leu Arg Asn Asp Gly Tyr Ser
            180                 185                 190 gtt gaa ctg tac acc tat gga tgt cct cga gtc gga aac tat gcg ctg    624
Val Glu Leu Tyr Thr Tyr Gly Cys Pro Arg Val Gly Asn Tyr Ala Leu
        195                 200                 205 gcc gag cac atc acc agc cag gga tct gga gcg aac ttc cgc gtt aca    672
Ala Glu His Ile Thr Ser Gln Gly Ser Gly Ala Asn Phe Arg Val Thr
210                 215                 220 cac ttg aac gac atc gtc ccc cgg ttg cca ccc atg gac ttt gga ttc    720
His Leu Asn Asp Ile Val Pro Arg Leu Pro Pro Met Asp Phe Gly Phe
225                 230                 235                 240 agc cag cca agt cca gaa tac tgg atc acc agt ggc acc gga gcc agt    768
Ser Gln Pro Ser Pro Glu Tyr Trp Ile Thr Ser Gly Thr Gly Ala Ser
                245                 250                 255 gtc acg gcg tcg gat att gaa ctc atc gag gga atc aat tcg acg gcg    816
Val Thr Ala Ser Asp Ile Glu Leu Ile Glu Gly Ile Asn Ser Thr Ala
            260                 265                 270 ggg aat gca ggc gaa gca acg gtg gac gtt ttg gct cac ttg tgg tac    864
Gly Asn Ala Gly Glu Ala Thr Val Asp Val Leu Ala His Leu Trp Tyr
        275                 280                 285 ttt ttc gca att tca gag tgt ctg cta tag                            894
Phe Phe Ala Ile Ser Glu Cys Leu Leu
290                 295

<210> SEQ ID NO 6
<211> LENGTH: 297
<212> TYPE: PRT
<213> ORGANISM: Aspergillus niger

<400> SEQUENCE: 6

Met Phe Ser Gly Arg Phe Gly Val Leu Leu Thr Ala Leu Ala Ala Leu
1               5                   10                  15

Ser Ala Ala Ala Pro Thr Pro Leu Asp Val Arg Ser Val Ser Thr Ser
            20                  25                  30

Thr Leu Asp Glu Leu Gln Leu Phe Ser Gln Trp Ser Ala Ala Ala Tyr
        35                  40                  45

Cys Ser Asn Asn Ile Asp Ser Asp Ser Asn Val Thr Cys Thr Ala
    50                  55                  60

Asp Ala Cys Pro Ser Val Glu Glu Ala Ser Thr Lys Met Leu Leu Glu
65                  70                  75                  80

Phe Asp Leu Thr Asn Asn Phe Gly Gly Thr Ala Gly Phe Leu Ala Ala
                85                  90                  95

Asp Asn Thr Asn Lys Arg Leu Val Val Ala Phe Arg Gly Ser Ser Thr
            100                 105                 110

Ile Lys Asn Trp Ile Ala Asp Leu Asp Phe Ile Leu Gln Asp Asn Asp
        115                 120                 125

Asp Leu Cys Thr Gly Cys Lys Val His Thr Gly Phe Trp Lys Ala Trp
```

-continued

```
            130                 135                 140
Glu Ala Ala Ala Asp Asn Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Val Gly Asn Tyr Ala Leu
        195                 200                 205

Ala Glu His Ile Thr Ser Gln Gly Ser Gly Ala Asn Phe Arg Val Thr
    210                 215                 220

His Leu Asn Asp Ile Val Pro Arg Leu Pro Pro Met Asp Phe Gly Phe
225                 230                 235                 240

Ser Gln Pro Ser Pro Glu Tyr Trp Ile Thr Ser Gly Thr Gly Ala Ser
                245                 250                 255

Val Thr Ala Ser Asp Ile Glu Leu Ile Glu Gly Ile Asn Ser Thr Ala
            260                 265                 270

Gly Asn Ala Gly Glu Ala Thr Val Asp Val Leu Ala His Leu Trp Tyr
        275                 280                 285

Phe Phe Ala Ile Ser Glu Cys Leu Leu
    290                 295
```

<210> SEQ ID NO 7
<211> LENGTH: 3478
<212> TYPE: DNA
<213> ORGANISM: Aspergillus niger

<400> SEQUENCE: 7

| | | | | | |
|---|---|---|---|---|---|
| ttgctgtata | tttggtttta | ctagaagaaa | gtttaattct | gttagttggt | gttcttgtgt | 60 |
| gctctcatgt | ggctgacttg | agaagactca | aatgttggat | gtctgtcaga | gtaagctgac | 120 |
| gttgtttccg | gcgaagtttt | cctctagttg | catagttacc | ctgctcaccc | gaagttaatt | 180 |
| gcattagacc | agaagttgga | cacgagcgaa | ccacagcaga | gctgactgca | gcaagccttt | 240 |
| gctgcgcacc | tcagccttct | ggttccgtgg | actccatccg | tcagctccgg | acccactgat | 300 |
| cgctgtgaca | tcagggtcct | tgtgtgaatg | tataccaggg | cccttgcggg | tctcttatcc | 360 |
| ctgagtagtt | gtaacgtaaa | tgccttaatg | cgttcaaagc | aaatgattca | ctcacaattg | 420 |
| gtgagtacca | catgggagtt | ttcagaatct | agcaaaaagc | ctaacaagca | gtgtgtcgcc | 480 |
| caagatcgat | cccgtgtgaa | ccatcatcca | tgttcggctt | accaacttta | atcctcagct | 540 |
| actactctct | gactgccagt | tcagctacgg | aattgccggt | ttaaatcagc | ctccacatgt | 600 |
| agtgtcccga | accatggact | gcaattcaat | gccatcttcg | cttcagaccc | tccaatcatc | 660 |
| tatcaaagat | ccatggttct | ccagaccgca | agcaacgagg | tcactatgat | caccaccaag | 720 |
| acttcggtac | cattcttaat | gcttgacaag | taatggcata | tctactaccg | aggccctcgg | 780 |
| ctgcgcagca | accttggtcg | ggttggaaat | tcgaagtggt | cgctctttct | tgctgtgaag | 840 |
| acgtcgggga | gagctgtact | tcaccatccc | aacccattgg | cttcctctag | aaaacagtag | 900 |
| ccgtatatta | cttgctagca | tgcagtgcat | agcagcttta | cttgcctttg | caagcatatt | 960 |
| gtcaggtttg | tcattgtcat | ttccagtttc | aatttcacca | ttgcacccct | tcgcagcttc | 1020 |
| cggagctggt | ctaaccgcag | agttccatag | gcgtaagtgc | tagcttcaac | aatgagtacg | 1080 |
| gcagacactt | gatgcagcag | cgcgcgctac | caaatgcgcc | tgatggatat | acaccaacta | 1140 |
| cggtcgggtg | ctctgcgagt | cgtcccactg | tgcgcagtgc | gacagcactc | tcgtcgaacg | 1200 |

-continued

```
aatcgtcatg gctaaggact cggaggaaca atacactgtc ggccatgaga gaattcttcg   1260
gtcgcgtcaa cattacagac tttgacgctg tggggtatat caatcgcatc tctagcaaca   1320
cctccgattt gccgaatatt ggcattgctg tctctggtgg agggtaccgg gctctgatga   1380
acggtgctgg ggcaatcaag gcttttgata tcgtacagt caattctaca agcaatggtc    1440
agctgggtgg actgctgcaa tcagcaacat atctggccgg cctcagtggt ggggcatggt   1500
tggtgggatc tatctacttg aataatttct ccaccatctc gtcgcttcag acctacgatc   1560
ctggtgatgt ctggcagttc cagaactcga tctttgaagg ccccgacggg gatagtatcc   1620
aaattataga ttctgcaacc tactacagag atatttatga cgcagtgtct ggaaaggatg   1680
atgcaggttg gcagacatcc atcactgatt actggtatga gtcctagccc aattctcgcc   1740
cagcagcgat actgatgccc accagggcc gcgcgctctc ataccagctc gtcaacgcca    1800
ccgccggagg aatcaactac acctggtcat ccatagctct gaccgactcc ttcaggaggg   1860
cagaaatgcc aatgcccgtg ctagtcgcag acggccgata cccagacgag ctcctagtca   1920
gcagcaatgc cacagtctac gaattcaacc cctgggaatt cggcacctt gacccaacgg    1980
tacacggctt cgtgcccgtt cagtatctgg gctcacgctt cgtagccgga tcccttccca   2040
gcaacgaaag ctgcgtccgc gggtttgaca atggcggctt tattatggga acctcatcca   2100
ccttattcaa ccaattcctt cttcaaatca acacaactag cctccccagc ttcctgaaag   2160
acgcatttac aagcatccta gaagatctcg gcgaaaacag ccaagacata gcagtttaca   2220
cccccaaccc gttctatctc tgggccaatt ccacctcccc atccgcaagc caaacagtcc   2280
tcgacctcgt ggatggcggc gaagacctcc aaaacatccc cttacatcca ctcatccagc   2340
cagagcgcca tgtggacgtc atctttgccg tggactcctc cgcagacacg cagtataact   2400
ggcccaacgg caccgcatta gtcgccacct acgagcgcag cctaaactct acgggcatcg   2460
gcaatgggac agctttccct gctatccccg accaaaatac ttttgtcaat gagggtctca   2520
atacgcgacc aacgttcttc gggtgcaact catcgaatac cactgggcca gcaccgttag   2580
ttgtttacct tcctaacttt ccgtatgtga cttttcgaa cgtgtcgacg tttgatccga    2640
gttactcgga gtcgcagagg gatagtatta tccttaatgg gtatgatgtg ccacgatgg    2700
ggaataatag tcgcgatggg gaatggtctt cttgtgttgc gtgtgctgtt ttgagtcggt   2760
cttttgaacg gactaacact acggtgccgg atcagtgtag ccggtgcttt gagaggtact   2820
gctgggatgg tactacgaat agttcgactc cgggtactta tgagcccagt acggtatttg   2880
ataatgctgg gtatgctgta atgcctgctg ttttcgcgac tacgatggct gctgcgactg   2940
tttcggcgtt tatgtaggac attttccgct gttcagggtg tatgtatagt gagattgata   3000
ggaacagaaa agtcaatgca tagtaggttt atatgaagaa agtatataat tgtgcaattc   3060
aaggcattcc atgaaatgca ggagtgattg acgtgctcga ctccggatga ggcagcccac   3120
ttccctcacg tgtcgcgtta ccaggggaac caccgcccga tcgcccaaac aagcaagcgg   3180
cacaaacagg agcgtccact cgggcgactt cgatgatcgg cctccactgc taactagtca   3240
acaaccacgc caactcgacc accaccatcc cctgcttact ttaaccctgc atacaagctt   3300
ccggggttaa agcaagtgat tgttcactta tcgccagtgg acgcacaatg agcacggcaa   3360
ttcagtactg agtccccgct gccaccgaca caccacaaca gaagcgggac atcaacaaca   3420
ccacctccga cctcccgcgc ggtagcattt accgactccg aatattgatc agcacaca    3478
```

<210> SEQ ID NO 8

<211> LENGTH: 1902
<212> TYPE: DNA
<213> ORGANISM: Aspergillus niger
<220> FEATURE:
<221> NAME/KEY: CDS
<222> LOCATION: (1)..(1902)

<400> SEQUENCE: 8

```
atg cag tgc ata gca gct tta ctt gcc ttt gca agc ata ttg tca ggc    48
Met Gln Cys Ile Ala Ala Leu Leu Ala Phe Ala Ser Ile Leu Ser Gly
1               5                   10                  15 gta agt gct agc ttc aac aat gag tac ggc aga cac ttg atg cag cag    96
Val Ser Ala Ser Phe Asn Asn Glu Tyr Gly Arg His Leu Met Gln Gln
            20                  25                  30 cgc gcg cta cca aat gcg cct gat gga tat aca cca act acg gtc ggg   144
Arg Ala Leu Pro Asn Ala Pro Asp Gly Tyr Thr Pro Thr Thr Val Gly
        35                  40                  45 tgc tct gcg agt cgt ccc act gtg cgc agt gcg aca gca ctc tcg tcg   192
Cys Ser Ala Ser Arg Pro Thr Val Arg Ser Ala Thr Ala Leu Ser Ser
50                  55                  60 aac gaa tcg tca tgg cta agg act cgg agg aac aat aca ctg tcg gcc   240
Asn Glu Ser Ser Trp Leu Arg Thr Arg Arg Asn Asn Thr Leu Ser Ala
65                  70                  75                  80 atg aga gaa ttc ttc ggt cgc gtc aac att aca gac ttt gac gct gtg   288
Met Arg Glu Phe Phe Gly Arg Val Asn Ile Thr Asp Phe Asp Ala Val
                85                  90                  95 ggg tat atc aat cgc atc tct agc aac acc tcc gat ttg ccg aat att   336
Gly Tyr Ile Asn Arg Ile Ser Ser Asn Thr Ser Asp Leu Pro Asn Ile
            100                 105                 110 ggc att gct gtc tct ggt gga ggg tac cgg gct ctg atg aac ggt gct   384
Gly Ile Ala Val Ser Gly Gly Gly Tyr Arg Ala Leu Met Asn Gly Ala
        115                 120                 125 ggg gca atc aag gct ttt gat aat cgt aca gtc aat tct aca agc aat   432
Gly Ala Ile Lys Ala Phe Asp Asn Arg Thr Val Asn Ser Thr Ser Asn
    130                 135                 140 ggt cag ctg ggt gga ctg ctg caa tca gca aca tat ctg gcc ggc ctc   480
Gly Gln Leu Gly Gly Leu Leu Gln Ser Ala Thr Tyr Leu Ala Gly Leu
145                 150                 155                 160 agt ggt ggg gca tgg ttg gtg gga tct atc tac ttg aat aat ttc tcc   528
Ser Gly Gly Ala Trp Leu Val Gly Ser Ile Tyr Leu Asn Asn Phe Ser
                165                 170                 175 acc atc tcg tcg ctt cag acc tac gat cct ggt gat gtc tgg cag ttc   576
Thr Ile Ser Ser Leu Gln Thr Tyr Asp Pro Gly Asp Val Trp Gln Phe
            180                 185                 190 cag aac tcg atc ttt gaa ggc ccc gac ggg gat agt atc caa att ata   624
Gln Asn Ser Ile Phe Glu Gly Pro Asp Gly Asp Ser Ile Gln Ile Ile
        195                 200                 205 gat tct gca acc tac tac aga gat att tat gac gca gtg tct gga aag   672
Asp Ser Ala Thr Tyr Tyr Arg Asp Ile Tyr Asp Ala Val Ser Gly Lys
    210                 215                 220 gat gat gca ggt tgg cag aca tcc atc act gat tac tgg ggc cgc gcg   720
Asp Asp Ala Gly Trp Gln Thr Ser Ile Thr Asp Tyr Trp Gly Arg Ala
225                 230                 235                 240 ctc tca tac cag ctc gtc aac gcc acc gcc gga gga atc aac tac acc   768
Leu Ser Tyr Gln Leu Val Asn Ala Thr Ala Gly Gly Ile Asn Tyr Thr
                245                 250                 255 tgg tca tcc ata gct ctg acc gac tcc ttc agg agg gca gaa atg cca   816
Trp Ser Ser Ile Ala Leu Thr Asp Ser Phe Arg Arg Ala Glu Met Pro
            260                 265                 270 atg ccc gtg cta gtc gca gac ggc cga tac cca gac gag ctc cta gtc   864
Met Pro Val Leu Val Ala Asp Gly Arg Tyr Pro Asp Glu Leu Leu Val
```

```
                275                 280                 285
agc agc aat gcc aca gtc tac gaa ttc aac ccc tgg gaa ttc ggc acc      912
Ser Ser Asn Ala Thr Val Tyr Glu Phe Asn Pro Trp Glu Phe Gly Thr
    290                 295                 300 ttt gac cca acg gta cac ggc ttc gtg ccc gtt cag tat ctg ggc tca      960
Phe Asp Pro Thr Val His Gly Phe Val Pro Val Gln Tyr Leu Gly Ser
305                 310                 315                 320 cgc ttc gta gcc gga tcc ctt ccc agc aac gaa agc tgc gtc cgc ggg     1008
Arg Phe Val Ala Gly Ser Leu Pro Ser Asn Glu Ser Cys Val Arg Gly
                325                 330                 335 ttt gac aat ggc ggc ttt att atg gga acc tca tcc acc tta ttc aac     1056
Phe Asp Asn Gly Gly Phe Ile Met Gly Thr Ser Ser Thr Leu Phe Asn
                340                 345                 350 caa ttc ctt ctt caa atc aac aca act agc ctc ccc agc ttc ctg aaa     1104
Gln Phe Leu Leu Gln Ile Asn Thr Thr Ser Leu Pro Ser Phe Leu Lys
            355                 360                 365 gac gca ttt aca agc atc cta gaa gat ctc ggc gaa aac agc caa gac     1152
Asp Ala Phe Thr Ser Ile Leu Glu Asp Leu Gly Glu Asn Ser Gln Asp
        370                 375                 380 ata gca gtt tac acc ccc aac ccg ttc tat ctc tgg gcc aat tcc acc     1200
Ile Ala Val Tyr Thr Pro Asn Pro Phe Tyr Leu Trp Ala Asn Ser Thr
385                 390                 395                 400 tcc cca tcc gca agc caa aca gtc ctc gac ctc gtg gat ggc ggc gaa     1248
Ser Pro Ser Ala Ser Gln Thr Val Leu Asp Leu Val Asp Gly Gly Glu
                405                 410                 415 gac ctc caa aac atc ccc tta cat cca ctc atc cag cca gag cgc cat     1296
Asp Leu Gln Asn Ile Pro Leu His Pro Leu Ile Gln Pro Glu Arg His
                420                 425                 430 gtg gac gtc atc ttt gcc gtg gac tcc tcc gca gac acg cag tat aac     1344
Val Asp Val Ile Phe Ala Val Asp Ser Ser Ala Asp Thr Gln Tyr Asn
                435                 440                 445 tgg ccc aac ggc acc gca tta gtc gcc acc tac gag cgc agc cta aac     1392
Trp Pro Asn Gly Thr Ala Leu Val Ala Thr Tyr Glu Arg Ser Leu Asn
        450                 455                 460 tct acg ggc atc ggc aat ggg aca gct ttc cct gct atc ccc gac caa     1440
Ser Thr Gly Ile Gly Asn Gly Thr Ala Phe Pro Ala Ile Pro Asp Gln
465                 470                 475                 480 aat act ttt gtc aat gag ggt ctc aat acg cga cca acg ttc ttc ggg     1488
Asn Thr Phe Val Asn Glu Gly Leu Asn Thr Arg Pro Thr Phe Phe Gly
                485                 490                 495 tgc aac tca tcg aat acc act ggg cca gca ccg tta gtt gtt tac ctt     1536
Cys Asn Ser Ser Asn Thr Thr Gly Pro Ala Pro Leu Val Val Tyr Leu
                500                 505                 510 cct aac ttt ccg tat gtg act ttt tcg aac gtg tcg acg ttt gat ccg     1584
Pro Asn Phe Pro Tyr Val Thr Phe Ser Asn Val Ser Thr Phe Asp Pro
            515                 520                 525 agt tac tcg gag tcg cag agg gat agt att atc ctt aat ggg tat gat     1632
Ser Tyr Ser Glu Ser Gln Arg Asp Ser Ile Ile Leu Asn Gly Tyr Asp
        530                 535                 540 gtg gcc acg atg ggg aat aat agt cgc gat ggg gaa tgg tct tct tgt     1680
Val Ala Thr Met Gly Asn Asn Ser Arg Asp Gly Glu Trp Ser Ser Cys
545                 550                 555                 560 gtt gcg tgt gct gtt ttg agt cgg tct ttt gaa cgg act aac act acg     1728
Val Ala Cys Ala Val Leu Ser Arg Ser Phe Glu Arg Thr Asn Thr Thr
                565                 570                 575 gtg ccg gat cag tgt agc cgg tgc ttt gag agg tac tgc tgg gat ggt     1776
Val Pro Asp Gln Cys Ser Arg Cys Phe Glu Arg Tyr Cys Trp Asp Gly
                580                 585                 590 act acg aat agt tcg act ccg ggt act tat gag ccc agt acg gta ttt     1824
```

```
Thr Thr Asn Ser Ser Thr Pro Gly Thr Tyr Glu Pro Ser Thr Val Phe
        595                 600                 605 gat aat gct ggg tat gct gta atg cct gct gtt ttc gcg act acg atg    1872
Asp Asn Ala Gly Tyr Ala Val Met Pro Ala Val Phe Ala Thr Thr Met
    610                 615                 620 gct gct gcg act gtt tcg gcg ttt atg tag                            1902
Ala Ala Ala Thr Val Ser Ala Phe Met
625                 630

<210> SEQ ID NO 9
<211> LENGTH: 633
<212> TYPE: PRT
<213> ORGANISM: Aspergillus niger

<400> SEQUENCE: 9

Met Gln Cys Ile Ala Ala Leu Leu Ala Phe Ala Ser Ile Leu Ser Gly
1               5                   10                  15

Val Ser Ala Ser Phe Asn Asn Glu Tyr Gly Arg His Leu Met Gln Gln
            20                  25                  30

Arg Ala Leu Pro Asn Ala Pro Asp Gly Tyr Thr Pro Thr Thr Val Gly
        35                  40                  45

Cys Ser Ala Ser Arg Pro Thr Val Arg Ser Ala Thr Ala Leu Ser Ser
    50                  55                  60

Asn Glu Ser Ser Trp Leu Arg Thr Arg Asn Asn Thr Leu Ser Ala
65                  70                  75                  80

Met Arg Glu Phe Phe Gly Arg Val Asn Ile Thr Asp Phe Asp Ala Val
                85                  90                  95

Gly Tyr Ile Asn Arg Ile Ser Ser Asn Thr Ser Asp Leu Pro Asn Ile
            100                 105                 110

Gly Ile Ala Val Ser Gly Gly Tyr Arg Ala Leu Met Asn Gly Ala
        115                 120                 125

Gly Ala Ile Lys Ala Phe Asp Asn Arg Thr Val Asn Ser Thr Ser Asn
    130                 135                 140

Gly Gln Leu Gly Gly Leu Leu Gln Ser Ala Thr Tyr Leu Ala Gly Leu
145                 150                 155                 160

Ser Gly Gly Ala Trp Leu Val Gly Ser Ile Tyr Leu Asn Asn Phe Ser
                165                 170                 175

Thr Ile Ser Ser Leu Gln Thr Tyr Asp Pro Gly Asp Val Trp Gln Phe
            180                 185                 190

Gln Asn Ser Ile Phe Glu Gly Pro Asp Gly Asp Ser Ile Gln Ile Ile
        195                 200                 205

Asp Ser Ala Thr Tyr Tyr Arg Asp Ile Tyr Asp Ala Val Ser Gly Lys
    210                 215                 220

Asp Asp Ala Gly Trp Gln Thr Ser Ile Thr Asp Tyr Trp Gly Arg Ala
225                 230                 235                 240

Leu Ser Tyr Gln Leu Val Asn Ala Thr Ala Gly Gly Ile Asn Tyr Thr
                245                 250                 255

Trp Ser Ser Ile Ala Leu Thr Asp Ser Phe Arg Arg Ala Glu Met Pro
            260                 265                 270

Met Pro Val Leu Val Ala Asp Gly Arg Tyr Pro Asp Glu Leu Leu Val
        275                 280                 285

Ser Ser Asn Ala Thr Val Tyr Glu Phe Asn Pro Trp Glu Phe Gly Thr
    290                 295                 300

Phe Asp Pro Thr Val His Gly Phe Val Pro Val Gln Tyr Leu Gly Ser
305                 310                 315                 320
```

```
Arg Phe Val Ala Gly Ser Leu Pro Asn Glu Ser Cys Val Arg Gly
            325                 330                 335

Phe Asp Asn Gly Gly Phe Ile Met Gly Thr Ser Thr Leu Phe Asn
            340                 345                 350

Gln Phe Leu Leu Gln Ile Asn Thr Thr Ser Leu Pro Ser Phe Leu Lys
            355                 360                 365

Asp Ala Phe Thr Ser Ile Leu Glu Asp Leu Gly Glu Asn Ser Gln Asp
            370                 375                 380

Ile Ala Val Tyr Thr Pro Asn Pro Phe Tyr Leu Trp Ala Asn Ser Thr
385                 390                 395                 400

Ser Pro Ser Ala Ser Gln Thr Val Leu Asp Leu Val Asp Gly Gly Glu
            405                 410                 415

Asp Leu Gln Asn Ile Pro Leu His Pro Leu Ile Gln Pro Glu Arg His
            420                 425                 430

Val Asp Val Ile Phe Ala Val Asp Ser Ser Ala Asp Thr Gln Tyr Asn
            435                 440                 445

Trp Pro Asn Gly Thr Ala Leu Val Ala Thr Tyr Glu Arg Ser Leu Asn
450                 455                 460

Ser Thr Gly Ile Gly Asn Gly Thr Ala Phe Pro Ala Ile Pro Asp Gln
465                 470                 475                 480

Asn Thr Phe Val Asn Glu Gly Leu Asn Thr Arg Pro Thr Phe Phe Gly
            485                 490                 495

Cys Asn Ser Ser Asn Thr Thr Gly Pro Ala Pro Leu Val Val Tyr Leu
            500                 505                 510

Pro Asn Phe Pro Tyr Val Thr Phe Ser Asn Val Ser Thr Phe Asp Pro
            515                 520                 525

Ser Tyr Ser Glu Ser Gln Arg Asp Ser Ile Ile Leu Asn Gly Tyr Asp
            530                 535                 540

Val Ala Thr Met Gly Asn Asn Ser Arg Asp Gly Glu Trp Ser Ser Cys
545                 550                 555                 560

Val Ala Cys Ala Val Leu Ser Arg Ser Phe Glu Arg Thr Asn Thr Thr
            565                 570                 575

Val Pro Asp Gln Cys Ser Arg Cys Phe Glu Arg Tyr Cys Trp Asp Gly
            580                 585                 590

Thr Thr Asn Ser Ser Thr Pro Gly Thr Tyr Glu Pro Ser Thr Val Phe
            595                 600                 605

Asp Asn Ala Gly Tyr Ala Val Met Pro Ala Val Phe Ala Thr Thr Met
610                 615                 620

Ala Ala Ala Thr Val Ser Ala Phe Met
625                 630
```

<210> SEQ ID NO 10
<211> LENGTH: 2292
<212> TYPE: DNA
<213> ORGANISM: Aspergillus niger

<400> SEQUENCE: 10

```
cacagctgga cagaatggct ggccttgaat gctatatgca atacaggcaa caacacctcg      60
atctgaatat agtatccaga ggcttgttta acgcatgatg tcatataatt aaatatatat     120
atataatgat cggtaccttc agccataaac accaacttca gcagcaacaa tttcaattct     180
cttgcagtcc caaaagtctc gttgcaatgc tgtcgctttt aatatcagca gcagctgcca     240
ctctcgcatc tgcccctggaa cttccccagg ttattcccc ggatcctgtc tcttgcccaa     300
caaatctttc atggatccga ccggcagttg gactcagcag agatgaagcg caatggggttg     360
```

-continued

```
aagggcggaa gaatgtcatc ctgggctcat tagacgcata tttgaaacga ctcaacctgg    420
acgacttcga cacagacgaa tacatatcgc gtctcaacaa caccagtcag accccaatca    480
tgggaatggc catcagtgga ggaggtttcg gatccgccta caccgggact ggtctaatcc    540
gtgctttgga tgaccgtctt cccgcagcca acgagcaacg taccggtgga cttctacaaa    600
gcatgaccta tctgtctggt ttgtctggag gatcctggcc cgcagtgtcc ttcccatcat    660
acaactttcc caccgcagac gagattgtcg attactggaa accggagatt gaccgattct    720
tcacggtcac gaacacctct gctgaagctg ctactggaaa ggccatcttt gaacagattg    780
ctacgaagta cctggctggc ttcgaggtag cgctaagtga ttatctagga cgaggatttg    840
cgtacgagtt cattcccgga caatccggcg gcctaaacac cacgttttcg gggatccgga    900
atctaagcaa ttttatcaat catcaaatgc cgatgcctat cattcatctg gcttcagttg    960
aaccggaaga tgcagagtac tacgaccttt tggtgccgtc atctaatgga acgattgtaa   1020
gtagtgcttc ttctcgataa actaccagct ccagctaacg cggtctagtt tgatttgact   1080
cccttcgaat tcggcgcctg ggacggagag gtgcatgcat ttacacccac tgagtggctc   1140
ggaaaccaac tatccaacgg tattcccgta aaccagagca aatgctggaa aggatttgat   1200
cgatcctcgt aagtaacagt atggcccag cctcgcacgc ttctaacttc atcccagact    1260
tgtcatcggc acctccgccg acgccttcaa cttctggtac ctcgaaagcg tctccaacgg   1320
aacccttggc caatttgcca aacgctccac cactcacgag tcctctctca ccaaacgatt   1380
gtcccaacct gccaacctga acgcactcgt tgacgccttc caagagacct ttgatctaaa   1440
cctaacccaa atctcctact cgaaattccc caacccattc accaacctat ccctctctac   1500
cggtaatacc cacaaatcct caaccctaaa cctcgtcgac ggcagcgaaa caggccaaac   1560
aatccccctc tggggccaga tccagcccgc gcgcaacgtc gacttcatca tagcctggga   1620
cgactcccaa gacgcagacc cctacagctg gaacaacggc acaaacctct acaacacgta   1680
cctcgccgcc aacgcaacag ggcttccctt tccgataatc ccaccctcca gaacaatgat   1740
gaacctgaat tacactctcc atccacaatt cttcggctgc gacgccaacc tcaccaccac   1800
aggcgacgac cgcgcaccta tcgtgctgta tatggctaat gcgccgtata gcgcatacac   1860
gaacttctcg ttctggcaga cggagacgag tcggcagcaa atgggggaga tattcgtgaa   1920 tagtttttgat attgttacgc aagcgaatgg gtcgtgggat ggggagtggg cggagtgtat   1980
ggggtgtgcg gctgtggaaa gaagtttggc gcgcgtgggc atggagagga cgaggcagtg   2040
tcagcggtgc tttgagaggt attgttggga tgggacactt gatgagaggg atcctggggt   2100
gttggatccg acgttagttt tggatccggg ggtgaagttt gggttgtgga atgctacgaa   2160
tccttattga tgctggtttt ggagttacag ggggaggctg gtctgggaag gtatagtact   2220
taggctttgt ggatgaaaga aatatgtgat atttggcaag ttcaccctat agacccatct   2280 gatcttttt tg                                                        2292
```

<210> SEQ ID NO 11
<211> LENGTH: 1863
<212> TYPE: DNA
<213> ORGANISM: Aspergillus niger
<220> FEATURE:
<221> NAME/KEY: CDS
<222> LOCATION: (1)..(1863)

<400> SEQUENCE: 11

```
atg ctg tcg ctt tta ata tca gca gca gct gcc act ctc gca tct gcc    48
```

```
    Met Leu Ser Leu Leu Ile Ser Ala Ala Ala Thr Leu Ala Ser Ala
    1               5                   10                  15 ctg gaa ctt ccc cag ggt tat tcc ccg gat cct gtc tct tgc cca aca        96
Leu Glu Leu Pro Gln Gly Tyr Ser Pro Asp Pro Val Ser Cys Pro Thr
            20                  25                  30 aat ctt tca tgg atc cga ccg gca gtt gga ctc agc aga gat gaa gcg       144
Asn Leu Ser Trp Ile Arg Pro Ala Val Gly Leu Ser Arg Asp Glu Ala
        35                  40                  45 caa tgg gtt gaa ggg cgg aag aat gtc atc ctg ggc tca tta gac gca       192
Gln Trp Val Glu Gly Arg Lys Asn Val Ile Leu Gly Ser Leu Asp Ala
50                  55                  60 tat ttg aaa cga ctc aac ctg gac gac ttc gac aca gac gaa tac ata       240
Tyr Leu Lys Arg Leu Asn Leu Asp Asp Phe Asp Thr Asp Glu Tyr Ile
65                  70                  75                  80 tcg cgt ctc aac aac acc agt cag acc cca atc atg gga atg gcc atc       288
Ser Arg Leu Asn Asn Thr Ser Gln Thr Pro Ile Met Gly Met Ala Ile
                85                  90                  95 agt gga gga ggt ttc gga tcc gcc tac acc ggg act ggt cta atc cgt       336
Ser Gly Gly Gly Phe Gly Ser Ala Tyr Thr Gly Thr Gly Leu Ile Arg
            100                 105                 110 gct ttg gat gac cgt ctt ccc gca gcc aac gag caa cgt acc ggt gga       384
Ala Leu Asp Asp Arg Leu Pro Ala Ala Asn Glu Gln Arg Thr Gly Gly
        115                 120                 125 ctt cta caa agc atg acc tat ctg tct ggt ttg tct gga gga tcc tgg       432
Leu Leu Gln Ser Met Thr Tyr Leu Ser Gly Leu Ser Gly Gly Ser Trp
130                 135                 140 ccc gca gtg tcc ttc cca tca tac aac ttt ccc acc gca gac gag att       480
Pro Ala Val Ser Phe Pro Ser Tyr Asn Phe Pro Thr Ala Asp Glu Ile
145                 150                 155                 160 gtc gat tac tgg aaa ccg gag att gac cga ttc ttc acg gtc acg aac       528
Val Asp Tyr Trp Lys Pro Glu Ile Asp Arg Phe Phe Thr Val Thr Asn
                165                 170                 175 acc tct gct gaa gct gct act gga aag gcc atc ttt gaa cag att gct       576
Thr Ser Ala Glu Ala Ala Thr Gly Lys Ala Ile Phe Glu Gln Ile Ala
            180                 185                 190 acg aag tac ctg gct ggc ttc gag gta gcg cta agt gat tat cta gga       624
Thr Lys Tyr Leu Ala Gly Phe Glu Val Ala Leu Ser Asp Tyr Leu Gly
        195                 200                 205 cga gga ttt gcg tac gag ttc att ccc gga caa tcc ggc ggc cta aac       672
Arg Gly Phe Ala Tyr Glu Phe Ile Pro Gly Gln Ser Gly Gly Leu Asn
210                 215                 220 acc acg ttt tcg ggg atc cgg aat cta agc aat ttt atc aat cat caa       720
Thr Thr Phe Ser Gly Ile Arg Asn Leu Ser Asn Phe Ile Asn His Gln
225                 230                 235                 240 atg ccg atg cct atc att cat ctg gct tca gtt gaa ccg gaa gat gca       768
Met Pro Met Pro Ile Ile His Leu Ala Ser Val Glu Pro Glu Asp Ala
                245                 250                 255 gag tac tac gac ctt ttg gtg ccg tca tct aat gga acg att ttt gat       816
Glu Tyr Tyr Asp Leu Leu Val Pro Ser Ser Asn Gly Thr Ile Phe Asp
            260                 265                 270 ttg act ccc ttc gaa ttc ggc gcc tgg gac gga gac gtg cat gca ttt       864
Leu Thr Pro Phe Glu Phe Gly Ala Trp Asp Gly Asp Val His Ala Phe
        275                 280                 285 aca ccc act gag tgg ctc gga aac caa cta tcc aac ggt att ccc gta       912
Thr Pro Thr Glu Trp Leu Gly Asn Gln Leu Ser Asn Gly Ile Pro Val
290                 295                 300 aac cag agc aaa tgc tgg aaa gga ttt gat cga tcc tca ctt gtc atc       960
Asn Gln Ser Lys Cys Trp Lys Gly Phe Asp Arg Ser Ser Leu Val Ile
305                 310                 315                 320
```

```
ggc acc tcc gcc gac gcc ttc aac ttc tgg tac ctc gaa agc gtc tcc      1008
Gly Thr Ser Ala Asp Ala Phe Asn Phe Trp Tyr Leu Glu Ser Val Ser
                325                 330                 335 aac gga acc ctt ggc caa ttt gcc aaa cgc tcc acc act cac gag tcc      1056
Asn Gly Thr Leu Gly Gln Phe Ala Lys Arg Ser Thr Thr His Glu Ser
            340                 345                 350 tct ctc acc aaa cga ttg tcc caa cct gcc aac ctg aac gca ctc gtt      1104
Ser Leu Thr Lys Arg Leu Ser Gln Pro Ala Asn Leu Asn Ala Leu Val
        355                 360                 365 gac gcc ttc caa gag acc ttt gat cta aac cta acc caa atc tcc tac      1152
Asp Ala Phe Gln Glu Thr Phe Asp Leu Asn Leu Thr Gln Ile Ser Tyr
    370                 375                 380 tcg aaa ttc ccc aac cca ttc acc aac cta tcc ctc tct acc ggt aat      1200
Ser Lys Phe Pro Asn Pro Phe Thr Asn Leu Ser Leu Ser Thr Gly Asn
385                 390                 395                 400 acc cac aaa tcc tca acc cta aac ctc gtc gac ggc agc gaa aca ggc      1248
Thr His Lys Ser Ser Thr Leu Asn Leu Val Asp Gly Ser Glu Thr Gly
                405                 410                 415 caa aca atc ccc ctc tgg ggc cag atc cag ccc gcg cgc aac gtc gac      1296
Gln Thr Ile Pro Leu Trp Gly Gln Ile Gln Pro Ala Arg Asn Val Asp
            420                 425                 430 ttc atc ata gcc tgg gac gac tcc caa gac gca gac ccc tac agc tgg      1344
Phe Ile Ile Ala Trp Asp Asp Ser Gln Asp Ala Asp Pro Tyr Ser Trp
        435                 440                 445 aac aac ggc aca aac ctc tac aac acg tac ctc gcc gcc aac gca aca      1392
Asn Asn Gly Thr Asn Leu Tyr Asn Thr Tyr Leu Ala Ala Asn Ala Thr
    450                 455                 460 ggg ctt ccc ttt ccg ata atc cca ccc tcc aga aca atg atg aac ctg      1440
Gly Leu Pro Phe Pro Ile Ile Pro Pro Ser Arg Thr Met Met Asn Leu
465                 470                 475                 480 aat tac act ctc cat cca caa ttc ttc ggc tgc gac gcc aac ctc acc      1488
Asn Tyr Thr Leu His Pro Gln Phe Phe Gly Cys Asp Ala Asn Leu Thr
                485                 490                 495 acc aca ggc gac gac cgc gca cct atc gtg ctg tat atg gct aat gcg      1536
Thr Thr Gly Asp Asp Arg Ala Pro Ile Val Leu Tyr Met Ala Asn Ala
            500                 505                 510 ccg tat agc gca tac acg aac ttc tcg ttc tgg cag acg gag acg agt      1584
Pro Tyr Ser Ala Tyr Thr Asn Phe Ser Phe Trp Gln Thr Glu Thr Ser
        515                 520                 525 cgg cag caa atg ggg gag ata ttc gtg aat agt ttt gat att gtt acg      1632
Arg Gln Gln Met Gly Glu Ile Phe Val Asn Ser Phe Asp Ile Val Thr
    530                 535                 540 caa gcg aat ggg tcg tgg gat ggg gag tgg gcg gag tgt atg ggg tgt      1680
Gln Ala Asn Gly Ser Trp Asp Gly Glu Trp Ala Glu Cys Met Gly Cys
545                 550                 555                 560 gcg gct gtg gaa aga agt ttg gcg cgc gtg ggc atg gag agg acg agg      1728
Ala Ala Val Glu Arg Ser Leu Ala Arg Val Gly Met Glu Arg Thr Arg
                565                 570                 575 cag tgt cag cgg tgc ttt gag agg tat tgt tgg gat ggg aca ctt gat      1776
Gln Cys Gln Arg Cys Phe Glu Arg Tyr Cys Trp Asp Gly Thr Leu Asp
            580                 585                 590 gag agg gat cct ggg gtg ttg gat ccg acg tta gtt ttg gat ccg ggg      1824
Glu Arg Asp Pro Gly Val Leu Asp Pro Thr Leu Val Leu Asp Pro Gly
        595                 600                 605 gtg aag ttt ggg ttg tgg aat gct acg aat cct tat tga                  1863
Val Lys Phe Gly Leu Trp Asn Ala Thr Asn Pro Tyr
    610                 615                 620

<210> SEQ ID NO 12
<211> LENGTH: 620
```

<212> TYPE: PRT
<213> ORGANISM: Aspergillus niger

<400> SEQUENCE: 12

```
Met Leu Ser Leu Leu Ile Ser Ala Ala Ala Thr Leu Ala Ser Ala
1               5                   10                  15

Leu Glu Leu Pro Gln Gly Tyr Ser Pro Asp Pro Val Ser Cys Pro Thr
                20                  25                  30

Asn Leu Ser Trp Ile Arg Pro Ala Val Gly Leu Ser Arg Asp Glu Ala
            35                  40                  45

Gln Trp Val Glu Gly Arg Lys Asn Val Ile Leu Gly Ser Leu Asp Ala
50                  55                  60

Tyr Leu Lys Arg Leu Asn Leu Asp Asp Phe Asp Thr Asp Glu Tyr Ile
65                  70                  75                  80

Ser Arg Leu Asn Asn Thr Ser Gln Thr Pro Ile Met Gly Met Ala Ile
                85                  90                  95

Ser Gly Gly Gly Phe Gly Ser Ala Tyr Thr Gly Thr Gly Leu Ile Arg
            100                 105                 110

Ala Leu Asp Asp Arg Leu Pro Ala Ala Asn Glu Gln Arg Thr Gly Gly
        115                 120                 125

Leu Leu Gln Ser Met Thr Tyr Leu Ser Gly Leu Ser Gly Gly Ser Trp
130                 135                 140

Pro Ala Val Ser Phe Pro Ser Tyr Asn Phe Pro Thr Ala Asp Glu Ile
145                 150                 155                 160

Val Asp Tyr Trp Lys Pro Glu Ile Asp Arg Phe Phe Thr Val Thr Asn
                165                 170                 175

Thr Ser Ala Glu Ala Ala Thr Gly Lys Ala Ile Phe Glu Gln Ile Ala
            180                 185                 190

Thr Lys Tyr Leu Ala Gly Phe Glu Val Ala Leu Ser Asp Tyr Leu Gly
        195                 200                 205

Arg Gly Phe Ala Tyr Glu Phe Ile Pro Gly Gln Ser Gly Gly Leu Asn
210                 215                 220

Thr Thr Phe Ser Gly Ile Arg Asn Leu Ser Asn Phe Ile Asn His Gln
225                 230                 235                 240

Met Pro Met Pro Ile Ile His Leu Ala Ser Val Glu Pro Glu Asp Ala
                245                 250                 255

Glu Tyr Tyr Asp Leu Leu Val Pro Ser Ser Asn Gly Thr Ile Phe Asp
            260                 265                 270

Leu Thr Pro Phe Glu Phe Gly Ala Trp Asp Gly Asp Val His Ala Phe
        275                 280                 285

Thr Pro Thr Glu Trp Leu Gly Asn Gln Leu Ser Asn Gly Ile Pro Val
290                 295                 300

Asn Gln Ser Lys Cys Trp Lys Gly Phe Asp Arg Ser Ser Leu Val Ile
305                 310                 315                 320

Gly Thr Ser Ala Asp Ala Phe Asn Phe Trp Tyr Leu Glu Ser Val Ser
                325                 330                 335

Asn Gly Thr Leu Gly Gln Phe Ala Lys Arg Ser Thr Thr His Glu Ser
            340                 345                 350

Ser Leu Thr Lys Arg Leu Ser Gln Pro Ala Asn Leu Asn Ala Leu Val
        355                 360                 365

Asp Ala Phe Gln Glu Thr Phe Asp Leu Asn Leu Thr Gln Ile Ser Tyr
370                 375                 380

Ser Lys Phe Pro Asn Pro Phe Asn Leu Ser Leu Ser Thr Gly Asn
385                 390                 395                 400
```

-continued

```
Thr His Lys Ser Ser Thr Leu Asn Leu Val Asp Gly Ser Glu Thr Gly
            405                 410                 415
Gln Thr Ile Pro Leu Trp Gly Gln Ile Gln Pro Ala Arg Asn Val Asp
        420                 425                 430
Phe Ile Ile Ala Trp Asp Asp Ser Gln Asp Ala Asp Pro Tyr Ser Trp
    435                 440                 445
Asn Asn Gly Thr Asn Leu Tyr Asn Thr Tyr Leu Ala Ala Asn Ala Thr
450                 455                 460
Gly Leu Pro Phe Pro Ile Ile Pro Pro Ser Arg Thr Met Met Asn Leu
465                 470                 475                 480
Asn Tyr Thr Leu His Pro Gln Phe Phe Gly Cys Asp Ala Asn Leu Thr
                485                 490                 495
Thr Thr Gly Asp Asp Arg Ala Pro Ile Val Leu Tyr Met Ala Asn Ala
            500                 505                 510
Pro Tyr Ser Ala Tyr Thr Asn Phe Ser Phe Trp Gln Thr Glu Thr Ser
        515                 520                 525
Arg Gln Gln Met Gly Glu Ile Phe Val Asn Ser Phe Asp Ile Val Thr
    530                 535                 540
Gln Ala Asn Gly Ser Trp Asp Gly Glu Trp Ala Glu Cys Met Gly Cys
545                 550                 555                 560
Ala Ala Val Glu Arg Ser Leu Ala Arg Val Gly Met Glu Arg Thr Arg
                565                 570                 575
Gln Cys Gln Arg Cys Phe Glu Arg Tyr Cys Trp Asp Gly Thr Leu Asp
            580                 585                 590
Glu Arg Asp Pro Gly Val Leu Asp Pro Thr Leu Val Leu Asp Pro Gly
        595                 600                 605
Val Lys Phe Gly Leu Trp Asn Ala Thr Asn Pro Tyr
    610                 615                 620

<210> SEQ ID NO 13
<211> LENGTH: 3637
<212> TYPE: DNA
<213> ORGANISM: Aspergillus niger

<400> SEQUENCE: 13
ccggatgaaa atgagacatg gctaaggtga tcggatacaa taagattgat tgtggaggaa      60
agtcgtcgga tcattgcttg aagccagaaa gccccggact cggcagaatc tgaccgcccg     120
cgctgcagct ccaatcgtag tttttctcaat cattgacagc tccattcatt gcttctctag    180
ccattactcc tgtcacttcc agaagtattc actttgatgc ctggtgttca atgattttc     240 ctattattga atcaaatatt ttgtgctata gctataacat cgctcatatt ttcccggtag     300
gatgttaata caccacatca gtcctcccaa gtcgcttctg cacaatttca tggctaatga     360
catgagctgt catctggacc ataacatgct gcttggcaac tgtagaaata gcatccatct     420
gacttcatct cgcttcagcg tgtagtgatt ctaactgttc tcccggatgc caagtttctg     480
actgtcggta gcgaacctaa tccggtagct tttcccggcg tgaagtctgt tgctgttcct     540
acgccaataa cggctaagtc gcggccaata acttcctgct agcggatttc attcgttcat     600
atcacgcccg actagggaa atgaaccata ttagataatt ggaactggtg cagttgcctg      660
attgagggtc tccactccgg ccttgttgat gatgcaggct tggcagccag caatccggcc     720
tcgttgctcc gagaaccccg tggtttgcgc aggatatgcg atgggtgaaa tattcagtgg     780
ctgtgctgga ccattaacgt cttgtcatat ttccacccgg ggccgttgta gaggttgagt     840
```

```
tccgaaggtt tacctaaaca gtgttttcg tttgggaacg cggaagggtc taagtttcgg      900
gctgccccat agggctgagc ctatgccatt ccagttggaa ccctgactgc acaggaggat      960
actattttgg atcgcctcaa tattattctg ctgcctggca ccaccttcca atcgggtacc     1020
cccgtttcat agaccctgac tggggtttct gcactagctt agttgaacga gacacaatgc     1080
aatcacaata gggtcctcaa taatatctca ggcaccacaa actcagggcc gaggatgtct     1140
acatgctgcg ccttgcctgg cttggccctg ccacctcaga ttttgctgtg ctccatttat     1200
gcattcggag attttggtac gcaggaatca gtaagctcta atagtgtggt ccgctcgtca     1260
atttcttata aatcaccctg ggcaccctc actcccaatg cactgagtct gtgttatgct      1320
agacgtgtca cttggtgcaa cccaaagcag acatgaagtt caatgcactc ttaacgaccc     1380
tcgcggcgct gggtatatc caaggtatat ttccgatctt gaaactcatc atgcagcact      1440
aactcatgct gacccgccca taggaggcgc cgcggttcct acaaccgtcg acctcacata     1500
tgcagacata tcacctcgcg cactggataa tgcccctgat ggttataccc cgagcaatgt     1560
atcctgtcct gcaaacagac cgacgattcg cagcgcgtca accctgtcat cgaacgagac     1620
ggcatgggtg gacgtccggc gtaagcagac tgtctcagcg atgaaagacc ttttcggcca     1680
tatcaacatg agctcatttg acgctatttc gtacatcaac agccattcat caaatatcac     1740
caacataccc aacatcggta ttgccgtgtc cggcggtggc tacagagccc tgaccaacgg     1800
cgcgggagca ctcaaggcat cgacagtcg aacggaaaac tcaacccata atggacagct      1860
cggtggtctt ctgcagtcag ccacatacct gtccggtctc tccggaggtg gctggctcct     1920
gggctcaatc tacatcaaca acttcaccac cgtctccaat ctgcaaacct acaaagaggg     1980
cgaagtctgg cagttccaga attcaatcac gaaaggccca aagaccaacg gcttgcaagc     2040
ttgggataca gccaagtact accgcgatct ggccaaggtg gtcgctggca agaaggacgc     2100
gggcttcaac acttccttca cggactactg gggtcgcgca ctctcctacc agctgattaa     2160
cgcgaccgac ggaggcccag gctacacctg gtcatcgatc gctttaaccc aggacttcaa     2220
gaacggaaac atgcccatgc cgctccttgt cgccgacggc cgcaacccag gcgagaccct     2280
aatcggcagc aactcgaccg tgtatgagtt caacccctgg gaattcggca gtttgatcc      2340
gtccatcttc ggcttcgctc ccctcgaata cctcggatcc tactttgaga cggcgaagt      2400
cccatccagc cgatcctgcg tccgcggctt cgataacgca ggcttcgtca tgggaacctc     2460
ctccagtctc ttcaaccaat tcatcctgaa gctcaacacc accgacatcc catcaaccct     2520
caaaacggtc atcgccagca tcctagaaga actaggcgac cgcaacgacg catcgcccat     2580
ctactctccc aaccccttct acgggtaccg caacgcgaca gtttcatacg aaaagacccc     2640
ggacctgaac gtcgtcgacg gtggcgaaga caaacagaac ctcccccctcc atcctctcat    2700
ccaacccgcc cgcaacgtgg acgtcatctt cgccgtcgac tcctcagcca gtacctcgga    2760
caactggccc aacggaagtc ctctcgtcgc gacttacgaa cgtagtctca actcaaccgg     2820
tatcggaaac ggcaccgcgt tccctagcat cccggacaag agcaccttca ttaacctggg     2880
cttgaacacc cgtccgactt tcttcggctg caatagttcc aatatcacag gccatgcacc     2940
cctggttgtc tacctcccca actaccccta cacaaccctc tccaacaagt cgaccttcca     3000
gctcaagtac gagatcttgg agcgtgatga gatgatcacc aatggctgga acgtggttac     3060
tatgggtaat ggatcaagga agtcttacga ggattggccg acttgtgcgg gctgcgctat     3120
tctgagtcgc tcgtttgatc ggactaatac ccaggtgccg gatatgtgct cgcagtgttt     3180
tgacaagtat tgctgggatg gaacgaggaa tagtacgacg ccggcggcgt atgagccgaa     3240
```

```
ggtattgatg gctagtgcgg gtgtgagggg tatttcgatg tcgaggttgg ttttgggtct    3300 cttttccggtg gtggttgggg tttggatgat gtgagtggag gttgggatct gaatgttggg    3360
atgtgtatgc taggtgatct tatgagaatg agtttacgac agtcctgata tacttcagaa    3420
gtagatccag taaagatgtg ttacttacat agaaagcagg aatggattgg atgtaatgct    3480
tattcagtta gacgtaaaag gaactcaagt ccaatactac tgcggtacag catcaccacc    3540
aaatcccact gacatccaat aaatcaagtg caaaactcct tctttctcat ccctctccag    3600
ttgatctccc tggaagtttc cttcataaga aacgcat                            3637
```

<210> SEQ ID NO 14
<211> LENGTH: 1923
<212> TYPE: DNA
<213> ORGANISM: Aspergillus niger
<220> FEATURE:
<221> NAME/KEY: CDS
<222> LOCATION: (1)..(1923)

<400> SEQUENCE: 14

```
atg aag ttc aat gca ctc tta acg acc ctc gcg gcg ctg ggg tat atc      48
Met Lys Phe Asn Ala Leu Leu Thr Thr Leu Ala Ala Leu Gly Tyr Ile
1               5                   10                  15 caa gga ggc gcc gcg gtt cct aca acc gtc gac ctc aca tat gca gac     96
Gln Gly Gly Ala Ala Val Pro Thr Thr Val Asp Leu Thr Tyr Ala Asp
            20                  25                  30 ata tca cct cgc gca ctg gat aat gcc cct gat ggt tat acc ccg agc    144
Ile Ser Pro Arg Ala Leu Asp Asn Ala Pro Asp Gly Tyr Thr Pro Ser
        35                  40                  45 aat gta tcc tgt cct gca aac aga ccg acg att cgc agc gcg tca acc    192
Asn Val Ser Cys Pro Ala Asn Arg Pro Thr Ile Arg Ser Ala Ser Thr
    50                  55                  60 ctg tca tcg aac gag acg gca tgg gtg gac gtc cgg cgt aag cag act    240
Leu Ser Ser Asn Glu Thr Ala Trp Val Asp Val Arg Arg Lys Gln Thr
65                  70                  75                  80 gtc tca gcg atg aaa gac ctt ttc ggc cat atc aac atg agc tca ttt    288
Val Ser Ala Met Lys Asp Leu Phe Gly His Ile Asn Met Ser Ser Phe
                85                  90                  95 gac gct att tcg tac atc aac agc cat tca tca aat atc acc aac ata    336
Asp Ala Ile Ser Tyr Ile Asn Ser His Ser Ser Asn Ile Thr Asn Ile
            100                 105                 110 ccc aac atc ggt att gcc gtg tcc ggc ggt ggc tac aga gcc ctg acc    384
Pro Asn Ile Gly Ile Ala Val Ser Gly Gly Gly Tyr Arg Ala Leu Thr
        115                 120                 125 aac ggc gcg gga gca ctc aag gca ttc gac agt cga acg gaa aac tca    432
Asn Gly Ala Gly Ala Leu Lys Ala Phe Asp Ser Arg Thr Glu Asn Ser
    130                 135                 140 acc cat aat gga cag ctc ggt ggt ctt ctg cag tca gcc aca tac ctg    480
Thr His Asn Gly Gln Leu Gly Gly Leu Leu Gln Ser Ala Thr Tyr Leu
145                 150                 155                 160 tcc ggt ctc tcc gga ggt ggc tgg ctc ctg ggc tca atc tac atc aac    528
Ser Gly Leu Ser Gly Gly Gly Trp Leu Leu Gly Ser Ile Tyr Ile Asn
                165                 170                 175 aac ttc acc acc gtc tcc aat ctg caa acc tac aaa gag ggc gaa gtc    576
Asn Phe Thr Thr Val Ser Asn Leu Gln Thr Tyr Lys Glu Gly Glu Val
            180                 185                 190 tgg cag ttc cag aat tca atc acg aaa ggc cca aag acc aac ggc ttg    624
Trp Gln Phe Gln Asn Ser Ile Thr Lys Gly Pro Lys Thr Asn Gly Leu
        195                 200                 205 caa gct tgg gat aca gcc aag tac tac cgc gat ctg gcc aag gtg gtc    672
```

```
                    Gln Ala Trp Asp Thr Ala Lys Tyr Tyr Arg Asp Leu Ala Lys Val Val
                        210                 215                 220 gct ggc aag aag gac gcg ggc ttc aac act tcc ttc acg gac tac tgg         720
Ala Gly Lys Lys Asp Ala Gly Phe Asn Thr Ser Phe Thr Asp Tyr Trp
225                 230                 235                 240 ggt cgc gca ctc tcc tac cag ctg att aac gcg acc gac gga ggc cca         768
Gly Arg Ala Leu Ser Tyr Gln Leu Ile Asn Ala Thr Asp Gly Gly Pro
                245                 250                 255 ggc tac acc tgg tca tcg atc gct tta acc cag gac ttc aag aac gga         816
Gly Tyr Thr Trp Ser Ser Ile Ala Leu Thr Gln Asp Phe Lys Asn Gly
                260                 265                 270 aac atg ccc atg ccg ctc ctt gtc gcc gac ggc cgc aac cca ggc gag         864
Asn Met Pro Met Pro Leu Leu Val Ala Asp Gly Arg Asn Pro Gly Glu
                275                 280                 285 acc cta atc ggc agc aac tcg acc gtg tat gag ttc aac ccc tgg gaa         912
Thr Leu Ile Gly Ser Asn Ser Thr Val Tyr Glu Phe Asn Pro Trp Glu
290                 295                 300 ttc ggc agt ttt gat ccg tcc atc ttc ggc ttc gct ccc ctc gaa tac         960
Phe Gly Ser Phe Asp Pro Ser Ile Phe Gly Phe Ala Pro Leu Glu Tyr
305                 310                 315                 320 ctc gga tcc tac ttt gag aac ggc gaa gtc cca tcc agc cga tcc tgc        1008
Leu Gly Ser Tyr Phe Glu Asn Gly Glu Val Pro Ser Ser Arg Ser Cys
                325                 330                 335 gtc cgc ggc ttc gat aac gca ggc ttc gtc atg gga acc tcc tcc agt        1056
Val Arg Gly Phe Asp Asn Ala Gly Phe Val Met Gly Thr Ser Ser Ser
                340                 345                 350 ctc ttc aac caa ttc atc ctg aag ctc aac acc acc gac atc cca tca        1104
Leu Phe Asn Gln Phe Ile Leu Lys Leu Asn Thr Thr Asp Ile Pro Ser
                355                 360                 365 acc ctc aaa acg gtc atc gcc agc atc cta gaa gaa cta ggc gac cgc        1152
Thr Leu Lys Thr Val Ile Ala Ser Ile Leu Glu Glu Leu Gly Asp Arg
370                 375                 380 aac gac gac atc gcc atc tac tct ccc aac ccc ttc tac ggg tac cgc        1200
Asn Asp Asp Ile Ala Ile Tyr Ser Pro Asn Pro Phe Tyr Gly Tyr Arg
385                 390                 395                 400 aac gcg aca gtt tca tac gaa aag acc ccg gac ctg aac gtc gtc gac        1248
Asn Ala Thr Val Ser Tyr Glu Lys Thr Pro Asp Leu Asn Val Val Asp
                405                 410                 415 ggt ggc gaa gac aaa cag aac ctc ccc ctc cat cct ctc atc caa ccc        1296
Gly Gly Glu Asp Lys Gln Asn Leu Pro Leu His Pro Leu Ile Gln Pro
                420                 425                 430 gcc cgc aac gtg gac gtc atc ttc gcc gtc gac tcc tca gcc agt acc        1344
Ala Arg Asn Val Asp Val Ile Phe Ala Val Asp Ser Ser Ala Ser Thr
                435                 440                 445 tcg gac aac tgg ccc aac gga agt cct ctc gtc gcg act tac gaa cgt        1392
Ser Asp Asn Trp Pro Asn Gly Ser Pro Leu Val Ala Thr Tyr Glu Arg
450                 455                 460 agt ctc aac tca acc ggt atc gga aac ggc acc gcg ttc cct agc atc        1440
Ser Leu Asn Ser Thr Gly Ile Gly Asn Gly Thr Ala Phe Pro Ser Ile
465                 470                 475                 480 ccg gac aag agc acc ttc att aac ctg ggc ttg aac acc cgt ccg act        1488
Pro Asp Lys Ser Thr Phe Ile Asn Leu Gly Leu Asn Thr Arg Pro Thr
                485                 490                 495 ttc ttc ggc tgc aat agt tcc aat atc aca ggc cat gca ccc ctg gtt        1536
Phe Phe Gly Cys Asn Ser Ser Asn Ile Thr Gly His Ala Pro Leu Val
                500                 505                 510 gtc tac ctc ccc aac tac ccc tac aca acc ctc tcc aac aag tcg acc        1584
Val Tyr Leu Pro Asn Tyr Pro Tyr Thr Thr Leu Ser Asn Lys Ser Thr
                515                 520                 525
```

```
ttc cag ctc aag tac gag atc ttg gag cgt gat gag atg atc acc aat    1632
Phe Gln Leu Lys Tyr Glu Ile Leu Glu Arg Asp Glu Met Ile Thr Asn
    530                 535                 540 ggc tgg aac gtg gtt act atg ggt aat gga tca agg aag tct tac gag    1680
Gly Trp Asn Val Val Thr Met Gly Asn Gly Ser Arg Lys Ser Tyr Glu
545                 550                 555                 560 gat tgg ccg act tgt gcg ggc tgc gct att ctg agt cgc tcg ttt gat    1728
Asp Trp Pro Thr Cys Ala Gly Cys Ala Ile Leu Ser Arg Ser Phe Asp
                565                 570                 575 cgg act aat acc cag gtg ccg gat atg tgc tcg cag tgt ttt gac aag    1776
Arg Thr Asn Thr Gln Val Pro Asp Met Cys Ser Gln Cys Phe Asp Lys
            580                 585                 590 tat tgc tgg gat gga acg agg aat agt acg acg ccg gcg gcg tat gag    1824
Tyr Cys Trp Asp Gly Thr Arg Asn Ser Thr Thr Pro Ala Ala Tyr Glu
        595                 600                 605 ccg aag gta ttg atg gct agt gcg ggt gtg agg ggt att tcg atg tcg    1872
Pro Lys Val Leu Met Ala Ser Ala Gly Val Arg Gly Ile Ser Met Ser
    610                 615                 620 agg ttg gtt ttg ggt ctc ttt ccg gtg gtg gtt ggg gtt tgg atg atg    1920
Arg Leu Val Leu Gly Leu Phe Pro Val Val Val Gly Val Trp Met Met
625                 630                 635                 640 tga                                                                1923

<210> SEQ ID NO 15
<211> LENGTH: 640
<212> TYPE: PRT
<213> ORGANISM: Aspergillus niger

<400> SEQUENCE: 15

Met Lys Phe Asn Ala Leu Leu Thr Thr Leu Ala Ala Leu Gly Tyr Ile
1               5                   10                  15

Gln Gly Gly Ala Ala Val Pro Thr Thr Val Asp Leu Thr Tyr Ala Asp
                20                  25                  30

Ile Ser Pro Arg Ala Leu Asp Asn Ala Pro Asp Gly Tyr Thr Pro Ser
            35                  40                  45

Asn Val Ser Cys Pro Ala Asn Arg Pro Thr Ile Arg Ser Ala Ser Thr
        50                  55                  60

Leu Ser Ser Asn Glu Thr Ala Trp Val Asp Val Arg Arg Lys Gln Thr
65                  70                  75                  80

Val Ser Ala Met Lys Asp Leu Phe Gly His Ile Asn Met Ser Ser Phe
                85                  90                  95

Asp Ala Ile Ser Tyr Ile Asn Ser His Ser Ser Asn Ile Thr Asn Ile
            100                 105                 110

Pro Asn Ile Gly Ile Ala Val Ser Gly Gly Tyr Arg Ala Leu Thr
        115                 120                 125

Asn Gly Ala Gly Ala Leu Lys Ala Phe Asp Ser Arg Thr Glu Asn Ser
130                 135                 140

Thr His Asn Gly Gln Leu Gly Gly Leu Leu Gln Ser Ala Thr Tyr Leu
145                 150                 155                 160

Ser Gly Leu Ser Gly Gly Gly Trp Leu Leu Gly Ser Ile Tyr Ile Asn
                165                 170                 175

Asn Phe Thr Thr Val Ser Asn Leu Gln Thr Tyr Lys Glu Gly Glu Val
            180                 185                 190

Trp Gln Phe Gln Asn Ser Ile Thr Lys Gly Pro Lys Thr Asn Gly Leu
        195                 200                 205

Gln Ala Trp Asp Thr Ala Lys Tyr Tyr Arg Asp Leu Ala Lys Val Val
    210                 215                 220
```

-continued

```
Ala Gly Lys Lys Asp Ala Gly Phe Asn Thr Ser Phe Thr Asp Tyr Trp
225                 230                 235                 240

Gly Arg Ala Leu Ser Tyr Gln Leu Ile Asn Ala Thr Asp Gly Gly Pro
            245                 250                 255

Gly Tyr Thr Trp Ser Ser Ile Ala Leu Thr Gln Asp Phe Lys Asn Gly
            260                 265                 270

Asn Met Pro Met Pro Leu Leu Val Ala Asp Gly Arg Asn Pro Gly Glu
            275                 280                 285

Thr Leu Ile Gly Ser Asn Ser Thr Val Tyr Glu Phe Asn Pro Trp Glu
290                 295                 300

Phe Gly Ser Phe Asp Pro Ser Ile Phe Gly Phe Ala Pro Leu Glu Tyr
305                 310                 315                 320

Leu Gly Ser Tyr Phe Glu Asn Gly Glu Val Pro Ser Arg Ser Cys
            325                 330                 335

Val Arg Gly Phe Asp Asn Ala Gly Phe Val Met Gly Thr Ser Ser Ser
            340                 345                 350

Leu Phe Asn Gln Phe Ile Leu Lys Leu Asn Thr Thr Asp Ile Pro Ser
            355                 360                 365

Thr Leu Lys Thr Val Ile Ala Ser Ile Leu Glu Glu Leu Gly Asp Arg
370                 375                 380

Asn Asp Asp Ile Ala Ile Tyr Ser Pro Asn Pro Phe Tyr Gly Tyr Arg
385                 390                 395                 400

Asn Ala Thr Val Ser Tyr Glu Lys Thr Pro Asp Leu Asn Val Val Asp
            405                 410                 415

Gly Gly Glu Asp Lys Gln Asn Leu Pro Leu His Pro Leu Ile Gln Pro
            420                 425                 430

Ala Arg Asn Val Asp Val Ile Phe Ala Val Asp Ser Ser Ala Ser Thr
            435                 440                 445

Ser Asp Asn Trp Pro Asn Gly Ser Pro Leu Val Ala Thr Tyr Glu Arg
450                 455                 460

Ser Leu Asn Ser Thr Gly Ile Gly Asn Gly Thr Ala Phe Pro Ser Ile
465                 470                 475                 480

Pro Asp Lys Ser Thr Phe Ile Asn Leu Gly Leu Asn Thr Arg Pro Thr
            485                 490                 495

Phe Phe Gly Cys Asn Ser Ser Asn Ile Thr Gly His Ala Pro Leu Val
            500                 505                 510

Val Tyr Leu Pro Asn Tyr Pro Tyr Thr Thr Leu Ser Asn Lys Ser Thr
            515                 520                 525

Phe Gln Leu Lys Tyr Glu Ile Leu Glu Arg Asp Glu Met Ile Thr Asn
            530                 535                 540

Gly Trp Asn Val Val Thr Met Gly Asn Gly Ser Arg Lys Ser Tyr Glu
545                 550                 555                 560

Asp Trp Pro Thr Cys Ala Gly Cys Ala Ile Leu Ser Arg Ser Phe Asp
            565                 570                 575

Arg Thr Asn Thr Gln Val Pro Asp Met Cys Ser Gln Cys Phe Asp Lys
            580                 585                 590

Tyr Cys Trp Asp Gly Thr Arg Asn Ser Thr Thr Pro Ala Ala Tyr Glu
            595                 600                 605

Pro Lys Val Leu Met Ala Ser Ala Gly Val Arg Gly Ile Ser Met Ser
            610                 615                 620

Arg Leu Val Leu Gly Leu Phe Pro Val Val Val Gly Val Trp Met Met
625                 630                 635                 640
```

PHOSPHOLIPASES AND USES THEREOF

This application is a divisional of application Ser. No. 11/544,679, filed Oct. 10, 2006, now U.S. Pat. No. 7,588,925; which is a continuation of U.S. application Ser. No. 10/514,998, filed Nov. 19, 2004, now abandoned; which is a U.S. national stage under 35 U.S.C. 371 of Int'l Appln. No. PCT/EP03/05450, filed May 21, 2003; the contents of which are hereby incorporated by reference in this application.

FIELD OF THE INVENTION

The invention relates to newly identified polynucleotide sequences comprising genes that encode a novel phospholipase isolated from *Aspergillus niger*. The invention features the full length nucleotide sequence of the novel genes, the cDNA sequence comprising the full length coding sequence of the novel phospholipase as well as the amino acid sequence of the full-length functional protein and functional equivalents thereof. The invention also relates to methods of using these enzymes in industrial processes and methods of diagnosing fungal infections. Also included in the invention are cells transformed with a polynucleotide according to the invention and cells wherein a phospholipase according to the invention is genetically modified to enhance or reduce its activity and/or level of expression.

BACKGROUND OF THE INVENTION

Phospholipids consist of a glycerol backbone with two esterified fatty acids in an outer (sn-1) and the middle (sn-2) position, while the third hydroxyl group of the glycerol is esterified with phosphoric acid. The phosphoric acid may, in turn, be esterified to for example an amino alcohol like ethanolamine (phosphatidylethanolamine), choline (phosphatidylcholine). The third hydroxyl group may also, instead of being esterified with phosphoric acid, be bound to sugar residues such a galactose or a dimer thereof such as in digalactosyldiglyceride.

Phospholipases are defined herein as enzymes that participate in the hydrolysis of one or more bonds in the phospholipids including digalactosyldiglyceride described above.

Several types of phospholipase activity can be distinguished which hydrolyse the ester bond(s) that link the fatty acyl moieties to the glycerol backbone.

Phospholipase $A_1$ (EC 3.1.1.32) and $A_2$ (EC 3.1.1.4) catalyse the deacylation of one fatty acyl group in the sn-1 and sn-2 positions respectively, from a diacylglycerophospholipid to produce a lysophospholipid.

Lysophospholipase (EC 3.1.1.5—also called phospholipase B by the Nomenclature Committee of the International Union of Biochemistry and Molecular Biology (Enzyme Nomenclature, Academic Press, New York, 1992)) catalyses the hydrolysis of the remaining fatty acyl group in a lysophospholipid. A phospholipase B has been reported from *Penicillium notatum* (Saito et al., 1991, Methods in Enzymology 197:446-456), which catalyses the deacylation of both fatty acids from a diacylglycerophospholipid and intrinsically possesses lysophospholipase activity.

Galactolipase (EC 3.1.4.3) catalyses the hydrolysis of one or both fatty acyl group in the sn-1 and sn-2 positions respectively, from a digalactosyldiglyceride.

Phospholipase C (EC 3.1.4.3) hydrolyses the phosphate ester bond between the glycerol backbone and the phosphate group, for example:

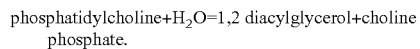
phosphatidylcholine+$H_2O$=1,2 diacylglycerol+choline phosphate.

Phospholipase D (EC 3.1.4.4) hydrolyses the phosphate ester bond between the phosphate group and the amine alcohol, for example: phosphatidylcholine+$H_2O$=choline+phosphatidic acid.

Phospholipases may conveniently be produced in microorganisms. Microbial phospholipases are available from a variety of sources; *Bacillus* species are a common source of bacterial enzymes, whereas fungal enzymes are commonly produced in *Aspergillus* species.

Fungal enzymes with phospholipase activity have been reported from various sources, including *Cryptococcus neoformans* (Chen et al, 1997, Infection and Immunity 65:405-411), *Fusobacterium necrophorum* (Fifis et al, 1996, Veterinary Microbiology 49:219-233), *Penicillium notatum* (also known as *Penicillium chrysogenum*; Kawasaki, 1975, Journal of Biochemistry 77:1233-1244; Masuda et al., 1991, European Journal of Biochemistry 202:783-787), *Penicillium cyclopium* (Mustranta et al, 1995, Process Biochemistry 30:393-401), *Saccharomyces cerevisiae* (Ichimasa et al, 1985, Agric. Biol. Chem. 49:1083-1089; Paultauf et al., 1994, J. Biol. Chem. 269:19725-19730), *Torulaspora delbrueckii* (old name *Saccharomyces rosei*, Kuwabara, 1988, Agric. Biol. Chem. 52:2451-2458; Watanabe et al, 1994, REMS Microbiological Letters 124:29-34), *Neurospora crassa* (Chakravarti et al, 1981, Archives of Biochemistry and Biophysics 206 :393-402), *Aspergillus niger* (Technical Bulletin, G-zyme™ G6999, Enzyme Bio-Systems Ltd.; Mustranta et al., 1995, supra), *Corticium centrifugum* (Uehara et al, 1979, Agric. Biol. Chem. 43:517-525), *Fusarium oxysporum* (WO 98/26057), and *Fusarium solani* (Tsung-Che et al., 1968, Phytopathological Notes 58:1437-38).

Fungal phospholipase genes have been cloned from several sources including *Penicillum notatum* (Masuda et al., 1991, supra), *Torulaspora delbrueckii* (Watanabe et al., 1994, FEMS Microbiology Letters 124: 29-34), *Saccharomyces cerevisiae* (Lee at al., 1994, Journal of Biological Chemistry 269: 19725-19730), *Aspergillus* (JP 10155493), *Neurospora crassa* (EMBL 042791), and *Schizosaccharomyces pombe* (EMBL O13857).

Phospholipases may be used in a manifold of industrial applications, including for the modification of phospholipid emulsifiers. An example of a phospholipid emulsifier is lecithin, which is a mixture of both polar and neutral lipids in which the content of polar lipids is at least 60%. Phospholipid emulsifiers have many food and non-food applications, for example egg-lecithin is used as an emulsifier in for example dairy products, specifically mayonnaise, dressings, pastry, etc., soya lecithin for example, is for example used as an emulsifier in (low calorie) sauces, bread, margarine, cosmetics etc, other lecithins are used in for example chocolates, calf feed. Modification of phospholipid emulsifiers by phospholipases may cause an increased emulsification of the oil/water mixture. Modification of phospholipid emulsifiers by phospholipases may increase the stability of the emulsions resulting from the addition of the modified phospholipid emulsifiers for a wider or different pH and/or temperature range. Modification of phospholipid emulsifiers by phospholipases may increase the stability of the emulsions, resulting from the addition of modified phospholipid emulsifiers, in the presence of $Ca^{2+}$ or $Mg^{2+}$ ions.

Another example of industrial application of phospholipases is that they can be used for the degumming of vegetable oils in the processing of these oils. In a typical degumming process, lecithins are removed from vegetable oils, for example soy oils, rapeseed (canola) oils, linseed oils, sunflower oils, to increase among others the stability of the vegetable oil, by washing the oil phase with water, wherein mixing of the water and oil under high shear conditions forces the bulk of the lecithins into the aqueous phase, which is subsequently removed in a separator. In this so-called water degumming phase, only the rapidly hydratable phospholipids are readily removed, for example phosphatidylcholine, phosphatidylinositol and phosphatidylethanolamine. The non-hydratable phopholipids/phosphatides, mostly the phospholipids, which consist of up to 50% of magnesium and/or calcium salts cannot readily be removed in the water degumming step. Exposure of the non-hydratable phopholipids/phosphatides to Phospholipase $A_2$ makes these phospholipids more soluble in water and therefore easier to extract in a water degumming phase. Another example of industrial application of phospholipases is that they are used to remove the precipitate that occurs during the saccharification (with the aid of α-amylase and glucoamylase) of wheat gluten or wheat starch to produce glucose syrups. The removal of the precipitate considerably speeds up the subsequent filtration of the resulting glucose syrups. The above-mentioned industrial applications of the phospholipase enzyme are only a few examples and this listing is not meant to be restrictive.

Yet another example of an industrial application of phospholipases in food is that phospholipases are particularly useful in baking applications to improve dough or baked product quality. Wheat flour contains approximately 2.2-2.9% lipids. The flour lipids can be divided into starch lipids (0.8-0.9%) and non-starch lipids (1.4-2.0%). Whereas the starch lipids consist mainly of polar lysophospholipids, the non-starch lipids consist of about 40% neutral triglycerides and 40% polar phospho- and glycolipids. For optimisation of the flour lipids fraction it is possible to hydrolyse the phospholipids in situ in the dough by adding phospholipase A.

For example EP-A-109244 and WO98/26057 describe this use of phospholipase A in breadmaking. In Czechoslovakian patent AO 190 264 phosphatidic acid (product of phospholipase D hydrolysis) is applied as dough and bread improving agent. In EP-A-075463 the combination of phospholipase A and phospholipase D is applied to produce lysophosphatidic acid as a dough-conditioning agent.

WO 00/32758 describes the production of lipolytic enzyme variants by making alterations to the amino acid sequence of the lipolytic enzyme so as to increase the level of desired activity. For baking applications the variant from the lipolytic enzyme of Humicula family or the Zygomycetes family was found to be particularly useful because it appeared to have phospholipase and/or digalactosyldiglyceride activity. WO 98/45453 describes a polypeptide having lipase activity derivable from *Aspergillus tubigensis* which is also showing high hydrolytic activity on digalactosyidiglyceride. These enzymes, however, suffer from a relatively low specific activity.

In the above processes, it is advantageous to use phospholipases that are obtained by recombinant DNA techniques. Such recombinant enzymes have a number of advantages over their traditionally purified counterparts. Recombinant enzymes may be produced at a low cost price, high yield, free from contaminating agents like bacteria or viruses but also free from bacterial toxins or contaminating other enzyme activities.

The present invention addresses at least one if not all of the above problems.

OBJECT OF THE INVENTION

It is an object of the invention to provide novel polynucleotides encoding novel phospholipases with improved properties. A further object is to provide naturally and recombinantly produced phospholipases as well as recombinant strains producing these. Also fusion polypeptides are part of the invention as well as methods of making and using the polynucleotides and polypeptides according to the invention. More in particular, it is an object of the present invention to provide a phospholipase also having galactolipase activity.

It is also an object of the invention to provide novel phospholipases, which solve at least one of the above-mentioned problems or to provide novel phospholipases, which have one or more improved properties if used in dough and/or baked products, selected from the group of increased strength of the dough, increased elasticity of the dough, increased stability of the dough, reduced stickiness of the dough, improved extensibility of the dough, improved machineability of the dough, increased volume of the baked product, improved crumb structure of the baked product, improved softness of the baked product, improved flavour of the baked product, improved anti-staling of the baked product, improved colour of the baked product, improved crust of the baked product or which have a broad substrate specificity.

SUMMARY OF THE INVENTION

The invention provides for novel polynucleotides encoding novel phospholipases. More in particular, the invention provides for polynucleotides having a nucleotide sequence that hybridises preferably under highly stringent conditions to a sequence that is selected from the group consisting of SEQ ID NO: 1, 2, 4, 5, 7, 8, 10, 11, 13 and 14. Consequently, the invention provides nucleic acids that are more than 40% such as about 60%, preferably 65%, more preferably 70%, even more preferably 75%, 80%, 85%, 90%, 95%, 96%, 97%, 98% or 99% homologous to one or more sequences selected from the group consisting of SEQ ID NO: 1, 2, 4, 5, 7, 8, 10, 11, 13 and 14.

In a more preferred embodiment the invention provides for such an isolated polynucleotide obtainable from a filamentous fungus, in particular *Aspergillus niger* is preferred.

In one embodiment, the invention provides for an isolated polynucleotide comprising a nucleic acid sequence encoding a polypeptide with an amino acid sequence selected from the group consisting of SEQ ID NO: 3, 6, 9, 12 and 15 or functional equivalents thereof.

In a further preferred embodiment, the invention provides an isolated polynucleotide encoding at least one functional domain of a polypeptide with an amino acid sequence selected from the group consisting of SEQ ID NO: 3, 6, 9, 12 and 15 or functional equivalents thereof.

In a preferred embodiment the invention provides a phospholipase gene with a nucleotide sequence selected from the group consisting of SEQ ID NO: 1, 4, 7, 10 and 13. In another aspect the invention provides a polynucleotide, preferably a cDNA encoding an *Aspergillus niger* phospholipase whose amino acid sequence is selected from the group consisting of SEQ ID NO: 3, 6, 9, 12 and 15, or variants or fragments of that polypeptide. In a preferred embodiment the cDNA has a sequence selected from the group consisting of SEQ ID NO: 2, 5, 8, 11 and 14, or functional equivalents thereof.

In an even further preferred embodiment, the invention provides for a polynucleotide comprising the coding sequence of the polypeptides according to the invention, preferred are the polynucleotide sequences selected from the group consisting of SEQ ID NO: 2, 5, 8, 11 and 14.

The invention also relates to vectors comprising a polynucleotide sequence according to the invention and primers, probes and fragments that may be used to amplify or detect the DNA according to the invention.

In a further preferred embodiment, a vector is provided wherein the polynucleotide sequence according to the invention is functionally linked with regulatory sequences suitable for expression of the encoded amino acid sequence in a suitable host cell, such as *Aspergillus niger* or *A. oryzea*. The invention also provides methods for preparing polynucleotides and vectors according to the invention.

The invention also relates to recombinantly produced host cells that contain heterologous or homologous polynucleotides according to the invention.

In another embodiment, the invention provides recombinant host cells wherein the expression of a phospholipase according to the invention is significantly increased or wherein the activity of the phospholipase is increased.

In another embodiment the invention provides for a recombinantly produced host cell that contains heterologous or homologous polynucleotides according to the invention and wherein the cell is capable of producing a functional phospholipase according to the invention, preferably a cell capable of over-expressing the phospholipase according to the invention, for example an *Aspergillus* strain comprising an increased copy number of a gene or cDNA according to the invention.

In yet another aspect of the invention, a purified polypeptide is provided. The polypeptides according to the invention include the polypeptides encoded by the polynucleotides according to the invention. Especially preferred is a polypeptide having an amino acid sequence selected from the group consisting of SEQ ID NO:3, 6, 9, 12 and 15 or functional equivalents thereof.

Fusion proteins comprising a polypeptide according to the invention are also within the scope of the invention. The invention also provides methods of making the polypeptides according to the invention.

The invention also relates to the use of the phospholipase according to the invention in any industrial process as described herein

DETAILED DESCRIPTION OF THE INVENTION

Polynucleotides

The present invention provides polynucleotides encoding phospholipases, having an amino acid sequence selected from the group consisting of SEQ ID NO: 3, 6, 9, 12 and 15 or a functional equivalent sequence thereof. The sequences of the five genes encoding the phospholipases PLP03, PLP06, PLP15, PLP26 and PLP34 respectively were determined by sequencing the corresponding genomic clones obtained from *Aspergillus niger*. The invention provides polynucleotide sequences comprising the genes encoding the PLP03 and PLP06 and PLP15 and PLP26 and PLP34 phospholipases respectively as well as their complete cDNA sequence and their coding sequence. Accordingly, the invention relates to an isolated polynucleotide comprising the nucleotide sequence selected from the group consisting of SEQ ID NO:1, 2, 4, 5, 7, 8, 10, 11, 13 and 14 or functional equivalents thereof.

More in particular, the invention relates to an isolated polynucleotide hybridisable under stringent conditions, preferably under highly stringent conditions, to a polynucleotide comprising the nucleotide sequence selected from the group consisting of SEQ ID NO: 1, 2, 4, 5, 7, 8, 10, 11, 13 and 14 or functional equivalents thereof.

Advantageously, such polynucleotides may be obtained from filamentous fungi, in particular from *Aspergillus niger*. More specifically, the invention relates to an isolated polynucleotide having a nucleotide sequence selected from the group consisting of SEQ ID NO:1, 2, 4, 5, 7, 8, 10, 11, 13 and 14.

The invention also relates to an isolated polynucleotide encoding at least one functional domain of a polypeptide having an amino acid sequence selected from the group of SEQ ID NO:3, 6, 9, 12, and 15 or functional equivalents.

As used herein, the terms "gene" and "recombinant gene" refer to nucleic acid molecules which may be isolated from chromosomal DNA, which include an open reading frame encoding a protein, e.g. an *Aspergillus niger* phospholipase. A gene may include coding sequences, non-coding sequences, introns and regulatory sequences. Moreover, a gene refers to an isolated nucleic acid molecule as defined herein.

A nucleic acid molecule of the present invention, such as a nucleic acid molecule having the nucleotide sequence selected from the group consisting of SEQ ID NO: 1, 2, 4, 5, 7, 8, 10, 11, 13 and 14 or a functional equivalent thereof, can be isolated using standard molecular biology techniques and the sequence information provided herein. For example, using all or a portion of the nucleic acid sequence selected from the group consisting of SEQ ID NO: 1, 2, 4, 5, 7, 8, 10, 11, 13 and 14 as a hybridization probe, nucleic acid molecules according to the invention can be isolated using standard hybridization and cloning techniques (e.g., as described in Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N.Y., 1989).

Moreover, a nucleic acid molecule encompassing all or a portion of the nucleic acid sequence selected from the group consisting of SEQ ID NO: 1, 2, 4, 5, 7, 8, 10, 11, 13 and 14 can be isolated by the polymerase chain reaction (PCR) using synthetic oligonucleotide primers designed based upon the sequence information contained in the group consisting of SEQ ID NO: 1, 2, 4, 5, 7, 8, 10, 11, 13 and 14.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Furthermore, oligonucleotides corresponding to or hybridisable to nucleotide sequences according to the invention can be prepared by standard synthetic techniques, e.g., using an automated DNA synthesizer.

In one preferred embodiment, an isolated nucleic acid molecule of the invention comprises the nucleotide sequence shown in SEQ ID NO: 2. The sequence of SEQ ID NO:2 corresponds to the coding region of the *Aspergillus niger* PLP03 phospholipase gene provided in SEQ ID NO:1. This cDNA comprises the sequence encoding the *Aspergillus niger* PLP03 polypeptide according to SEQ ID NO:3.

In a second preferred embodiment, an isolated nucleic acid molecule of the invention comprises the nucleotide sequence shown in SEQ ID NO:5. The sequence of SEQ ID NO:5 corresponds to the coding region of the *Aspergillus niger*

PLP06 phospholipase gene provided in SEQ ID NO:4. This cDNA comprises the sequence encoding the *Aspergillus niger* PLP06 polypeptide according to SEQ ID NO:6.

In a third preferred embodiment, an isolated nucleic acid molecule of the invention comprises the nucleotide sequence shown in SEQ ID NO:8. The sequence of SEQ ID NO:8 corresponds to the coding region of the *Aspergillus niger* PLP15 phospholipase gene provided in SEQ ID NO:7. This cDNA comprises the sequence encoding the *Aspergillus niger* PLP15 polypeptide according to SEQ ID NO:9.

In a fourth preferred embodiment, an isolated nucleic acid molecule of the invention comprises the nucleotide sequence shown in SEQ ID NO:11. The sequence of SEQ ID NO:11 corresponds to the coding region of the *Aspergillus niger* PLP26 phospholipase gene provided in SEQ ID NO:10. This cDNA comprises the sequence encoding the *Aspergillus niger* PLP26 polypeptide according to SEQ ID NO:12.

In a fifth preferred embodiment, an isolated nucleic acid molecule of the invention comprises the nucleotide sequence shown in SEQ ID NO:14 The sequence of SEQ ID NO:14 corresponds to the coding region of the *Aspergillus niger* PLP34 phospholipase gene provided in SEQ ID NO:13. This cDNA comprises the sequence encoding the *Aspergillus niger* PLP34 polypeptide according to SEQ ID NO:15.

In another preferred embodiment, an isolated nucleic acid molecule of the invention comprises a nucleic acid molecule which is a complement of the nucleotide sequence selected from the group consisting of SEQ ID NO: 1, 2, 4, 5, 7, 8, 10, 11, 13 and 14 or a functional equivalent of these nucleotide sequences.

A nucleic acid molecule that is complementary to another nucleotide sequence is one that is sufficiently complementary to the other nucleotide sequence such that it can hybridize to the other nucleotide sequence thereby forming a stable duplex.

One aspect of the invention pertains to isolated nucleic acid molecules that encode a polypeptide of the invention or a functional equivalent thereof such as a biologically active fragment or domain, as well as nucleic acid molecules sufficient for use as hybridisation probes to identify nucleic acid molecules encoding a polypeptide of the invention and fragments of such nucleic acid molecules suitable for use as PCR primers for the amplification or mutation of nucleic acid molecules.

An "isolated polynucleotide" or "isolated nucleic acid" is a DNA or RNA that is not immediately contiguous with both of the coding sequences with which it is immediately contiguous (one on the 5' end and one on the 3' end) in the naturally occurring genome of the organism from which it is derived. Thus, in one embodiment, an isolated nucleic acid includes some or all of the 5' non-coding (e.g., promotor) sequences that are immediately contiguous to the coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA that is part of a hybrid gene encoding an additional polypeptide that is substantially free of cellular material, viral material, or culture medium (when produced by recombinant DNA techniques), or chemical precursors or other chemicals (when chemically synthesized). Moreover, an "isolated nucleic acid fragment" is a nucleic acid fragment that is not naturally occurring as a fragment and would not be found in the natural state.

As used herein, the terms "polynucleotide" or "nucleic acid molecule" are intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. The nucleic acid may be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases.

Another embodiment of the invention provides an isolated nucleic acid molecule that is antisense to a nucleic acid molecule according to the invention. Also included within the scope of the invention are the complement strands of the nucleic acid molecules described herein.

Sequencing Errors

The sequence information as provided herein should not be so narrowly construed as to require inclusion of erroneously identified bases. The specific sequences disclosed herein can be readily used to isolate the complete gene from filamentous fungi, in particular *Aspergillus niger* which in turn can easily be subjected to further sequence analyses thereby identifying sequencing errors.

Unless otherwise indicated, all nucleotide sequences determined by sequencing a DNA molecule herein were determined using an automated DNA sequencer and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

The person skilled in the art is capable of identifying such erroneously identified bases and knows how to correct for such errors.

Nucleic Acid Fragments, Probes and Primers

A nucleic acid molecule according to the invention may comprise only a portion or a fragment of the nucleic acid sequence selected from the group consisting of SEQ ID NO: 1, 2, 4, 5, 7, 8, 10, 11, 13 and 14, for example a fragment which can be used as a probe or primer or a fragment encoding a portion of a protein according to the invention. The nucleotide sequence determined from the cloning of the phospholipase gene and cDNA allows for the generation of probes and primers designed for use in identifying and/or cloning other phospholipase family members, as well as phospholipase homologues from other species. The probe/primer typically comprises substantially purified oligonucleotide which typically comprises a region of nucleotide sequence that hybridizes preferably under highly stringent conditions to at least about 12 or 15, preferably about 18 or 20, preferably about 22 or 25, more preferably about 30, 35, 40, 45, 50, 55, 60, 65, or 75 or more consecutive nucleotides of a nucleotide sequence selected from the group consisting of SEQ ID NO: 1, 2, 4, 5, 7, 8, 10, 11, 13 and 14 or of a functional equivalent thereof.

Probes based on the nucleotide sequences provided herein can be used to detect transcripts (mostly mRNA) or genomic sequences encoding the same or homologous proteins for instance in other organisms. In preferred embodiments, the probe further comprises a label group attached thereto, e.g., the label group can be a radioisotope, a fluorescent compound, an enzyme, or an enzyme cofactor. Such probes can also be used as part of a diagnostic test kit for identifying cells that express a phospholipase.

Identity & Homology

The terms "homology" or "percent identity" are used interchangeably herein. For the purpose of this invention, it is defined here that in order to determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

The skilled person will be aware of the fact that several different computer programmes are available to determine the homology between two sequences. For instance, a comparison of sequences and determination of percent identity between two sequences can be accomplished using a mathematical algorithm. In a preferred embodiment, the percent identity between two amino acid sequences is determined using the Needleman and Wunsch (J. Mol. Biol. (48): 444-453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

In yet another embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity two amino acid or nucleotide sequence is determined using the algorithm of E. Meyers and W. Miller (CABIOS, 4:11-17 (1989) which has been incorporated into the ALIGN program (version 2.0) (available at: http://vega.igh.cnrs.fr/bin/align-guess.cgi) using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the BLASTN and BLASTX programs (version 2.0) of Altschul, et al. (1990) J. Mol. Biol. 215:403-10. BLAST nucleotide searches can be performed with the BLASTN program, score=100, word length=12 to obtain nucleotide sequences homologous to PLP03 nucleic acid molecules of the invention. BLAST protein searches can be performed with the BLASTX program, score=50, word length=3 to obtain amino acid sequences homologous to PLP03 protein molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., BLASTX and BLASTN) can be used. See http://www.ncbi.nlm.nih.gov.

Hebridisation

As used herein, the term "hybridizing" is intended to describe conditions for hybridization and washing under which nucleotide sequences at least about 50%, at least about 60%, at least about 70%, more preferably at least about 80%, even more preferably at least about 85% to 90%, more preferably at least 95% homologous to each other typically remain hybridized to each other.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., preferably at 60° C. and even more preferably at 65° C.

Highly stringent conditions include, for example, hybridizing at 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridisation conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

Obtaining Full Length DNA from Other Organisms

In a typical approach, cDNA libraries constructed from other organisms, e.g. filamentous fungi, in particular from the species *Aspergillus* can be screened.

For example, *Aspergillus* strains can be screened for homologous polynucleotides by Northern blot analysis. Upon detection of transcripts homologous to polynucleotides according to the invention, cDNA libraries can be constructed from RNA isolated from the appropriate strain, utilizing standard techniques well known to those of skill in the art. Alternatively, a total genomic DNA library can be screened using a probe hybridisable to a polynucleotide according to the invention.

Homologous gene sequences can be isolated, for example, by performing PCR using two degenerate oligonucleotide primer pools designed on the basis of nucleotide sequences as taught herein.

The template for the reaction can be cDNA obtained by reverse transcription of mRNA prepared from strains known or suspected to express a polynucleotide according to the invention. The PCR product can be subcloned and sequenced to ensure that the amplified sequences represent the sequences of a new PLP03 nucleic acid sequence, or a functional equivalent thereof.

The PCR fragment can then be used to isolate a full length cDNA clone by a variety of known methods. For example, the amplified fragment can be labeled and used to screen a bacteriophage or cosmid cDNA library. Alternatively, the labeled fragment can be used to screen a genomic library.

PCR technology can also be used to isolate full-length cDNA sequences from other organisms. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis.

The resulting RNA/DNA hybrid can then be "tailed" (e.g., with guanines) using a standard terminal transferase reaction, the hybrid can be digested with RNase H, and second strand synthesis can then be primed (e.g., with a poly-C primer). Thus, cDNA sequences upstream of the amplified fragment can easily be isolated. For a review of useful cloning strategies, see e.g., Sambrook et al., supra; and Ausubel et al., supra.

Vectors

Another aspect of the invention pertains to vectors, preferably expression vectors, containing a nucleic acid encoding a protein according to the invention or a functional equivalent thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. The terms "plasmid" and "vector" can be used interchangeably herein as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vector includes one or more regulatory sequences, selected on the basis of the host cells to be used for expression, which is operatively linked to the nucleic acid sequence to be expressed. Within a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990). Regulatory sequences include those which direct constitutive or inducible expression of a nucleotide sequence in many types of host cells and those which direct expression of the nucleotide sequence only in a certain host cell (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, encoded by nucleic acids as described herein (e.g. phospholipases, mutant phospholipases, fragments thereof, variants or functional equivalents thereof, fusion proteins, etc.).

The recombinant expression vectors of the invention can be designed for expression of phospholipases in prokaryotic or eukaryotic cells. For example, a protein according to the invention can be expressed in bacterial cells such as E. coli and Bacillus species, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression vectors useful in the present invention include chromosomal-, episomal- and virus-derived vectors e.g., vectors derived from bacterial plasmids, bacteriophage, yeast episome, yeast chromosomal elements, viruses such as baculoviruses, papova viruses, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

The DNA insert should be operatively linked to an appropriate promoter, such as the phage lambda PL promoter, the E. coli lac, trp and tac promoters, the SV40 early and late promoters and promoters of retroviral LTRs, to name a few. The skilled person will know other suitable promoters. In a specific embodiment, promoters are preferred that are capable of directing a high expression level of phospholipases in filamentous fungi. Such promoters are known in the art. The expression constructs may contain sites for transcription initiation, termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-percipitation, DEAE-dextran-mediated transfection, transduction, infection, lipofection, cationic lipidmediated transfection or electroporation. Suitable methods for transforming or transfecting host cells can be found in Sambrook, et al. (*Molecular Cloning: A Laboratory Manual, 2nd,ed. Cold Spring Harbor Laboratory*, Cold Spring Harbor Laboratory Press, Cold Spring Harbor, N.Y., 1989), Davis et al., *Basic Methods in Molecular Biology* (1986) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methatrexate. A nucleic acid encoding a selectable marker is preferably introduced into a host cell on the same vector as that encoding a protein according to the invention or can be introduced on a separate vector. Cells stably transfected with the introduced nucleic acid can be identified by drug selection (e.g. cells that have incorporated the selectable marker gene will survive, while the other cells die).

Expression of proteins in prokaryotes is often carried out in *E. coli* with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety after purification of the fusion protein. Such enzymes, and their cognate recognition sequences, include Factor Xa, thrombin and enterokinase.

As indicated, the expression vectors will preferably contain selectable markers. Such markers include dihydrofolate reductase or neomycin resistance for eukarotic cell culture and tetracyline or ampicilling resistance for culturing in *E. coli* and other bacteria. Representative examples of appropriate host include bacterial cells, such as *E. coli, Streptomyces* and *Salmonella typhimurium*; fungal cells, such as yeast; insect cells such as *Drosophila* S2 and *Spodoptera* Sf9; animal cells such as CHO, COS and Bowes melanoma; and plant cells. Appropriate culture mediums and conditions for the above-described host cells are known in the art.

Among vectors preferred for use in bacteria are pQE70, pQE60 and PQE-9, available from Qiagen; pBS vectors, Phagescript vectors, Bluescript vectors, pNH8A, pNH16A, pNH18A, pNH46A, available from Stratagene; and ptrc99a, pKK223-3, pKK233-3, pDR540, pRIT5 available from Pharmacia. Among preferred eukaryotic vectors are PWLNEO, pSV2CAT, pOG44, pZT1 and pSG available from Stratagene; and pSVK3, pBPV, pMSG and pSVL available from Pharmacia. Other suitable vectors will be readily apparent to the skilled artisan.

Known bacterial promoters for use in the present invention include *E. coli* lacI and lacZ promoters, the T3 and T7 promoters, the gpt promoter, the lambda PR, PL promoters and the trp promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

Inserting an enhancer sequence into the vector may increase transcription of the DNA encoding the polypeptides of the present invention by higher eukaryotes. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signal may be incorporated into the expressed polypeptide. The signals may be endogenous to the polypeptide or they may be heterologous signals.

The polypeptide may be expressed in a modified form, such as a fusion protein, and may include not only secretion signals but also additional heterologous functional regions. Thus, for instance, a region of additional amino acids, particularly charged amino acids, may be added to the N-terminus of the polypeptide to improve stability and persistence in the host cell, during purification or during subsequent handling and storage. Also, peptide moieties may be added to the polypeptide to facilitate purification.

Polypeptides According to the Invention

The invention provides an isolated polypeptide having the amino acid sequence selected from the group consisting of SEQ ID NO: 3, 6, 9, 12, and 15 or, an amino acid sequence obtainable by expressing the polynucleotide sequences selected from the group consisting of SEQ ID NO: 1, 2, 4, 5, 7, 8, 10, 11, 13 and 14 in an appropriate host. Also, a peptide or polypeptide comprising a functional equivalent of the above polypeptides is comprised within the present invention. The above polypeptides are collectively comprised in the term "polypeptides according to the invention"

The terms "peptide" and "oligopeptide" are considered synonymous (as is commonly recognized) and each term can be used interchangeably as the context requires indicating a chain of at least two amino acids coupled by peptidyl linkages. The word "polypeptide" is used herein for chains containing more than seven amino acid residues. All oligopeptide and polypeptide formulas or sequences herein are written from left to right and in the direction from amino terminus to carboxy terminus. The one-letter code of amino acids used herein is commonly known in the art and can be found in Sambrook, et al. (*Molecular Cloning: A Laboratory Manual, 2nd, ed. Cold Spring Harbor Laboratory*, Cold Spring Harbor Laboratory Press, Cold Spring Harbor, N.Y., 1989)

By "isolated" polypeptide or protein is intended a polypeptide or protein removed from its native environment. For example, recombinantly produced polypeptides and proteins expressed in host cells are considered isolated for the purpose of the invention as are native or recombinant polypeptides which have been substantially purified by any suitable technique such as, for example, the single-step purification method disclosed in Smith and Johnson, Gene 67:31-40 (1988).

The phospholipase according to the invention can be recovered and purified from recombinant cell cultures by well-known methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention include naturally purified products, products of chemical synthetic procedures, and products produced by recombinant techniques from a prokaryotic or eukaryotic host, including, for example, bacterial, yeast, fungus, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Protein Fragments

The invention also features biologically active fragments of the polypeptides according to the invention.

Biologically active fragments of a polypeptide of the invention include polypeptides comprising amino acid sequences sufficiently identical to or derived from the amino acid sequence of the phospholipase (e.g., the amino acid sequence selected from the group consisting of SEQ ID NO: 3, 6, 9, 12 and 15), which include fewer amino acids than the full length protein, and exhibit at least one biological activity of the corresponding full-length protein. Typically, biologically active fragments comprise a domain or motif with at least one activity of the corresponding full-length protein. A biologically active fragment of a protein of the invention can be a polypeptide that is, for example, 10, 25, 50, 100 or more amino acids in length. Moreover, other biologically active portions, in which other regions of the protein are deleted, can be prepared by recombinant techniques and evaluated for one or more of the biological activities of the native form of a polypeptide of the invention.

The invention also features nucleic acid fragments that encode the above biologically active fragments of the phospholipase.

Fusion Proteins

The proteins of the present invention or functional equivalents thereof, e.g., biologically active portions thereof, can be operatively linked to a non-phospholipase polypeptide (e.g., heterologous amino acid sequences) to form fusion proteins. As used herein, a phospholipase "chimeric protein" or "fusion protein" comprises a phospholipase polypeptide operatively linked to a non-phospholipase polypeptide.

In a preferred embodiment, a fusion protein comprises at least one biologically active fragment of a phospholipase according to the invention. In another preferred embodiment, a fusion protein comprises at least two biologically active portions of a phospholipase according to the invention. Within the fusion protein, the term "operatively linked" is intended to indicate that the phospholipase and the non-phospholipase polypeptide are fused in-frame to each other either to the N-terminus or C-terminus of the phospholipase.

For example, in one embodiment, the fusion protein is a GST-phospholipase fusion protein in which the phospholipase sequences are fused to the C-terminus of the GST sequences. Such fusion proteins can facilitate the purification of recombinant phospholipase. In another embodiment, the fusion protein is a phospholipase protein containing a heterologous signal sequence at its N-terminus. In certain host cells (e.g., mammalian and yeast host cells), expression and/or secretion of phospholipase can be increased through use of a heterologous signal sequence.

In another example, the gp67 secretory sequence of the baculovirus envelope protein can be used as a heterologous signal sequence (*Current Protocols in Molecular Biology*, Ausubel et al., eds., John Wiley & Sons, 1992). Other examples of eukaryotic heterologous signal sequences include the secretory sequences of melittin and human placental alkaline phosphatase (Stratagene; La Jolla, Calif.). In yet another example, useful prokarytic heterologous signal sequences include the phoA secretory signal (Sambrook et al., supra) and the protein A secretory signal (Pharmacia Biotech; Piscataway, N.J.).

A signal sequence can be used to facilitate secretion and isolation of a protein or polypeptide of the invention. Signal sequences are typically characterized by a core of hydrophobic amino acids that are generally cleaved from the mature protein during secretion in one or more cleavage events. Such signal peptides contain processing sites that allow cleavage of the signal sequence from the mature proteins as they pass through the secretory pathway. The signal sequence directs secretion of the protein, such as from a eukaryotic host into which the expression vector is transformed, and the signal sequence is subsequently or concurrently cleaved. The protein can then be readily purified from the extracellular medium by art-recognized methods. Alternatively, the signal sequence can be linked to the protein of interest using a sequence, which facilitates purification, such as with a GST domain. Thus, for instance, the sequence encoding the polypeptide may be fused to a marker sequence, such as a sequence encoding a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al, *Proc. Natl. Acad. Sci. USA* 86:821-824 (1989), for instance, hexa-histidine provides for convenient purification of the fusion protein. The HA tag is another peptide useful for purification which corresponds to an epitope derived of influenza hemaglutinin protein, which has been described by Wilson et al., *Cell* 37:767 (1984), for instance.

Preferably, a chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g, a GST polypeptide). A nucleic acid according to the invention can be cloned into such an expression vector such that the fusion moiety is linked in-frame to the fusion moiety in order to express a fusion protein comprising a protein according to the invention.

Functional Equivalents

The terms "functional equivalents" and "functional variants" are used interchangeably herein. Functional equivalents of phospholipase encoding DNA are isolated DNA fragments that encode a polypeptide that exhibits a particular function of the *Aspergillus niger* phospholipase as defined herein. A functional equivalent of a phospholipase polypeptide according to the invention is a polypeptide that exhibits at least one function of an *Aspergillus niger* phospholipase as defined herein. Functional equivalents therefore also encompass biologically active fragments.

Functional protein or polypeptide equivalents may contain only conservative substitutions of one or more amino acids in the amino acid sequences selected from the group consisting of SEQ ID NO: 3, 6, 9, 12 and 15 or substitutions, insertions or deletions of non-essential amino acids. Accordingly, a non-essential amino acid is a residue that can be altered in an amino acid sequence selected from the group consisting of SEQ ID NO: 3, 6, 9, 12 and 15 without substantially altering the biological function. For example, amino acid residues that are conserved among the phospholipase proteins of the present invention are predicted to be particularly unamenable to alteration. Furthermore, amino acids conserved among the phospholipase proteins according to the present invention and other phospholipases are not likely to be amenable to alteration.

The term "conservative substitution" is intended to mean that a substitution in which the amino acid residue is replaced with an amino acid residue having a similar side chain. These families are known in the art and include amino acids with basic side chains (e.g. lysine, arginine and hystidine), acidic side chains (e.g. aspartic acid, glutamic acid), uncharged polar side chains (e.g., glycine, asparagines, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine tryptophan, histidine).

Functional nucleic acid equivalents may typically contain silent mutations or mutations that do not alter the biological function of encoded polypeptide. Accordingly, the invention provides nucleic acid molecules encoding phospholipase proteins that contain changes in amino acid residues that are not essential for a particular biological activity. Such proteins differ in the amino acid sequence selected from the group consisting of SEQ ID NO: 3, 6, 9, 12 and 15, yet they retain at least one biological activity. In one embodiment the isolated nucleic acid molecule comprises a nucleotide sequence encoding a protein, wherein the protein comprises a substantially homologous amino acid sequence of at least about 60%, 65%, 70%, 75%, 80%, 85%, 90%, 95%, 96%, 97%, 98%, 99% or more homologous to the amino acid sequence selected from the group consisting of SEQ ID NO: 3, 6, 9, 12 and 15.

For example, guidance concerning how to make phenotypically silent amino acid substitutions is provided in Bowie, J. U. et al., Science 247:1306-1310 (1990) wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selects or screens to identify sequences that maintain functionality. As the authors state, these studies have revealed that proteins are surprisingly tolerant of amino acid substitutions. The authors further indicate which changes are likely to be permissive at a certain position of the protein. For example, most buried amino acid residues require non-polar side chains, whereas few features of surface side chains are generally conserved. Other such phenotypically silent substitutions are described in Bowie et al, supra, and the references cited therein.

An isolated nucleic acid molecule encoding a protein homologous to the protein selected from the group consisting of SEQ ID NO: 3, 6, 9, 12 and 15 can be created by introducing one or more nucleotide substitutions, additions or deletions into the coding nucleotide sequences selected from the group consisting of SEQ ID NO:1 and 2, 4 and 5, 7 and 8, 10 and 11, 13 and 14 respectively such that one or more amino acid substitutions, deletions or insertions are introduced into the encoded protein. Such mutations may be introduced by standard techniques, such as site-directed mutagenesis and PCR-mediated mutagenesis.

The term "functional equivalents" also encompasses orthologues of the *Aspergillus niger* phospholipases provided herein. Orthologues of the *Aspergillus niger* phospholipases are proteins that can be isolated from other strains or species and possess a similar or identical biological activity. Such orthologues can readily be identified as comprising an amino acid sequence that is substantially homologous to the amino acid sequences selected from the group consisting of SEQ ID NO: 3, 6, 9, 12 and 15.

As defined herein, the term "substantially homologous" refers to a first amino acid or nucleotide sequence which contains a sufficient or minimum number of identical or equivalent (e.g., with similar side chain) amino acids or nucleotides to a second amino acid or nucleotide sequence such that the first and the second amino acid or nucleotide sequences have a common domain. For example, amino acid or nucleotide sequences which contain a common domain having about 60%, preferably 65%, more preferably 70%, even more preferably 75%, 80%, 85%, 90%, 95%, 96%, 97%, 98% or 99% identity or more are defined herein as sufficiently identical.

Also, nucleic acids encoding other phospholipase family members, which thus have a nucleotide sequence that differs from a nucleotide sequence selected from the group consisting of SEQ ID NO: 1, 2, 4, 5, 7, 8, 10, 11, 13 and 14 are within the scope of the invention. Moreover, nucleic acids encoding phospholipase proteins from different species which thus have a nucleotide sequence which differs from a nucleotide sequence selected from the group consisting of SEQ ID NO: 1, 2, 4, 5, 7, 8, 10, 11, 13 and 14 are within the scope of the invention. Nucleic acid molecules corresponding to variants (e.g. natural allelic variants) and homologues of the DNA according to the invention can be isolated based on their homology to the nucleic acids disclosed herein using the cDNAs disclosed herein or a suitable fragment thereof, as a hybridisation probe according to standard hybridisation techniques preferably under highly stringent hybridisation conditions.

In addition to naturally occurring allelic variants of the *Aspergillus niger* sequences provided herein, the skilled person will recognise that changes can be introduced by mutation into the nucleotide sequences selected from the group consisting of SEQ ID NO: 1, 2, 4, 5, 7, 8, 10, 11, 13 and 14 thereby leading to changes in the amino acid sequence of the phospholipase protein without substantially altering the function of the protein.

In another aspect of the invention, improved phospholipases are provided. Improved phospholipases are proteins wherein at least one biological activity is improved. Such proteins may be obtained by randomly introducing mutations along all or part of the coding sequence, such as by saturation mutagenesis, and the resulting mutants can be expressed recombinantly and screened for biological activity. For instance, the art provides for standard assays for measuring the enzymatic activity of phospholipases and thus improved proteins may easily be selected.

In a preferred embodiment the phospholipase has an amino acid sequence selected from the group consisting of SEQ ID NO: 3, 6, 9, 12 and 15. In another embodiment, the phospholipase is substantially homologous to the amino acid sequence selected from the group consisting of SEQ ID NO: 3, 6, 9, 12 and 15 and retains at least one biological activity of a phospholipase selected from the group consisting of SEQ ID NO: 3, 6, 9, 12 and 15 respectively, yet differs in amino acid sequence due to natural variation or mutagenesis as described above.

In a further preferred embodiment, the phospholipase has an amino acid sequence encoded by an isolated nucleic acid fragment capable of hybridising to a nucleic acid selected from the group consisting of SEQ ID NO: 1, 2, 4, 5, 7, 8, 10, 11, 13 and 14, preferably under highly stringent hybridisation conditions. Accordingly, the phospholipase is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence selected from the group consisting of SEQ ID NO: 3, 6, 9, 12 and 15.

In particular, the phospholipase is a protein which comprises an amino acid sequence at least about 50%, 55%, 60%, 65%, 70%, 75%, 80%, 85%, 90%, 95%, 96%, 97%, 98%, 99% or more homologous to the amino acid sequence shown in SEQ ID NO: 3 or the phospholipase is a protein which comprises an amino acid sequence at least about 55%, 60%, 65%, 70%, 75%, 80%, 85%, 90%, 95%, 96%, 97%, 98%, 99% or more homologous to the amino acid sequence shown in SEQ ID NO: 6, or the phospholipase is a protein which comprises an amino acid sequence at least about 75%, 80%, 85%, 90%, 95%, 96%, 97%, 98%, 99% or more homologous to the amino acid sequence shown in SEQ ID NO: 9, or the phospholipase is a protein which comprises an amino acid sequence at least about 40%, 45%, 50%, 55%, 60%, 65%, 70%, 75%, 80%, 85%, 90%, 95%, 96%, 97%, 98%, 99% or more homologous to the amino acid sequence shown in SEQ ID NO: 12 or the phospholipase is a protein which comprises an amino acid sequence at least about 60%, 65%, 70%, 75%, 80%, 85%, 90%, 95%, 96%, 97%, 98%, 99% or more homologous to the amino acid sequence shown in SEQ ID NO: 15.

Functional equivalents of a protein according to the invention can also be identified e.g. by screening combinatorial libraries of mutants, e.g. truncation mutants, of the protein of the invention for phospholipase activity. In one embodiment, a variegated library of variants is generated by combinatorial mutagenesis at the nucleic acid level. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods that can be used to produce libraries of potential variants of the polypeptides of the invention from a degenerate oligonucleotide sequence. Methods for synthesizing degenerate oligonucleotides are known in the art (see, e.g., Narang (1983) Tetrahedron 39:3; Itakura et al. (1984) Annu. Rev. Biochem. 53:323; Itakura et al. (1984) Science 198:1056; Ike et al. (1983) Nucleic Acid Res. 11:477).

In addition, libraries of fragments of the coding sequence of a polypeptide of the invention can be used to generate a variegated population of polypeptides for screening a subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the invention (Arkin and Yourvan (1992) Proc. Natl. Acad. Sci. USA 89:7811-7815; Delgrave et al. (1993) Protein Engineering 6(3):327-331).

It will be apparent for the person skilled in the art that DNA sequence polymorphisms that may lead to changes in the amino acid sequence of the phospholipase may exist within a given population. Such genetic polymorphisms may exist in cells from different populations or within a population due to natural allelic variation. Allelic variants may also include functional equivalents.

Fragments of a polynucleotide according to the invention may also comprise polynucleotides not encoding functional polypeptides. Such polynucleotides may function as probes or primers for a PCR reaction.

Nucleic acids according to the invention, irrespective of whether they encode functional or non-functional polypeptides, can be used as hybridization probes or polymerase chain reaction (PCR) primers. Uses of the nucleic acid molecules of the present invention that do not encode a polypeptide having a phospholipase activity include, inter alia, (1) isolating the gene encoding the phospholipase of the invention, or allelic variants thereof from a cDNA library e.g. from other organisms than *Aspergillus niger*; (2) in situ hybridisation (e.g. FISH) to metaphase chromosomal spreads to provide precise chromosomal location of the PLP03 gene as described in Verma et al., Human Chromosomes: a Manual of Basic Techniques, Pergamon Press, New York (1988); (3) Northern blot analysis for detecting expression of the phospholipase mRNA in specific tissues and/or cells and 4) probes and primers that can be used as a diagnostic tool to analyse the presence of a nucleic acid hybridisable to the phospholipase probe in a given biological (e.g. tissue) sample.

Also encompassed by the invention is a method of obtaining a functional equivalent of a phospholipase encoding gene or cDNA. Such a method entails obtaining a labelled probe that includes an isolated nucleic acid which encodes all or a portion of the sequence selected from the group consisting of SEQ ID NO: 3, 6, 9, 12 and 15 or a variant thereof; screening a nucleic acid fragment library with the labelled probe under conditions that allow hybridisation of the probe to nucleic acid fragments in the library, thereby forming nucleic acid duplexes, and preparing a full-length gene sequence from the nucleic acid fragments in any labelled duplex to obtain a gene related to the phospholipase gene.

In one embodiment, a nucleic acid according to the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to a nucleic acid sequence selected from the group consisting of SEQ ID NO: 1, 2, 4, 5, 7, 8, 10, 11, 13 and 14 or the complement thereof.

In another preferred embodiment a polypeptide of the invention is at least 40%, 45%, 50%, 55%, 60%, 65%, 70%, 75%, 80%, 85%, 90%, 91%, 92%, 93%, 94%, 95%, 96%, 97%, 98%, 99%, or more homologous to the amino acid sequence selected from the group consisting of SEQ ID NO: 3, 6, 9, 12 and 15.

Host Cells

In another embodiment, the invention features cells, e.g., transformed host cells or recombinant host cells that contain a nucleic acid encompassed by the invention. A "transformed cell" or "recombinant cell" is a cell into which (or into an ancestor of which) has been introduced, by means of recombinant DNA techniques, a nucleic acid according to the invention. Both prokaryotic and eukaryotic cells are included, e.g., bacteria, fungi, yeast, and the like, especially preferred are cells from filamentous fungi, in particular *Aspergillus niger*.

A host cell can be chosen that modulates the expression of the inserted sequences, or modifies and processes the gene product in a specific, desired fashion. Such modifications (e.g., glycosylation) and processing (e.g., cleavage) of protein products may facilitate optimal functioning of the protein.

Various host cells have characteristic and specific mechanisms for post-translational processing and modification of proteins and gene products. Appropriate cell lines or host systems familiar to those of skill in the art of molecular biology and/or microbiology can be chosen to ensure the desired and correct modification and processing of the foreign protein expressed. To this end, eukaryotic host cells that possess the cellular machinery for proper processing of the primary transcript, glycosylation, and phosphorylation of the gene product can be used. Such host cells are well known in the art.

Host cells also include, but are not limited to, mammalian cell lines such as CHO, VERO, BHK, HeLa, COS, MDCK, 293, 3T3, WI38, and choroid plexus cell lines.

If desired, the polypeptides according to the invention can be produced by a stably-transfected cell line. A number of vectors suitable for stable transfection of mammalian cells are available to the public, methods for constructing such cell lines are also publicly known, e.g., in Ausubel et al. (supra).

Antibodies

The invention further features antibodies, such as monoclonal or polyclonal antibodies that specifically bind phospholipases according to the invention.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to PLP03 protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)). Thus, these fragments are preferred.

The antibodies of the present invention may be prepared by any of a variety of methods. For example, cells expressing the phospholipase or an antigenic fragment thereof can be administered to an animal in order to induce the production of sera containing polyclonal antibodies. In a preferred method, a preparation of phospholipase is prepared and purified to render it substantially free of natural contaminants. Such a preparation is then introduced into an animal in order to produce polyclonal antisera of greater specific activity.

In the most preferred method, the antibodies of the present invention are monoclonal antibodies (or phospholipase-binding fragments thereof). Such monoclonal antibodies can be prepared using hybridoma technology (Kohler et al., *Nature* 256:495 (1975); Kohler et al., *Eur. J. Immunol.* 6:511 (1976); Hammerling et al., In: *Monoclonal Antibodies and T-Cell Hybridomas*, Elsevier, N.Y., pp. 563-681 (1981)). In general, such procedures involve immunizing an animal (preferably a mouse) with a protein according to the invention or, with a cell expressing a protein according to the invention. The splenocytes of such mice are extracted and fused with a suitable myeloma cell line. Any suitable myeloma cell line may be employed in accordance with the present invention; however, it is preferably to employ the parent myeloma cell line (SP$_2$O), available from the American Type Culture Collection, Rockville, Md. After fusion, the resulting hybridoma cells are selectively maintained in HAT medium, and then cloned by limiting dilution as described by Wands et al. (*Gastro-enterology* 80:225-232 (1981)). The hybridoma cells obtained through such a selection are then assayed to identify clones, which secrete antibodies capable of binding the PLP03 protein antigen. In general, the polypeptides can be coupled to a carrier protein, such as KLH, as described in Ausubel et al., supra, mixed with an adjuvant, and injected into a host mammal.

In particular, various host animals can be immunized by injection of a polypeptide of interest. Examples of suitable host animals include rabbits, mice, guinea pigs, and rats. Various adjuvants can be used to increase the immunological response, depending on the host species, including but not limited to Freund's (complete and incomplete), adjuvant mineral gels such as aluminum hydroxide, surface active substances such as lysolecithin, pluronic polyols, polyanions, peptides, oil emulsions, keyhole limpet hemocyanin, dinitrophenol, BCG (bacille Calmette-Guerin) and *Corynebacterium parvum*. Polyclonal antibodies are heterogeneous populations of antibody molecules derived from the sera of the immunized animals.

Such antibodies can be of any immunoglobulin class including IgG, IgM, IgE, IgA, IgD, and any subclass thereof. The hybridomas producing the mAbs of this invention can be cultivated in vitro or in vivo.

Once produced, polyclonal or monoclonal antibodies are tested for specific recognition of a protein according to the invention or a functional equivalent thereof in an immunoassay, such as a Western blot or immunoprecipitation analysis using standard techniques, e.g., as described in Ausubel et al., supra. Antibodies that specifically bind to a protein according to the invention or functional equivalents thereof are useful in the invention. For example, such antibodies can be used in an immunoassay to detect a protein according to the invention in pathogenic or non-pathogenic strains of *Aspergillus* (e.g., in *Aspergillus* extracts).

Preferably, antibodies of the invention are produced using fragments of the protein according to the invention that appears likely to be antigenic, by criteria such as high frequency of charged residues. For example, such fragments may be generated by standard techniques of PCR, and then cloned into the pGEX expression vector (Ausubel et al., supra). Fusion proteins may then be expressed in *E. coli* and purified using a glutathione agarose affinity matrix as described in Ausubel, et al., supra. If desired, several (e.g., two or three) fusions can be generated for each protein, and each fusion can be injected into at least two rabbits. Antisera can be raised by injections in a series, typically including at least three booster injections. Typically, the antisera are checked for their ability to immunoprecipitate a recombinant PLP03 polypeptide or functional equivalents thereof whereas unrelated proteins may serve as a control for the specificity of the immune reaction.

Alternatively, techniques described for the production of single chain antibodies (U.S. Pat. Nos. 4,946,778 and 4,704, 692) can be adapted to produce single chain antibodies against a protein according to the invention or functional equivalents thereof. Kits for generating and screening phage display libraries are commercially available e.g. from Pharmacia.

Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 20791; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *BioTechnology* 9:1370-1372; Hay et al. (1992) *Hum. Antibod. Hybridomas* 3:81-85; Huse et al. (1989) *Science* 246; 1275-1281; Griffiths et al. (1993) *EMBO J.* 12:725-734.

Polyclonal and monoclonal antibodies that specifically bind a protein according to the invention or functional equivalents thereof can be used, for example, to detect expression of a gene encoding a protein according to the invention or a functional equivalent thereof e.g. in another strain of *Aspergillus*. For example, a protein according to the invention can be readily detected in conventional immunoassays of *Aspergillus* cells or extracts. Examples of suitable assays include, without limitation, Western blotting, ELISA's, radio immune assays (RIA's), and the like.

By "specifically binds" is meant that an antibody recognizes and binds a particular antigen, e.g., a protein according to the invention, but does not substantially recognize and bind other unrelated molecules in a sample.

Antibodies can be purified, for example, by affinity chromatography methods in which the polypeptide antigen is immobilized on a resin.

An antibody (e.g. a monoclonal antibody) directed against a protein according to the invention can be used to isolate the protein by standard techniques, such as affinity chromatography or immunoprecipitation. Moreover, such an antibody can be used to detect the protein (e.g., in a cellular lysate or cell supernatant) in order to evaluate the abundance and pattern of expression of the protein. The antibodies can also be used diagnostically to monitor protein levels in cells or tissue as part of a clinical testing procedure, e.g., to, for example, determine the efficacy of a given treatment regimen or in the diagnosis of *Aspergillosis*.

Coupling the antibody to a detectable substance can facilitate detection. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive materials include $^{125}I$, $^{131}I$, $^{35}S$ or $^{3}H$.

Preferred epitopes encompassed by the antigenic peptide are regions that are located on the surface of the protein, e.g., hydrophilic regions. Hydrophobicity plots of proteins can be used to identify hydrophilic regions.

The antigenic peptide of a protein according to the invention comprises at least 7, preferably 10, 15, 20, or 30 contiguous amino acid residues of the amino acid sequence selected from the group consisting of SEQ ID NO: 3, 6, 9, 12 and 15 and encompasses an epitope of the protein such that an antibody raised against the peptide forms a specific immune complex with the protein. Preferred epitopes encompassed by the antigenic peptide are regions of the protein according to the invention that are located on the surface of the protein, e.g., hydrophilic regions, hydrophobic regions, alpha-helices containing regions, beta-strand or sheet containing regions, coil regions, turn regions and flexible regions.

Immunoassays

Qualitative or quantitative determination of a protein according to the present invention in a biological sample can occur using any art-known method. Antibody-based techniques provide special advantages for assaying specific polypeptide levels in a biological sample. In these, the specific recognition is provided by the primary antibody (polyclonal or monoclonal) but the secondary detection system can utilize fluorescent, enzyme, or other conjugated secondary antibodies. As a result, an immunocomplex is obtained.

Accordingly, the invention provides a method for diagnosing whether a certain organism is infected with *Aspergillus* comprising the steps of:
  Isolating a biological sample from said organism suspected to be infected with *Aspergillus*,
  reacting said biological sample with an antibody according to the invention,
  determining whether immunocomplexes are formed.

Tissues can also be extracted, e.g., with urea and neutral detergent, for the liberation of protein for Western-blot or dot/slot assay. This technique can also be applied to body fluids.

Other antibody-based methods useful for detecting a protein according to the invention include immunoassays, such as the enzyme linked immunosorbent assay (ELISA) and the radioimmunoassay (RIA). For example, monoclonal antibodies against a protein according to the invention can be used both as an immunoabsorbent and as an enzyme-labeled probe to detect and quantify the protein according to the invention. The amount of specific protein present in the sample can be calculated by reference to the amount present in a standard preparation using a linear regression computer algorithm. In another ELISA assay, two distinct specific monoclonal antibodies can be used to detect a protein according to the invention in a biological fluid. In this assay, one of the antibodies is used as the immuno-absorbent and the other as the enzyme-labeled probe.

The above techniques may be conducted essentially as a "one-step" or "two-step" assay. The "one-step" assay involves contacting a protein according to the invention with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyse the production of hydrogen peroxide by reacting with substrate. Activity of an oxidase label may be assayed by measuring the concentration of hydrogen peroxide formed by the enzyme-labelled antibody/substrate reaction.

Besides enzymes, other suitable labels include radioisotopes, such as iodine ($^{125}$I, $^{131}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Specific binding of a test compound to a protein according to the invention can be detected, for example, in vitro by reversibly or irreversibly immobilizing the protein according to the invention on a substrate, e.g., the surface of a well of a 96-well polystyrene microtitre plate. Methods for immobilizing polypeptides and other small molecules are well known in the art. For example, the microtitre plates can be coated with a protein according to the invention by adding the protein in a solution (typically, at a concentration of 0.05 to 1 mg/ml in a volume of 1-100 μl) to each well, and incubating the plates at room temperature to 37° C. for 0.1 to 36 hours. Proteins that are not bound to the plate can be removed by shaking the excess solution from the plate and then washing the plate (once or repeatedly) with water or a buffer. Typically, the polypeptide is contained in water or a buffer. The plate is then washed with a buffer that lacks the bound polypeptide. To block the free protein-binding sites on the plates, the plates are blocked with a protein that is unrelated to the bound polypeptide. For example, 300 μl of bovine serum albumin (BSA) at a concentration of 2 mg/ml in Tris-HCl is suitable. Suitable substrates include those substrates that contain a defined cross-linking chemistry (e.g., plastic substrates, such as polystyrene, styrene, or polypropylene substrates from Corning Costar Corp. (Cambridge, Mass.), for example). If desired, a beaded particle, e.g., beaded agarose or beaded sepharose, can be used as the substrate.

Binding of the test compound to the proteins according to the invention can be detected by any of a variety of methods known in the art. For example, a specific antibody can be used in an immunoassay. If desired, the antibody can be labelled (e.g., fluorescently or with a radioisotope) and detected directly (see, e.g., West and McMahon, J. Cell Biol. 74:264, 1977). Alternatively, a second antibody can be used for detection (e.g., a labelled antibody that binds the Fc portion of an anti-AN97 antibody). In an alternative detection method, the protein according to the invention is labelled, and the label is detected (e.g., by labelling a protein according to the invention with a radioisotope, fluorophore, chromophore, or the like). In still another method, the protein according to the invention is produced as a fusion protein with a protein that can be detected optically, e.g., green fluorescent protein (which can be detected under UV light). In an alternative method, the protein according to the invention can be covalently attached to or fused with an enzyme having a detectable enzymatic activity, such as horse radish peroxidase, alkaline phosphatase, α-galactosidase or glucose oxidase. Genes encoding all of these enzymes have been cloned and are readily available for use by those of skill in the art. If desired, the fusion protein can include an antigen, and such an antigen can be detected and measured with a polyclonal or monoclonal antibody using conventional methods. Suitable antigens include enzymes (e.g., horse radish peroxidase, alkaline phosphatase, and α-galactosidase) and non-enzymatic polypeptides (e.g., serum proteins, such as BSA and globulins, and milk proteins, such as caseins).

Epitopes, Antigens and Immunogens

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, H. M. et al., Proc. Natl. Acad. Sci. USA 81:3998-4002 (1984).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G. et al., Science 219:660-666 (1984). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, soluble peptides, especially those containing proline residues, usually are effective. Sutcliffe et al., supra, at 661. For instance, 18 of 20 peptides designed according to these guidelines, containing 8-39 residues covering 75% of the sequence of the influenza virus hemagglutinin HAI polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope bearing peptides or polypeptides are useful to detect the mimicked protein, and antibodies to different peptides may be used for tracking the fate of various regions of a protein precursor that undergoes posttranslation processing. The peptides and anti-peptide antibodies may be used in a variety of qualitative or quantitative assays for the mimicked protein, for instance in competition assays since it has been shown that even short peptides (e.g., about 9 amino acids) can bind and displace the larger peptides in immunoprecipitation assays. See, for instance, Wilson, I. A. et al., Cell 37:767-778 at 777 (1984). The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide that acts as a carrier during recombinant production and purification, as well as during immunization to produce anti-peptide antibodies.

Epitope-bearing peptides also may be synthesized using known methods of chemical synthesis. For instance, Houghten has described a simple method for synthesis of large numbers of peptides, such as 10-20 mg of 248 different 13 residue peptides representing single amino acid variants of a segment of the HAI polypeptide which were prepared and characterized (by ELISA-type binding studies) in less than four weeks. Houghten, R. A., Proc. Natl. Acad. Sci. USA 82:5131-5135 (1985). This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500-1000 or more syntheses to be conducted simultaneously. Houghten et al., supra, at 5134.

Epitope-bearing peptides and polypeptides of the invention can be used to induce antibodies according to methods well known in the art. See, for instance, Sutcliffe et al., supra; Wilson et al., supra; Chow, M. et al., Proc. Natl. Acad. Sci. USA 82:910-914; and Bittle, F. J. et al., J. Gen. Virol. 66:2347-2354 (1985). Generally, animals may be immunized with free peptide; however, anti-peptide antibody titre may be boosted by coupling of the peptide to a macromolecular carrier, such as keyhole limpet hemocyanin (KLH) or tetanus toxoid. For instance, peptides containing cysteine may be coupled to carrier using a linker such as maleimidobenzoyl-N-hydroxysuccinimide ester (MBS), while other peptides may be coupled to carrier using a more general linking agent such as glutaraldehyde. Animals such as rabbits, rats and mice are immunized with either free or carrier coupled peptides, for instance, by intraperitoneal and/or intradermal injection of emulsions containing about 100 µg peptide or carrier protein and Freund's adjuvant. Several booster injections may be needed, for instance, at intervals of about two weeks, to provide a useful titre of anti-peptide antibody that can be detected, for example, by ELISA assay using free peptide adsorbed to a solid surface. The titre of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., 1984, supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, Geysen et al. located the immunologically important epitope in the coat protein of foot-and-mouth disease virus with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogues of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds), which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1-C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Use of Phospholipases in Industrial Processes

The invention also relates to the use of the phospholipase according to the invention in a selected number of industrial and pharmaceutical processes. Despite the long-term experience obtained with these processes, the phospholipase according to the invention features a number of significant advantages over the enzymes currently used. Depending on the specific application, these advantages can include aspects like lower production costs, higher specificity towards the substrate, being less antigenic, less undesirable side activities, higher yields when produced in a suitable microorganism, more suitable pH and temperature ranges, better tastes of the final product as well as food grade and kosher aspects.

An important aspect of the phospholipases according to the invention is that they cover a whole range of pH and temperature optima that are ideally suited for a variety of applications. For example many large-scale processes benefit from relatively high processing temperatures of 50° C. or higher, e.g. to control the risks of microbial infections. Several phospholipases according to the invention comply with this demand but at the same time they do not possess such heat stability that they resist inactivation by an additional heat treatment. The latter feature allows production routes that yield final products, such as baked products like bread that are free of residual enzyme activity. Similarly many feed and food products have slightly acidic pH values so that phospholipases with acidic or near neutral pH optima are preferred for their processing. A phospholipase according to the invention complies with this requirement as well.

The phospholipases of the present invention may be used in any application where it is desired to hydrolyse a phospholipid or to obtain specific cleavage products thereof. For example application of the polypeptides according to the invention can yield lysophospholipids, diacylglycerols, choline- or ethanolaminephosphates, lysophosphatidylcholine, lysophosphatidylethanolamine and various phosphatidates. The phospholipases of the present invention are preferably used at a pH optimal for activity.

Phospholipases of the present invention may be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP-A-219,269 and EP-A-808,903.

Phospholipases of the present invention may be used in a process to reduce the phospholipid content in edible oil by treating the oil with the polypeptide to hydrolyse a major portion of the phospholipid and separating an aqueous phase containing the hydrolysed phospholipid from the oil. Such a process is applicable to the purification of any edible oil that contains phospholipid, e.g., vegetable oil such as soybean oil, rapeseed oil, and sunflower oil. Prior to phospholipase treatment, the oil is preferably pre-treated to remove slime (mucilage), e.g., by wet refining. Typically, the oil will contain 50-250 ppm of phosphorus as phospholipid at the beginning of the treatment with the phospholipase, and the treatment may reduce the phosphorus value to below 5-10 ppm. The phospholipase treatment is conducted by dispersing an aqueous solution of the phospholipase, preferably as droplets with an average diameter below 10 μm. The amount of water is preferably 0.5-5% by weight in relation to the oil. An emulsifier may optionally be added. Mechanical agitation may be applied to maintain the emulsion. The phospholipase treatment can be conducted at a pH in the range of about 3.5 to about 5 to maximize the enzyme's performance, or a pH in the range of about 1.5 to about 3 (e.g., 2-3) may be used in order to suppress the alkaline hydrolysis of triglycerides (saponification). The pH may be adjusted by adding citric acid, a citrate buffer, or hydrochloric acid. A suitable temperature is generally 30-70° C. (particularly 30-45° C., e.g., 35-40° C.).

The reaction time will typically be 1-12 hours (e.g., 2-6 hours). A suitable enzyme dosage will usually be 0.1-10 mg per liter (e.g., 0.5-5 mg per liter). The phospholipase treatment may be conducted batchwise, e.g., in a tank with stirring, or it may be continuous, e.g., a series of stirred tank reactors. The phospholipase treatment is followed by separation of an aqueous phase and an oil phase. The separation may be performed by conventional means, e.g., centrifugation. The aqueous phase will contain phospholipase, and the enzyme may be re-used to improve the process economy. The treatment may be performed using any of the methods known in the art. See, for example, U.S. Pat. No. 5,264,367, EP-A-654,527, JP-A-2-153997.

Baked products are prepared from a dough which is usually made from the basic ingredients flour, water and optionally salt. Depending on the baked products, other optional ingredients are sugars, flavours etceteras. For leavened products, primarily baker's yeast is used next to chemical leavening systems such as a combination of an acid (generating compound) and bicarbonate. In order to improve the handling properties of the dough and/or the final properties of the baked products there is a continuous effort to develop processing aids with improving properties. Dough properties that are to be improved comprise machineability, gas retaining capability, etcetera. Properties of the baked products that may be improved comprise loaf volume, crust crispiness, crumb texture and softness, taste and flavour and shelf life. The currently existing processing aids can be divided into two groups: chemical additives and enzymes.

Chemical additives with improving properties comprise oxidising agents such as ascorbic acid, bromate and azodicarbonate, reducing agents such as L-cysteine and glutathione, emulsifiers acting as dough conditioners such as diacetyl tartaric esters of mono/diglycerides (DATEM), sodium stearoyl lactylate (SSL) or calcium stearoyl lactylate (CSL), or acting as crumb softeners such as glycerol monostearate (GMS) etceteras, fatty materials such as triglycerides (fat) or lecithin and others.

Presently, there is a trend to replace the chemical additives by enzymes. The latter are considered to be more natural compounds and therefore more accepted by the consumer. Suitable enzymes may be selected from the group consisting of starch degrading enzymes, arabinoxylan- and other hemicellulose degrading enzymes, cellulose degrading enzymes, oxidizing enzymes, fatty material splitting enzymes and protein degrading enzymes.

The present invention also relates to methods for preparing a dough or a baked product comprising incorporating into the dough an effective amount of a phospholipase of the present invention which improves one or more properties of the dough or the baked product obtained from the dough relative to a dough or a baked product in which the polypeptide is not incorporated.

The phrase "incorporating into the dough" is defined herein as adding the phospholipase according to the invention to the dough, any ingredient from which the dough is to be made, and/or any mixture of dough ingredients form which the dough is to be made. In other words, the phospholipase according to the invention may be added in any step of the dough preparation and may be added in one, two or more steps. The phospholipase according to the invention is added to the ingredients of a dough that is kneaded and baked to make the baked product using methods well known in the art. See, for example, U.S. Pat. No. 4,567,046, EP-A426,211, JP-A-60-78529, JP-A-62-111629, and JP-A-63-258528.

The term "effective amount" is defined herein as an amount of the phospholipase according to the invention that is sufficient for providing a measurable effect on at least one property of interest of the dough and/or baked product.

The term "improved property" is defined herein as any property of a dough and/or a product obtained from the dough, particularly a baked product, which is improved by the action of the phospholipase according to the invention relative to a dough or product in which the phospholipase according to the invention is not incorporated. The improved property may include, but is not limited to, increased strength of the dough, increased elasticity of the dough, increased stability of the dough, reduced stickiness of the dough, improved extensibility of the dough, improved flavour of the baked product, improved anti-staling of the baked product.

The improved property may be determined by comparison of a dough and/or a baked product prepared with and without addition of a polypeptide of the present invention in accordance with the methods of present invention are described below in the Examples. Organoleptic qualities may be evaluated using procedures well established in the baking industry, and may include, for example, the use of a panel of trained taste-testers.

The term "increased strength of the dough" is defined herein as the property of a dough that has generally more elastic properties and/or requires more work input to mould and shape.

The term "increased elasticity of the dough" is defined herein as the property of a dough which has a higher tendency to regain its original shape after being subjected to a certain physical strain.

The term "increased stability of the dough" is defined herein as the property of a dough that is less susceptible to mechanical abuse thus better maintaining its shape and volume.

The term "reduced stickiness of the dough" is defined herein as the property of a dough that has less tendency to adhere to surfaces, e.g., in the dough production machinery, and is either evaluated empirically by the skilled test baker or measured by the use of a texture analyser (e.g., TAXT2) as known in the art.

The term "improved extensibility of the dough" is defined herein as the property of a dough that can be subjected to increased strain or stretching without rupture.

The term "improved machineability of the dough" is defined herein as the property of a dough that is generally less sticky and/or more firm and/or more elastic.

The term "increased volume of the baked product" is measured as the specific volume of a given loaf of bread (volume/weight) determined typically by the traditional rapeseed displacement method.

The term "improved crumb structure of the baked product" is defined herein as the property of a baked product with finer and/or thinner cell walls in the crumb and/or more uniform/homogenous distribution of cells in the crumb and is usually evaluated empirically by the skilled test baker.

The term "improved softness of the baked product" is the opposite of "firmness" and is defined herein as the property of a baked product that is more easily compressed and is evaluated either empirically by the skilled test baker or measured by the use of a texture analyzer (e.g., TAXT2) as known in the art.

The term "improved flavor of the baked product" is evaluated by a trained test panel.

The term "improved anti-staling of the baked product" is defined herein as the properties of a baked product that have a reduced rate of deterioration of quality parameters, e.g., softness and/or elasticity, during storage.

The term "dough" is defined herein as a mixture of flour and other ingredients firm enough to knead or roll. The dough may be fresh, frozen, pre-bared, or pre-baked. The preparation of frozen dough is described by Kulp and Lorenz in Frozen and Refrigerated Doughs and Batters.

The term "baked product" is defined herein as any product prepared from a dough, either of a soft or a crisp character. Examples of baked products, whether of a white, light or dark type, which may be advantageously produced by the present invention are bread (in particular white, whole-meal or rye bread), typically in the form of loaves or rolls, French baguette-type bread, pasta, pita bread, tortillas, tacos, cakes, pancakes, biscuits, cookies, pie crusts, steamed bread, and crisp bread, and the like.

Phospholipases of the present invention and/or additional enzymes to be used in the methods of the present invention may be in any form suitable for the use in question, e.g., in the form of a dry powder, agglomerated powder, or granulate, in particular a non-dusting granulate, liquid, in particular a stabilized liquid, or protected enzyme such described in WO01/11974 and WO02126044. Granulates and agglomerated powders may be prepared by conventional methods, e.g., by spraying the phospholipase according to the invention onto a carrier in a fluid-bed granulator. The carrier may consist of particulate cores having a suitable particle size. The carrier may be soluble or insoluble, e.g., a salt (such as NaCl or sodium sulphate), sugar (such as sucrose or lactose), sugar alcohol (such as sorbitol), starch, rice, corn grits, or soy. The phospholipase according to the invention and/or additional enzymes may be contained in slow-release formulations. Methods for preparing slow-release formulations are well known in the art. Adding nutritionally acceptable stabilizers such as sugar, sugar alcohol, or another polyol, and/or lactic acid or another organic acid according to established methods may for instance, stabilize liquid enzyme preparations.

The phospholipases according to the invention may also be incorporated ub yeast comprising compositions such as disclosed in EP-A-0619947, EP-A-0659344 and WO02/49441.

For inclusion in pre-mixes of flour it is advantageous that the polypeptide according to the invention is in the form of a dry product, e.g., a non-dusting granulate, whereas for inclusion together with a liquid it is advantageously in a liquid form.

One or more additional enzymes may also be incorporated into the dough. The additional enzyme may be of any origin, including mammalian and plant, and preferably of microbial (bacterial, yeast or fungal) origin and may be obtained by techniques conventionally used in the art.

In a preferred embodiment, the additional enzyme may be an amylase, such as an alpha-amylase (useful for providing sugars fermentable by yeast and retarding staling) or beta-amylase, cyclodextrin glucanotransferase, peptidase, in particular, an exopeptidase (useful in flavour enhancement), transglutaminase, lipase (useful for the modification of lipids present in the dough or dough constituents so as to soften the dough), phospholipase, cellulase, hemicellulase, in particular a pentosanase such as xylanase (useful for the partial hydrolysis of pentosans which increases the extensibility of the dough), protease (useful for gluten weakening in particular when using hard wheat flour), protein disulfide isomerase, e.g., a protein disulfide isomerase as disclosed in WO 95/00636, glycosyltransferase, peroxidase (useful for improving the dough consistency), laccase, or oxidase, e.g., an glucose oxidase, hexose oxidase, aldose oxidase, pyranose oxidase, lipoxygenase or L-amino acid oxidase (useful in improving dough consistency).

When one or more additional enzyme activities are to be added in accordance with the methods of the present invention, these activities may be added separately or together with the polypeptide according to the invention, optionally as constituent(s) of the bread-improving and/or dough-improving composition. The other enzyme activities may be any of the enzymes described above and may be dosed in accordance with established baking practices.

The present invention also relates to methods for preparing a baked product comprising baking a dough obtained by a method of the present invention to produce a baked product. The baking of the dough to produce a baked product may be performed using methods well known in the art.

The present invention also relates to doughs and baked products, respectively, produced by the methods of the present invention.

The present invention further relates to a pre-mix, e.g., in the form of a flour composition, for dough and/or baked products made from dough, in which the pre-mix comprises a polypeptide of the present invention. The term "pre-mix" is defined herein to be understood in its conventional meaning, i.e., as a mix of baking agents, generally including flour, which may be used not only in industrial bread-baking agents, generally including flour, which may be used not only in industrial bread-baking plants/facilities, but also in retail bakeries. The pre-mix may be prepared by mixing the polypeptide or a bread-improving and/or dough-improving composition of the invention comprising the polypeptide with a suitable carrier such as flour, starch, a sugar, or a salt. The pre-mix may contain other dough-improving and/or bread-improving additives, e.g., any of the additives, including enzymes, mentioned above.

The present invention further relates to baking additives in the form of a granulate or agglomerated powder, which comprise a polypeptide of the present invention. The baking additive preferably has a narrow particle size distribution with more than 95% (by weight) of the particles in the range from 25 to 500 µm.

In dough and bread making the present invention may be used in combination with the processing aids defined hereinbefore such as the chemical processing aids like oxidants (e.g. ascorbic acid), reducing, agents (e.g. L-cysteine), oxidoreductases (e.g. glucose oxidase) and/or other enzymes such as polysaccharide modifying enzymes (e.g. α-amylase, hemicellulase, branching enzymes, etc.) and/or protein modifying enzymes (endoprotease, exoprotease, branching enzymes, etc.).

EXAMPLE 1

Fermentation of *Aspergillus niger*

Phospholipases encoded by the nucleotide sequence as provided herein were obtained by constructing expression plasmids containing the DNA sequences, transforming an *A. niger* strain with this plasmid and growing the *Aspergillus niger* strains in the following way.

Fresh spores ($10^6$-$10^7$) of *A. niger* strains were inoculated in 20 ml CSL-medium (100 ml flask, baffle) and grown for 20-24 hours at 34° C. and 170 rpm. After inoculation of 5-10 ml CSL pre-culture in 100 ml CSM medium (500 ml flask, baffle) the strains were fermented at 34° C. and 170 rpm for 3-5 days.

Cell-free supernatants were obtained by centrifugation in 50 ml Greiner tubes (30 minutes, 5000 rpm). The supernatants were pre-filtered over a GF/A Whatman Glass microfiber filter (150 mm Æ) to remove the larger particles, adjusted to pH 5 with 4 N KOH (if necessary) and sterile filtrated over a 0.2 µm (bottle-top) filter with suction to remove the fungal material. The supernatant were stored at 4° C. (or −20° C.).

The CSL medium consisted of (in amount per litre): 100 g Corn Steep Solids (Roquette), 1 g $NaH_2PO_4*H_2O$, 0.5 g $MgSO_4*7H_2O$, 10 g glucose*$H_2O$ and 0.25 g Basildon (antifoam). The ingredients were dissolved in demi-water and the pH was adjusted to pH 5.8 with NaOH or $H_2SO_4$; 100 ml flasks with baffle and foam ball were filled with 20 ml fermentation broth and sterilized for 20 minutes at 120° C. after which 200 µl of a solution containing 5000 IU/ml penicillin and 5 mg/ml Streptomycin was added to each flask after cooling to room temperature.

The CSM medium consisted of (in amount per litre): 150 g maltose*H2O, 60 g Soytone (pepton), 1 g $NaH_2PO_4*H_2O$, 15 g $MgSO_4*7H_2O$, 0.08 g Tween 80, 0.02 g Basildon (antifoam), 20 g MES, 1 g L-arginine. The ingredients were dissolved in demi-water and the pH was adjusted to pH 6.2 with NaOH or $H_2SO_4$; 500 ml flasks with baffle and foam ball were filled with 100 ml fermentation broth and sterilized for 20 minutes at 120° C. after which 1 ml of a solution containing 5000 IU/ml penicillin and 5 mg/ml Streptomycin was added to each flask after cooling to room temperature.

EXAMPLE 2

Purification of the Phospholipases of the Invention

Step 1—Preparation of Ultrafiltrates

The supernatants of the cultures, as obtained in Example 1, were ultrafiltrated to remove the low molecular contaminations that could interfere with the enzymatic activity determinations and the baking tests. Ultrafiltration of 30 ml supernatant was performed in a Millipore Labscale TFF system equipped with a filter with a 10 kDa cut-off.

Depending on their colour, the samples were washed 3-5 times with 40 ml volumes of cold 100 mM phosphate buffer pH 6.0 including 0.5 mM $CaCl_2$ The final volume of the enzyme solution was 30 ml and is further referred to as "ultrafiltrate".

Step 2—Determination of the Phospholipase Concentration by A280 and HPSEC.

The concentration of the phospholipase in the ultrafiltrate was calculated from the extinction at 280 nm (A280) attributable to the phospholipase and the calculated molecular extinction coefficient of the phospholipase. Measurement of the A280 was performed in an Uvikon XL Secomam spectrophotometer (Beun de Ronde, Abcoude, The Netherlands).

The molecular extinction coefficient of an enzyme can be calculated from the number of tyrosine, tryptophan and cysteine residues per enzyme molecule (S. C. Gill and P. H. von Hippel, Anal. Biochem. 182, 319-326 (1989)). The molecular extinction coefficient of these amino acids are 1280, 5690 and 120 $M^{-1}.cm^{-1}$ respectively. The number of tyrosine, tryptophan and cysteine residues in the phospholipase of the invention can be deduced from the protein sequences selected from the group consisting of SEQ ID NO: 3, 6, 9, 12 and 15. The calculated extinction coefficients of the phospholipases of the invention are summarized in Table 1.

TABLE 1

| Phospholipase | SEQ ID NO: | # amino acids | | | Calculated M.W. (Da) | Calculated extinction coefficient at 280 nm | |
|---|---|---|---|---|---|---|---|
| | | Trp | Tyr | Cys | | $M^{-1} \cdot cm^{-1}$ | $(1 \text{ mg/ml})^{-1} \cdot cm^{-1}$ |
| PLP03 | 3 | 7 | 22 | 4 | 49683 | 165490 | 3.3 |
| PLP06 | 6 | 6 | 10 | 7 | 31694 | 91880 | 2.9 |
| PLP15 | 9 | 11 | 27 | 9 | 68440 | 217300 | 3.2 |
| PLP26 | 12 | 16 | 23 | 8 | 68255 | 222870 | 3.3 |
| PLP34 | 15 | 12 | 28 | 8 | 70320 | 228560 | 3.3 |

The extinction of the ultrafiltrate at 280 nm (A280) that is attributable to the phospholipase depends on the purity of the enzyme sample. This purity was determined using HPSEC (High Performance Size Exclusion Chromatography) with a TSK SW-XL column (300*7,8 mm; MW range 10-300 kDa). The elution buffer consisted of 25 mM sodium phosphate buffer pH 6.0 and was used at a flow of 1 ml/min. Samples of 5-100 µl were injected. The absorbance at 280 nm was measured.

The A280 in the ultrafiltrate attributable to the phospholipase of the invention was obtained from the ratio of the peak surface of the respective phospholipase peak in the chromatogram and the total surface of the peaks absorbing at 280 nm. The phospholipase concentration in the ultrafiltrate was then calculated by multiplying the A280 of the ultrafiltrate by the ratio described above and divided by the calculated extinction coefficient (1 mg/ml solution—Table 1 most right column) for each phospholipase.

EXAMPLE 3
Activity Measurements

The ultrafiltrates obtained in Example 2, were subjected to the following enzyme activity measurements:
Phospholipase $A_1$ or $A_2$
Lysophospholipase
Phospholipase C
Galactolipase activity
Fungal alpha-amylase Phospholipase A was determined spectrophotometrically by using 1,2-dithiodioctanoyl-phosphatidylcholine as a substrate. Phospholipase A hydrolyses the sulphide bond at the 1 position (PLA1) or the 2 position (PLA2) thereby liberating 4 thio-octanoic acid which, in a subsequent reaction reacts with 4,4'-dithiopyridine to form 4-thiopyridone. The latter is in tautomeric equilibrium with 4-mercaptopyridine that absorbs at 334 nm. The reaction is carried out in 0.1 M acetate buffer pH 4.0+0.2% Triton-X100 at 37° C. One phospholipase A unit (PLA) is defined as the amount of enzyme that liberates 1 micromole of 4 thio-octanoic acid per minute at the reaction conditions stated.

Lysophospholipase activity was determined with $^{31}P$-NMR spectroscopy by using lysophosphatidyl-choline as a substrate. Lysophospholipase hydrolyses the ester bond thereby liberating the fatty acid from the glycerol moiety. The so-formed glycerolphosphocholine is quantified using NMR.

The reaction is carried out in 50 mM acetic acid buffer pH 4.5 further containing 1 mg/ml lysophosphatidylcholine and 5 mM $CaCl_2$ for 30 minutes at 55° C. One lysophospholipase unit (LPC) is defined as the amount of enzyme that forms 1 micromole of 4 glycerolphosphocholine per minute at the reaction conditions stated.

Phospholipase C activity was determined spectrophotometrically by using para-nitrophenylphosphorylcholine as a substrate. Phospholipase C hydrolyses the ester bond thereby liberating para-nitrophenol that absorbs at 405 nm.

The reaction is carried out in 100 mM acetic acid buffer pH 5.0 further containing 20 mM $CaCl_2$, 0.25% Triton X-100 and 20 mM para-nitrophenylphosphorylcholine for 7 minutes at 37° C. The reaction is stopped and the pH increased by adding 0.75 volume of a 1 M TRIS solution to one volume assay mixture after which the extinction at 405 nm is measured ($\epsilon_{405\ nm}$=18500 $M^{-1}.cm^{-1}$).

One phospholipase C unit is defined as the amount of enzyme that forms 1 micromole of para-nitrophenol per minute at the reaction conditions stated.

Galactolipase activity was determined with H-NMR spectroscopy by using digalactosyldiglyceride as a substrate, according to the method described by Hirayama and Matsuda (1972) Agric. Biol. Chem. 36, 1831. Galactolipase hydrolyses the ester bond between the fatty acids and the glycerol backbone thereby liberating one or both fatty acids.

The reaction is carried out in 50 mM acetic acid buffer pH 4.5 further containing 4 mM $CaCl_2$, 0.2% Triton X-100 and 1 mg/ml digalactosyldiglyceride (Lipid Products) for 30 minutes at 30° C.

One galactolipase unit is defined as the amount of enzyme that forms 1 micromole of fatty acid per minute at the reaction conditions stated.

The activity of the fungal alpha-amylase was measured using Phadebas Amylase test tablets (Pharmacia). Phadebas tablets contain a water insoluble starch substrate and a blue dye, bound by cross-linking to the substrate. The substrate is hydrolysed by fungal amylase, releasing dyed soluble maltodextrines that go into solution. A calibration curve was prepared with a solution containing a reference fungal alpha amylase activity.

From the reference and unknown samples appropriate dilutions were prepared in 50 mM malic acid buffer pH 5.5. Samples of 5 ml were incubated with 30° C. for 5 minutes, a Phadebas tablet was added and after 15 minutes the reaction was stopped by the addition of 1.0 ml 0.5 N sodium hydroxide. The mixtures were allowed to cool down to room temperature for 5 minutes after which 4.0 ml water was added, shaken by hand and after 15 minutes the samples were centrifuged at 4700 rpm for 10 minutes. The extinction of the top layers was measured at 620 nm. The OD 620 nm is a measure for fungal alpha amylase activity;

One fungal amylase unit (FAU) is defined herein as the amount of enzyme that converts 1 gram of starch (100% dry matter) per hour into a product having a transmission at 620 nm after reaction with a iodine solution of known strength at the reaction conditions stated.

TABLE 2

Phospholipase activities in the ultrafiltrates as prepared in Example 2.

| Phospholipase | Protein (mg/ml) BCA method | Protein (mg/ml) 280 nm analysis | fungal amylase FAU/ml | phospholipase A PLA/ml | phospholipase C Units/ml | lysophospholipase Units/ml | galactolipase Units/ml |
|---|---|---|---|---|---|---|---|
| PLP03 | 4.04 | 3.3 | 1.07 | 0.23 | 5.5 | 7 | 0.55 |
| PLP06 | 2.51 | 0.4 | 2.14 | 26.9 | 0.01 | 20 | 49.8 |
| PLP15 | 4.37 | 1.7 | 1.14 | 206 | 0.01 | >1300 | 0.19 |
| PLP26 | 2.21 | 1.4 | 3.24 | 0.24 | 0.01 | 67 | 0.21 |
| PLP34 | 3.87 | 0.07 | 7.97 | 2.29 | nd | 200 | 0.31 |

Phospholipase activities in units per mg protein determined by the A280 nm method of the ultrafiltrates as prepared in Example 2.

| Phospholipase | fungal amylase FAU/mg | phospholipase A PLA/mg | phospholipase C Units/mg | lysophospholipase Units/mg | galactolipase Units/mg |
|---|---|---|---|---|---|
| PLP03 | 0.3 | 0.1 | 1.7 | 2.1 | 0.2 |
| PLP06 | 5.4 | 67.3 | 0.0 | 50.0 | 124.5 |
| PLP15 | 0.7 | 121.2 | 0.0 | 764.7 | 0.1 |
| PLP26 | 2.3 | 0.2 | 0.0 | 47.9 | 0.2 |
| PLP34 | 113.9 | 32.7 | ND | 2857.1 | 4.4 |

In addition to the activities mentioned, minor activities of glucoamylase and xylanase were also present, however in such low amounts that these enzymes did not interfere in the baking experiments described in example 4.

EXAMPLE 4

Baking Experiments 1—Pup Loaves

Pup loaves were baked from 150 gram dough pieces obtained by mixing 200 g flour (Kolibri™/Ibis™ in a ratio of 80/20), 1,4 g dried bakers yeast (Fermipan®), 4 g salt, 3 g sugar, 10 mg ascorbic acid, 116 g water and 2 g fat. After mixing for 6 minutes and 15 seconds in a pin mixer, the dough was divided into pieces of 150 grams and proofed for 45 minutes at 30° C., punched, proofed for another 25 minutes, moulded and panned. Proofing took place at a relative humidity of 90-100%. After a final proof of 70 minutes at 30° C., the dough was baked for 20 minutes at 225° C.

The various effects (Table 3) of the different phospholipases in the baking experiments were compared with a control containing the same amount of fungal amylase that was added otherwise by the dosage of the ultrafiltrate (for the fungal amylase activity in the ultrafiltrates see Table 2). This was necessary since the amounts of fungal amylase added with the phospholipases in particular affected the loaf volume, not the other parameters. The volume of the breads with the control amount of fungal amylase added was taken as 100%.

TABLE 3

| | | Score | | | | |
|---|---|---|---|---|---|---|
| | effect | 1 | 2 | 3 | 4 | 5 |
| dough | dough stickiness | too sticky | sticky | control bread | much better | excellent dry |
| | dough extensibility | Too short | Shorter than the control | control bread | good | too long |
| baked bread | crumb structure | poor | non-uniform | control bread | good | excellent |
| | crust colour | Nearly white | too light | control bread | excellent | too dark |
| | crumb colour | Far too yellow | too yellow | control bread | excellent | absolutely white |

Loaf volume was determined by the Bread Volume Measurer BVM-3 (RI Cards Instruments AB, Viken, Sweden). The principle of this measurement is based on the reflection of ultrasound measured by a sensor around a rotating bread. A measurement time was taken of 45 seconds.

Dough stickiness and extensibility were evaluated by a qualified baker using the scale depicted in Table 3. The average of 2 loaves per object was measured.

After these tests the dough pieces were rounded and a first proof was performed for 45 minutes at 30° C. and hereafter the dough was punched, moulded, panned, proofed for 75 minutes at 30° C. The relative humidity during the proofs was set at 85%.

Subsequently the stability of the proofed dough was judged by the presence of bladders, torn side crust and irregular curved surfaces of the crust. The dough pieces were baked for 20 minutes at 225° C. Loaf volumes were determined by the BVM-3 method: in the table the average is presented of 2 breads that are baked from the same object.

The crumb structure was judged by a qualified baker using the scale depicted in Table 3. After storing the loaves for three days in polyethylene bags at room temperature crumb firmness was measured using a Stevens Texture Analyser. Two slices of 2 cm thickness from the centre of each loaf were analysed by the texture analyser using a probe of 1.5 inch diameter, a compression depth of 5 mm (25%) and a rate of compression of 0.5 mm/sec. In the table the average is shown of two measurements.

Crust colour was judged by a qualified baker according to the scale depicted in Table 3. As a reference the standard recipe for Dutch tin bread was used.

Crumb colour was judged by a qualified baker according to the scale depicted in Table 3. The colour of the crumb of the control breads was judged as normal (3). As a positive control the breads of 2 objects are used with the same composition as the control plus 0.5% soya flour. The proofing and baking procedure are the same as that of the control without soya flour. The latter is judged as "excellent".

The overhanging top of the bread was judged by the hanging of the top in relation to the baking tin, the lower the edges of the top the lower the judgement. The less hanging, the better the judgement,

TABLE 4

Baking performance of the phospholipases of the invention

| parameter | Phospholipase | | | | |
|---|---|---|---|---|---|
| | PLP03 | PLP06 | PLP15 | PLP26 | PLP34 |
| Volume (%) | 100 | 108 | 112 | 110 | 107 |
| dough stickiness | 5 | 3 | 3 | 3 | 3 |
| dough extensibility | 2 | 3 | 3 | 2 | 3 |
| dough stability | 4 | 5 | 4 | 4 | 4 |
| crumb structure | 4 | 5 | 4 | 4 | 4 |
| crust colour | 4 | 4 | 4 | 4 | 4 |
| crumb colour | 3 | 5 | 4 | 4 | 4 |
| overhanging top | 4 | 4 | 4 | 3 | 4 |

EXAMPLE 5

Baking Experiments 2—Batard

The baking performance of phospholipases according to the invention was tested in the French type of bread called "batard". Preparation of batards in a standard baking process was done by mixing 3000 g of wheat flour at circa 20° C., 70 g compressed yeast, 60 g salt, 68 ppm ascorbic acid, 17 ppm Fermizyme® $P_{200}$ (fungal α-amylase), 30 ppm Fermizyme® $HS_{2000}$ (fungal hemicellulase), 7 ppm Bakezyme® P500 and 1680 ml water (8-10° C.) in a spiral mixer (Diosna: 2 minutes in speed 1; 100 Wh input in speed 2). The dough temperature was 27° C. The machineability of the dough was analyzed by hand by a baker. The dough was given a bulk proof of 15 minutes in a proofing cabinet at 32° C. and 90% RH. Afterwards the dough was divided into 6 pieces of 350 g, rounded and proofed for 15 minutes at 32° C. and 90% RH. At the end of this period the dough pieces were moulded and shaped and given a final proof of 90 minutes at 32° C. and 90% RH. The fully proofed doughs were cut in the length of the dough piece and baked in an oven at 240° C. for 30 minutes with initial steam addition. After cooling down to room temperature the volumes of the loaves were determined by the BVM-method (see example 4).

Break, shred and shape of the breads were analysed directly after cooling down to room temperature by a qualified baker using the score in Table 5. After 16 hours (overnight) storage in a closed box at room temperature the crumb quality was assessed a qualified baker. The value for the breads was derived from 1 object.

TABLE 5

| effect | Score | | | | |
|---|---|---|---|---|---|
| | 1 | 2 | 3 | 4 | 5 |
| Break and shred | extremely weak and soft | weak and soft | control bread | thin and crispy crust firm break of the cut | crust too thin, too hard |
| Crumb structure | poor | not uniform | control bread | good | excellent |
| shape  height | flat | medium | control bread | larger than (3) | Much larger than (3) |
| cut | cut closed | cut closed | control bread | completely opened | completely opened; teared |

TABLE 6

Baking performance of the phospholipases of the invention

| parameter | none | Phospholipase | | | |
|---|---|---|---|---|---|
| | | PLP03 | PLP06 | PLP26 | PLP34 |
| dosage* | 0 | not tested | 10 | 20 | 21 |
| Loaf volume (%) | 100 | not tested | 109 | 105 | 109 |
| Break and Shred | 3 | not tested | 4 | 4 | 4 |
| Shape | 3 | not tested | 4 | 4 | 4 |
| Crumb structure | 3 | not tested | 4 | 4 | 4 |

*in ppm based on flour weight and enzyme weight determined by the A280 method

We claim:

1. An isolated or recombinant polynucleotide, wherein the polynucleotide is selected from the group consisting of:
   (a) polynucleotides encoding a phospholipase comprising SEQ ID NO: 3,
   (b) polynucleotides comprising SEQ ID NO: 1 or 2, and
   (c) polynucleotides which are at least 95% sequence identical to the polynucleotide of SEQ ID NO: 1 or 2, wherein the polynucleotides encode a protein having phospholipase activity.

2. The isolated or recombinant polynucleotide according to claim 1, wherein the polynucleotide is a polynucleotide that encodes a phospholipase comprising SEQ ID NO: 3.

3. The isolated or recombinant polynucleotide according to claim 1, wherein the polynucleotide is a polynucleotide that comprises SEQ ID NO: 1 or 2.

4. The isolated or recombinant polynucleotide according to claim 1, wherein the polynucleotide is hybridizable under the stringent conditions comprising a wash in a solution of 1x sodium chloride/sodium citrate (SSC) and 0.1% sodium dodecyl sulfate (SDS) at 65° C. to the full length complement of the polynucleotide of SEQ ID NO: 1.

5. The isolated or recombinant polynucleotide according to claim 1, wherein the polynucleotide is hybridizable under the stringent conditions comprising a wash in a solution of 1x sodium chloride/sodium citrate (SSC) and 0.1% sodium dodecyl sulfate (SDS) at 65° C. to the full length complement of the polynucleotide of SEQ ID NO: 2.

6. The isolated or recombinant polynucleotide according to claim 1, wherein the polynucleotide is a polynucleotide that is at least 95% sequence identical to the polynucleotide of SEQ ID NO: 1.

7. The isolated or recombinant polynucleotide according to claim 1, wherein the polynucleotide is a polynucleotide that is at least 95% sequence identical to the polynucleotide of SEQ ID NO: 2.

8. The isolated or recombinant polynucleotide according to claim 1, wherein the polynucleotide is obtained from a filamentous fungus.

9. The isolated or recombinant polynucleotide according to claim 8, wherein the polynucleotide is obtained from *Aspergillus niger*.

10. A vector comprising the polynucleotide according to claim 1.

11. The vector according to claim 10 further comprising regulatory sequences operatively linked with and suitable for expression of the polynucleotide in a host cell.

12. The vector according to claim 11, wherein the host cell is a filamentous fungus.

13. An isolated or transformed host cell comprising the polynucleotide according to claim 1.

14. The isolated or transformed host cell according to claim 13, wherein the host cell expresses a phospholipase.

15. The isolated or transformed host cell according to claim 13, wherein the host cell is a filamentous fungus.

16. An isolated or transformed host cell comprising the vector according to claim 10.

17. The isolated or transformed host cell according to claim 16, wherein the host cell expresses a phospholipase.

18. The isolated or transformed host cell according to claim 16, wherein the host cell is a filamentous fungus.

19. A method for manufacturing the polynucleotide according to claim 1 or a vector comprising the polynucleotide, said method comprising:
   (a) culturing a host cell transformed with the polynucleotide or the vector; and
   (b) isolating the polynucleotide or the vector from the host cell.

20. A method for manufacturing a phospholipase, said method comprising:
   (a) transforming a suitable host cell with the polynucleotide according to claim 1 or a vector comprising the polynucleotide,
   (b) culturing the transformed cell in a culture medium under conditions allowing expression of a phospholipase from the polynucleotide or the vector, and
   (c) optionally purifying the phospholipase from the transformed cell or the culture medium.

* * * * *